United States Patent [19]

Martens et al.

[11] Patent Number: 5,299,118
[45] Date of Patent: * Mar. 29, 1994

[54] METHOD AND SYSTEM FOR ANALYSIS OF LONG TERM PHYSIOLOGICAL POLYGRAPHIC RECORDINGS

[75] Inventors: Wim L. J. Martens, Eindhoven, Netherlands; Jaap I. Kap, Madison, Wis.

[73] Assignee: Nicolet Instrument Corporation, Madison, Wis.

[ * ] Notice: The portion of the term of this patent subsequent to Sep. 10, 2008 has been disclaimed.

[21] Appl. No.: 755,164

[22] Filed: Sep. 5, 1991

Related U.S. Application Data

[63] Continuation of Ser. No. 67,765, Jun. 26, 1987, Pat. No. 5,047,930.

[51] Int. Cl.$^5$ .................. G06F 15/42; A61B 5/04
[52] U.S. Cl. .................. 364/413.05; 128/731
[58] Field of Search .............. 364/413.01, 413.05; 128/731; 395/155

[56] References Cited

U.S. PATENT DOCUMENTS

| | | | |
|---|---|---|---|
| 3,774,593 | 11/1973 | Hakata et al. | 128/731 |
| 4,228,806 | 10/1980 | Lidow | 128/731 |
| 4,336,810 | 6/1982 | Anderson et al. | 128/702 |
| 4,579,125 | 4/1986 | Strobl et al. | 128/731 |
| 4,585,011 | 4/1986 | Broughton et al. | 128/733 |
| 4,610,259 | 9/1986 | Cohen et al. | 128/731 |
| 4,739,772 | 4/1988 | Hokanson et al. | 128/731 |
| 4,776,345 | 10/1988 | Cohen et al. | 128/731 |
| 4,794,533 | 12/1988 | Cohen | 364/413.05 |
| 5,047,930 | 9/1991 | Martens et al. | 364/413.04 |

OTHER PUBLICATIONS

Conference: Proceedings of the 9th Annual Rocky Mountain Bioengineering Symposium, Omaha, Neb., May 1-3, 1972, Courtney et al., "A Hybrid Computer System for Unsupervised Scoring of Sleep Records".
Journal A, vol. 26, No. 2, Lacroix et al., "New Algorithms for on-line automatic sleep scoring, and their application to mini and microcomputer", (abstract only).
Sleep (NY), vol. 14, No. 1, Van Gelder et al., "Real--Time Automated Sleep Scoring Validation of a Microcomputer-based System for Mice", (abstract only).
A. J. Lim, et al., "A Practical Method for Automatic Real-Time EEG Sleep State Analysis," IEEE Trans. on Biomedical Engineering, vol. BME-27, No. 4, Apr. 1980, pp. 212-220.
Published Patent Cooperation Treaty Application PCT/US85/01655, Pub. No. WO86/01391, published Mar. 13, 1986, Ravin, et al., "Brain Electrical Activity Analysis and Topographical Mapping".
C. A. Swenne, et al., "A Computerized Interactive Coronary Care Unit Monitoring System," IEEE Trans. on Biomedical Engineering, Jan. 1977, pp. 63-67.

(List continued on next page.)

Primary Examiner—Roy N. Envall, Jr.
Assistant Examiner—David Huntley
Attorney, Agent, or Firm—Foley & Lardner

[57] ABSTRACT

An analysis system accepts physiological sensor signals, including electroencephalogram (EEG) and other signals commonly sensed in sleep analysis, stores the raw data for later retrieval, extracts features from the digitized signal data which are of a type apt to be significant in classifying and detecting physiological functions (such as the state of sleep) and matches the extracted features to patterns which indicate the type of feature that has been extracted. The matched features are then utilized to classify for each epoch (limited period of time) the state of the physiological function (such as the stage of sleep) for that epoch. The results of the classification analysis are displayed on a CRT screen to the operator on a real time basis and in time correlation with representations of detected features from the various physiological signals. Upon completion of the tests, the operator can interact with the system to change the patterns by which the features are matched and the classification criteria, and can then re-analyze the data and have it redisplayed to demonstrate the results of the re-analysis.

11 Claims, 53 Drawing Sheets

OTHER PUBLICATIONS

P. Barone, et al., "GISPEM: A Graphic Interactive System for the Processing of Electrocardiographic Maps," Modern Electrocardiology, Proceedings of the IVth International Congress on Electrocardiology, Hungary, Sep. 20–23, 1977, pp. 127–131.

J. M. Gaillard et al., "Principals of Automatic Analysis of Sleep Records with a Hybrid System," Computers and Biomedical Research 6, (1973), pp. 1–13.

Anand Kumar, "A Real-Time System for Pattern Recognition of Human Sleep Stages by Fuzzy System Analysis," Pattern Recognition, Pergamon Press, 1977, vol. 9, pp. 43–46.

I. Gath, et al., "Computerized Method for Scoring of Polygraphic Sleep Recordings," Computer Programs in Biomedicine 11, 1980, pp. 217–233.

Anand Kumar et al., "Evaluation and Validation of an Automatic Method of Sleep Stage Classification of Human Sleep Recordings Done in the Homes," IEEE Proceedings of the International Conference on Cybernetics and Society, Oct. 26–28, 1981, pp. 516–519.

W. L. J. Martens, "Considerations on a Computerised Analysis of Long-Term EEG Recordings," British Journal of Clinical Practice 1982 Symposium Supplement 18, pp. 71–73.

W. J. L. Martens, et al., "Considerations on a Computerized Analysis of Long-Term Polygraphic Recordings," Proceedings of the MLE Symposium, Bonn, Germany, May 1982, pp. 265–271.

W. J. L. Martens, et al., "Considerations On and Preliminary Results of Computerized Ictal and Interictal Analysis of Long-Term EEG Recordings," paper presented at the Second Cooperative Meeting on Epilepsy and E.E.G. of Austria, Belgium, Luxemburg, and Switzerland presented at Luxemburg, Oct. 19 and 20, 1984.

W. L. Martens, et al., "Computerized High Resolution Multi-Pattern Analysis of Long-Term EEG Recordings," Electroencephalography and Clinical Neurophysiology, vol. 61, No. 3, Sep. 1985, abstract of paper presented at the 11th International Congress of Electroencephalography and Clinical Neurophysiology, London, Aug. 25–30, 1985.

W. J. L. Martens, "Computerized High Resolution Multi Pattern Analysis of Longterm E.E.G. Recordings," copy of a poster displayed at the 11th International Congress of Electroencephalography and Clinical Neurophysiology, London, United Kingdom, Aug. 25–30, 1985.

S. R. Ray, et al., "Computer Sleep Stage Scoring-An Expert System Approach," Int. J. Bio-Medical Computing, vol. 19, 1986, pp. 43–61.

Jose C. Principe, et al., "SAMICOS—A Sleep Analyzing Microcomputer System," IEEE Transactions on Biomedical Engineering, vol. BME-33 No. 10, Oct., 1986, pp. 935–941.

E. Stanus, et al., "Automated Sleep Scoring: A Comparative Reliability Study of Two Algorithms," Electroencephalography and Clinical Neurophysiology, 1987, 66, pp. 448–456.

Advertising literature for CNS Computer Aided Sleep System (CASS) by CNS, Inc., Minneapolis, Minn.

Advertising literature for Oxford Medilog Sleep Stager.

Advertising literature for the Sleep Analyzing Computer by Microtronics, Inc., of Gainesville, Fla.

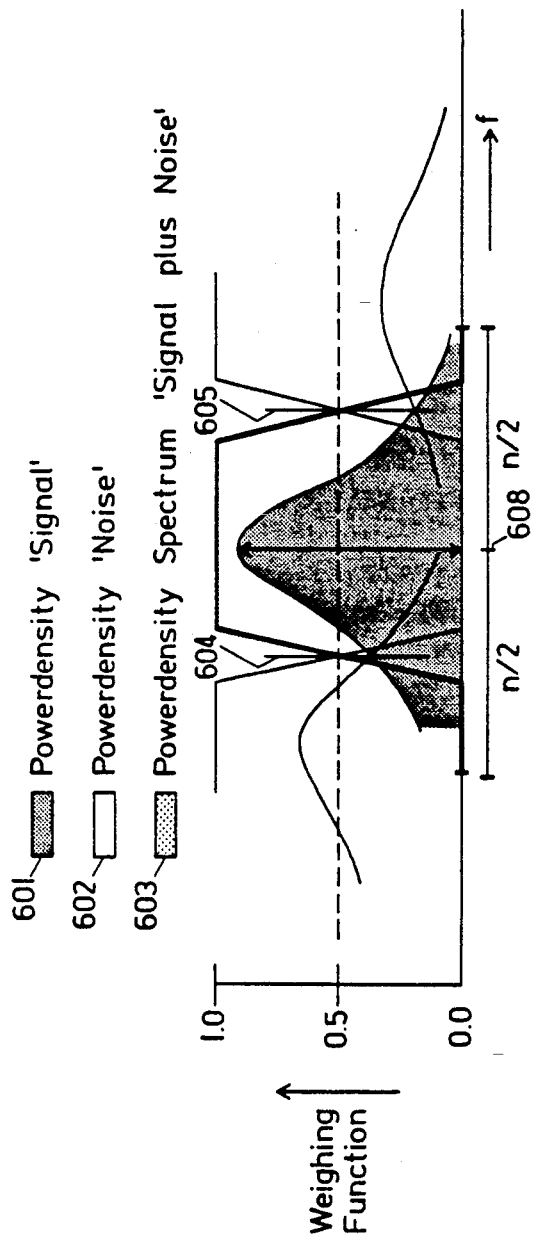
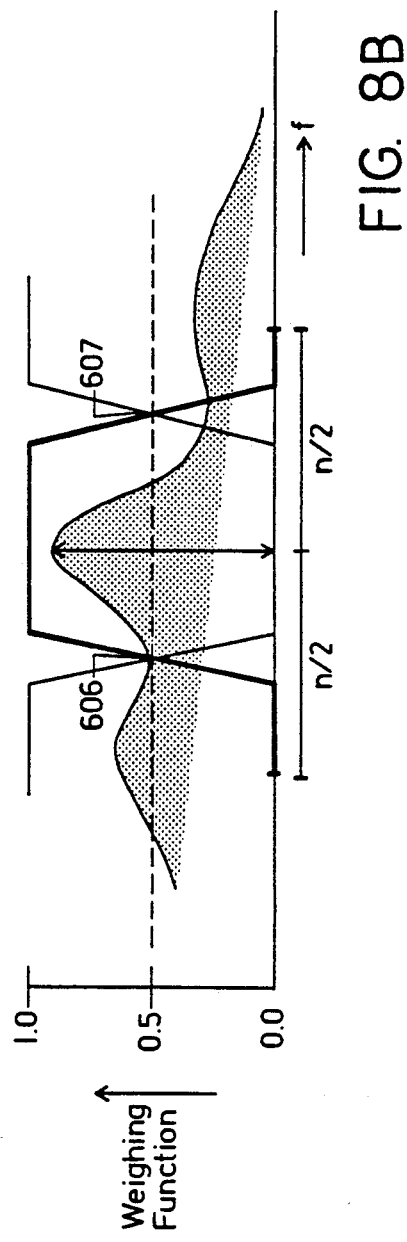
FIG. 8A
FIG. 8B

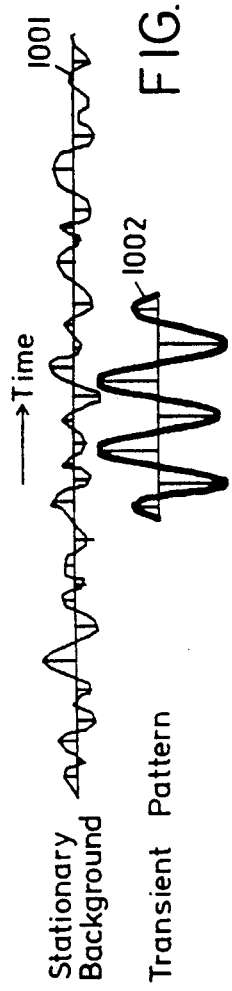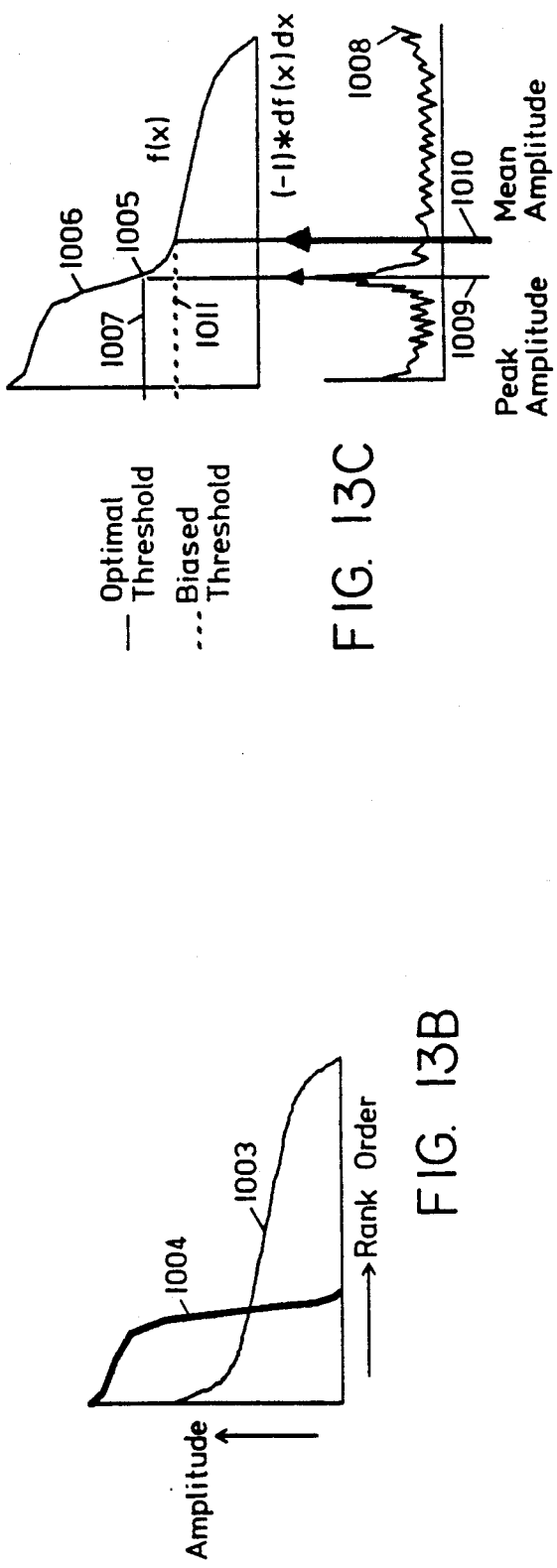
FIG. 13A
FIG. 13B
FIG. 13C
FIG. 13D

SLEEPSPINDLE

STANDARD DETECTION RULES
(& Unmodified Reference Levels)

1401 — Y  N — 1402

| | |
|---|---|
| Amplitude | |
|     Ratio to Backgr. | 4 |
|     Maximum | 80 |
|     Minimum | 20 |
| Frequency | |
|     Maximum | 15.0 |
|     Minimum | 11.5 |
| Time Duration | |
|     Maximum | 2.5 |
|     Minimum | 0.5 |
| Morphology | |
|     Polarity | |
|     Symmetry | — |
|     Harmonics | |
|     Subharmonics | |
| Synchrony | |
| Context | |
| Combination | |

FIG. 18

RECHTSCHAFFEN & KALES EMULATED CLASSIFICATION RULES
(& Unmodified Reference Levels)

| | Stage | | | | Awake | | REM |
|---|---|---|---|---|---|---|---|
| | IV | III | II | I | Alpha + | Alpha − | REM |
| Delta | >75 | >50 | 25-50 | <25 | <20 | <20 | <15 |
| # Delta Burst | | | | | | | |
| Theta | | | | | | | |
| # Theta Burst | | | | >1 | | | |
| Alpha | | | | | >50 | 20-50 | <10 |
| # Alpha Burst | | | | | | | |
| Beta | | | | | | | <10 |
| # Beta Burst | | | | | | | |
| # K-Compl. | | | >2 | | | | |
| # Spindle | | | >2 | | | | |
| # Sharp W. | | | | | | | |
| # REM | | | | | | | >2 |
| EMG (Chin) | | | | | | | <20 |

1701 — 30 Seconds Epoch
1702 — Y
1703 — N
1704 — ↕

FIG. 23

APNEA

CLASSIFICATION RULES
(& Unmodified Reference Levels)

2201 — Y | N — 2202

|              | Obstr.    | Central   | Mixed       |
|--------------|-----------|-----------|-------------|
| Amp./Ref. 1  |           |           |             |
| Amp./Ref. 2  | <50%      | <50%      | <50%        |
| Freq./Ref. 1 |           |           |             |
| Freq./Ref. 2 |           |           |             |
| Phase Angle  | >150      | <30       | 30-150      |
| EMG Interc.  | >30/Min.  | <10/Min.  | 10-30/Min.  |
| Body Posit.  |           |           |             |

FIG. 29

METHOD AND SYSTEM FOR ANALYSIS OF LONG TERM PHYSIOLOGICAL POLYGRAPHIC RECORDINGS

This is a continuation, of application Ser. No. 07/067,765, filed Jun. 26, 1987, now U.S. Pat. No. 5,047,930.

FIELD OF THE INVENTION

This invention pertains generally to the field of physiologic recording and analysis systems and particularly to systems which gather physiological data from several sources, store, analyze and display the data to an operator. Such systems are used, for example, in the monitoring of sleep and awake states in individual subjects.

BACKGROUND OF THE INVENTION

To aid the clinician in evaluating the physiological status of an individual, so called polygraphic monitoring is used to record a variety of measurable physiological variables which can be reviewed to determine the fluctuations of one or more physiological functions. One example of a physiological function receiving intensive study in a clinical setting is the state of sleep in individuals. For several decades, long term recordings on paper of electroencephalograms (EEG) alone and in combination with other physiological data such as obtained from electrooculorgrams (EOG), and electromyograms (EMG), heart rate monitoring, and respiration have been used to study and classify the process of sleep. Typically, to reveal the cyclic fluctuation of the depth of sleep, a description of various physiological phenomena, such as EEG, EOG, EMG, etc., is made by the clinician for each page of the EEG, etc., recording. A set of describing parameters is then used to classify the sleep into, for example, five classes or stages. The resulting graph, which indicates the stage of sleep for each consecutive recording page, is called a hypnogram. Normally, such a graph shows a damped oscillation with a cycle duration of about 90 minutes.

In 1968, Rechtschaffen and Kales established criteria for the classification of sleep which today are commonly used in sleep research. EEG, EOG, and EMG variables are considered in this classification scheme, and attention is paid as well to the ongoing EEG background activity (amplitude and time index of EEG rhythms) as well as to certain transient patterns (K complexes, sleepspindles, sharp Vertex waves, theta bursting, etc.). Attention is also paid to rapid eye movements (REM) and muscle tension (EMG) measured at the chin. The criteria of Rechtschaffen and Kales classify the stages of sleep—I through IV and REM sleep—based on how the monitored physiological variables meet prescribed rules, for example, the occurrence of sleepspindles for stage II, and whether the variables lay within (or exceed) certain values (e.g., for Stage IV the amplitude of delta waves must exceed 75 microvolts for more than 50% of the time). These rules for classifying sleep are well known and referenced in standard physiology handbooks.

Sleep problems may arise in individuals when the sleep is polyphasic, when there is too little sleep, and when the sleep is superficial or shows many shifts and awakenings, even if these last only a few seconds (micro-arousals). To determine possible causes of such sleep disturbances, a series of additional physiological variables must be recorded (polysomnography) and their relationship with disturbance of sleep must be studied. Right and left anterior tibialis EMG will reveal myoclonus "restless legs" syndrome. Electrocardiogram (EKG) signals can detect heart arrhythmia. Measurements of the movements of the rib cage and abdomen, the nostril and oral air flow, the intercostal EMG and the blood oxygen saturation can detect impaired breathing, apnea, and the type of apnea, and can trace the interference thereof with the process of sleep.

Complicating the characterization of sleep using the criteria of Rechtschaffen and Kales is the fact that EEG characteristics may differ considerably from individual to individual (e.g., the amplitude of delta waves typically changes with age, and may be affected by the thickness of the scalp, etc.) and physiological peculiarities may occur particularly when testing insomniacs and when encountering borderline abnormal and pathological EEG signals (e.g., absence of alpha rhythms, sleep-spindles, rapid eye movements, presence of epileptic paroxysmal activity, high muscle tension during REM, etc.). In clinical practice, therefore, the Rechtschaffen and Kales criteria are often applied in a flexible way, taking into account the individual's, EEG, EOG and EMG characteristics and pecularities, thereby yielding a more realistic classification of the sleep of a particular subject. In effect, the experience and judgment of the reviewing clinician are used to select or adjust the classification rules on a case by case basis.

Conventional automated sleep analysis systems typically carry out the classification of sleep using fixed Rechtschaffen and Kales criteria, thereby often giving rise to inconsistent and unreliable results, even if applied to a homogeneous subject group, for the reasons noted above. The results are particularly vulnerable to bias and inconsistency if applied to a variety of subject groups using the same fixed criteria. Generally, conventional systems do not allow inspection of the results of the various steps of data reduction leading up to the classification of sleep stages, thereby making it impossible for the clinician to assess the quality and reliability of the final analysis and classification. The inability of such systems to allow the clinician to monitor and verify the accuracy of the data reduction steps reduces the confidence of the clinician in the end results and limits the acceptability of such systems in clinical settings.

Most conventional polygraphic physiological data analysis systems focus on a single physiological function (for example, sleep) and on one type of analysis (for example, calculation of the hypnogram). Such systems have only limited value in clinical diagnosis where assesment and exploration of time relationships between physiological functions is of primary importance. In the visual analysis of clinical long term recordings, phenomena are often considered that are not embodied in the definition of a "normal" physiological function (for example, alpha/delta sleep, increased beta activity as a consequence of medication). Some of these phenomena have a short time duration and require an analysis with higher time resolution than under normal physiological conditions (e.g., micro arousals, burst like delta waves indicating short periods of unstable deep sleep, and micro sleep during the day). Some are highly complex, such as those seen in the clinical long term study of epilepsy where combinations of polyspike and slow-wave patterns are seen in bursts of a few seconds with an irregualar repetition frequency during sleep, as opposed to the classical regular three per second spike and slow-wave pattern seen during the day. Conventional systems cannot trace the occurance of such a variety of clinically relevant signal patterns for which both high time resolution and sophisticated pattern detection are required to accommodate the short time duration and complexity of the signal, respectively.

In addition to the monitoring of physiological variables which are related to the sleep state, polygraphic recordings over long time periods are also of use in detecting and diagnosing other physiological conditions. For example, nocturnal penile tumescence (NPT) can be recorded during sleep to diagnose the causes of impotence. Polygraphic monitoring during the day is sometimes used to diagnose narcolepsy and to determine the severity of daytime sleepiness. Polygraphic monitoring during both night and daytime situations with at least eight channels of EEG can be used to detect and monitor the occurance of epileptic seizures. Using the recorded data, the type of epilepsy can be specified and the effects of treatment can be evaluated. The monitoring of traditional physiological functions in combination with the monitoring of the functioning of the brain is also becoming more commonly used in accute situations such as during surgery and in the monitoring of patients in the Intensive Care Unit.

SUMMARY OF THE INVENTION

The present invention allows the recording and analysis of long term physiological data, such as that associated with determining sleep and awake states, in a manner which can readily accommodate both the systematic and the random variability of physiological signals among subjects. This accommodation may be carried out by the system automatically on a first level, yielding analyzed data and physiological characterizations of high reliability, and on a second level by allowing user interaction during reanalysis of the data to bring the expertise of the user to bear on the characterization of physiological states. The system of the present invention particularly provides display to the user of the results of selected steps of data reduction which make up the final classification of physiological function—for example, the classification of sleep stages—thus enhancing user confidence in the quality and reliability of the classification, as well as allowing the user to assess the intermediate data reduction procedures on an interactive basis if desired. Data corresponding to several physiological functions which vary with time can be determined and displayed together in time relationship, thereby aiding the clinician in exploring the causes of abnormalities and in making a diagnosis.

The polygraphic analysis system of the present invention accomplishes data analysis in basic time epochs, e.g., of thirty seconds duration, and analyzes the data gathered in each epoch in three steps: (a) feature extraction, (b) pattern detection, and (c) classification. Feature extraction takes place on a realtime basis and takes into account the frequency and amplitude variability of the input signals. The subsequent pattern detection and classification are performed initially using preset analysis criteria that are derived from an appropriate group of subjects which constitute a so called Knowledge Base which is available for access by the system. After initial automatic pattern detection and classification using the Knowledge Base, the user can interactively adapt the detection and classification criteria on an off line basis after the recording of data from the subject is completed and the primary analysis is done. The user selects, based on his own expertise and experience, criteria of choice to compensate for differences between the subject under test and the Knowledge Base—differences which may be either systematic (for example, differences as a function of age) or which are random and require adjustment of the rules and reference levels constituting a given set of criteria to accommodate the random signal variability which occurs from subject to subject. To facilitate an intelligible user interaction and allow verification of the results obtained as a consequence of the interaction, the feature extraction function follows a "mimic" approach, generating a user-system dialog which is in a "parlance" suited to the expected user, a person who is an expert in the visual analysis of the particular physiologicals signals being considered. The analysis rules that are used by the system are specifically selected to resemble rules found in physiological handbooks, which are familiar to the expert user, and the threshold levels that are presented to the user resemble levels with which the user is already familiar, thereby simplifying the user's task in analyzing and adjusting the performance of the system.

The analysis system of the invention includes multiple input channels for receiving several time varying physiological signals, such as those from EEG, EMG, and EOG electrodes. The time varying physiological signals are digitized in a analog to digital converter and the digital data are supplied to a computer controller which stores the data at a selected resolution level to long term storage and, on a real time basis, performs the initial feature extraction, pattern detection and classification steps. The controller includes a central processing unit with associated program and operational memory, and has access to long term storage devices such as magnetic and optical disks. The controller provides the output data through a display processor to communicate to the user through a display (CRT) screen, preferably in color, and also through a color printer for hard copy output. User input to the controller is provided through standard input devices such as a keyboard and/or mouse, etc. The system gathers data over relatively long periods of time, e.g., several minutes to 24 hours, and displays to the operator a continuously updated analysis of the physiological data, including the most recent epoch of physiological input signals. The raw data is simultaneously stored for later retrieval after all data gathering is completed. When data collection is finished, the analysis and classification results are displayed to the operator in a graphically comprehensible form. Because the input data has been stored over the term of test, if the operator wishes to reanalyze this data in an interactive fashion, it is readily available and can be run back through the system using the analysis/-characterization criteria that have been now selected by the operator.

As noted above, the first step in data analysis performed by this system is feature extraction. The "mimic" aspect of the feature extraction in accordance with the present invention comprises a quantification of signal parameters such as amplitude, frequency, time of occurance and duration. For signals such as EEG, EOG, and EMG, a distinction between transient patterns and background activity is made based on individual parts of the signal that exceed a selected amplitude threshold. In anticipation of the subsequent step of pattern detection, the parts of a signal which exceed the threshold amplitude are designated "transient pattern candidates" and the process of threshold discrimination can be considered predetection. The threshold levels are preferably selected to show a negative bias; that is, they are selected low enough to assure a low number of false negative transient candidates. In accordance with the present invention, automatic adaptation of feature extraction takes place with respect to the frequency and amplitude properties of the physiological signals. Adaptation with respect to frequency is accomplished by means of adaptive multiple band pass filtering of the EEG signal and adaptive high pass filtering of the EOG signal prior to further feature extraction. The EKG signals are preprocessed using fixed high-pass filtering, and other slowly varying physiological signals (e.g., respiratory channels, oxygen saturation, NPT, etc.) are low-pass filtered. Automatic adaptation to amplitude comprises calculation of the aforementioned thresholds in an adaptive way prior to extraction of features for background and "transient pattern candidates". This is carried out separately for each of the five EEG frequency bands and for EOG and EMG. For the remaining variables having an oscillatory characteristic, like respiratory variables, feature extraction consists of calculation of the amplitude and frequency (and phase angle between rib cage-abdomen movements) for each half wave of a cycle. For near dc signals such as oxygen saturation and NPT, the amplitude is determined every second.

The adaptive 5-fold band pass filtering of the EEG signal provides an optimal decomposition of the EEG signal into narrow-band rhythmic components. In this case, optimal means a maximum separation of the frequency components with a minimum of distortion. To allow exact determination of the time of occurance of broad-band (short lasting) transients, zero-phase filters are used to avoid phase distortion. The cutoff frequencies of adjacent filters are matched to let the filter bank pass all signal energy. The overall band width of the filter bank is fixed so that the low cutoff frequency of the first filter and the high cutoff frequency of the fifth filter are predetermined. The actual multiple band pass filtering is accomplished by a single forward Fourier Transform of the input time series followed by five consecutive inverse Fourier Transforms of the complex spectrum back to the time domain after multiplication of the frequency domain spectrum by a real trapezoid weighting function. The trailing and leading slopes of the weighting function are both preferably about one Hertz. Adaptation of the filtering takes place by adjustment of the center and low and high frequencies. The center frequencies of the filters correspond to the frequencies of peaks in the spectrum. Cutoff frequencies are selected to follow the criteria of Wiener for optimal filtering; that is, the weighting function equals 0.5 for those frequencies where signal and noise have equal power, i.e., those frequencies where trailing and leading edges of adjacent peaks ("noise") intersect with leading and trailing edges of the peak being considered ("the signal") respectively. When there are no peaks, the filter characteristics are set to default filter settings. The presence of peaks in the spectrum is determined by considering the first and second derivative of two noise-free analytic function fits to the input power-density spectrum. The first analytic function covers the low frequency area of the spectrum and focuses on delta activity; the second analytic function covers the middle and high frequency range of the spectrum and focuses on theta, alpha and sleepspindle activity. The advantage of splitting the spectrum into two parts is that subtle peaks in the middle and high frequency area have a lower chance of being obscured by the high energy in the lower part of the spectrum generally seen during sleep.

Adaptive high-pass filtering of the EOG signal aims at optimal reduction of EEG leakage, particularly of high amplitude delta waves during deep sleep. This adaptive filtering of the EOG signal comprises a high cutoff frequency going from 2 to 7.5 Hertz if the amplitude of delta waves increases from 20 to 75 microvolts. Below about 20 and above about 75 microvolts, the cutoff frequencies are preferably 2 and 7.5 Hertz, respectively.

The adaptive amplitude thresholds are selected to avoid erroneous pre-detection or miss detection of transient pattern candidates which would be caused by regular amplitude fluctuations during the time of recording and by the particular signal characteristics of the subject under study. The determination of an adaptive threshold starts with ranking of the rectified peak values of each half wave of the signal according to magnitude. In case of random noise, such a rank curve will typically show a sigmoid shape having the maximum value at the left and the minimum value at the right hand side. If one or more transients have substantial amplitudes, their envelope values will appear mainly at the high amplitude side of the sigmoid curve. In such a situation, the sigmoid curve would show a sudden steep slope. The amplitude at this steep transition slope should correspond to an optimal threshold value. Detection of a point of maximum slope can be done by calculating the first derivative of the rank curve, multipying by minus one, and finding the point at which the derivative is the maximum. However, it is preferred in the present invention to calculate the point of the mean value rather than the maximum value of the derivative. In addition to the advantage of providing a more stable estimate from a statistical point of view, the mean value will systematically correspond to a position on the rank curve toward the right hand side of the steep slope, and thus to a lower amplitude value than the point at which the derivative is a maximum. By utilizing the mean value, a negative bias is incorporated in the adaptive threshold, thus decreasing the number of false negatives in the predetection of transient pattern canidates.

After feature extraction has been performed on the incoming physiological data, the feature extracted data is then subjected to pattern detection and re-detection. For EEG signals, REMs and EMG signals, pattern detection consists of the selection of "transient pattern candidates" that fulfill certain detection criteria and rejection of those candidates that do not. The rejected candidates are then considered to be part of the background activity.

The detection procedure includes the application of rules and reference levels in four groups of criteria. The rules in the first group discribe signal properties of an isolated "transient pattern candidate". These signal properties include amplitude ratio to background (signal to noise ratio or SNR), minimum and maximum amplitude, time of occurence, time duration, polarity and, for the EEG patterns, also the frequency spread of energy over adjacent frequency bands (very short lasting patterns) and the presence of harmonics. Rules in the second group are related to the synchronism or lack thereof of a transient pattern candidate with a similar type of pattern in another channel (e.g., K-complexes, or conjugated REMs). Rules in the third group relate to the context of a particular transient pattern candidate in terms of its relationship with other types of patterns or measured variables. The fourth group of rules allows detection of patterns as a combination of other patterns.

In analyzing the EEG signal, particularly where the state of sleep is ultimately to be characterized, three types of patterns are seen:

(1) burstlike rhythmic activity (delta, theta, alpha and beta waves), to provide for the time index that a rhythm is present in an epoch, (2) deterministic transient activity (K-complexes, sleepspindles, and sharp waves), (3) artifacts subdivided into low frequency, high frequency and broad band noise to avoid misclassification.

The minimum number of EEG channels to be used for sleep analysis is one; however, averaged values of more than one EEG channel will give use to a more stable estimate of signal properties and thus to a more reliable classification of sleep. A separate display of individual EEG channels allows assessment of the distribution of signal patterns over the scalp and thus reveal an assymnetry, localized epliectic activity, and so forth.

The EOG signal is used to detect Rapid Eye Movements (REM) and Slow Eye Movements. Burstlike EMG activity is detected from each EMG channel.

Conditions of hypopnea and apnea are detected using variables computed with data from the respiratory channels. Actual detection of these conditions is done by comparison with reference levels. There are typically two type of reference levels. The first, traditional type consists of fixed levels derived from a calibration procedure carried out before starting actual recording. The second type uses levels that represent the moving average of a parameter (for example, amplitude of the signal) over time. The width of the window used for this moving average is preferably about two minutes but may be selectable between much longer periods, e.g., ten minutes, and much smaller periods, e.g., twenty seconds.

Pattern re-detection is performed off-line when the user chooses to do so. Two basic approaches are allowed in re-detection: The first allows the user to select another set of detection criteria from the Knowledge Base; in the second approach, the pattern rules and reference levels of the detection criteria can be adjusted to the particular data of the subject under study. These rules are graphically presented on the output means to the operator, including the rules that apply to the particular pattern being detected as well as the type of reference level used in the case of detecting such conditions as hypopnea and apnea. The rules and the level type that are used can be discarded and new ones chosen using a cursor pointer indicating device, for example, a mouse, which allows the user to graphically point to a select position on the CRT screen. The reference levels used for detection are preferably displayed in conjunction with scattergrams showing analyzed data. In the case of EEG patterns, REMs, and EMG bursts, these scattergrams represent various features of pattern candidates in relation to each other or to the features of the background activity. In the case of hypopnea and apnea, these scattergrams represent actual derived parameters of detected phenomena against both types of reference levels. Adjustment of a reference level is done by dragging a particular reference line on the screen to a desired position on the appropriate axis of a scattergram using the mouse or other pointer. Adjustments of rules and/or levels are typically followed by re-detection of that particular pattern over the entire time of the recording. After inspection of the results and comparison with the original outcome, the new results are accepted or rejected by the user. If rejected, the redetection process may be repeated until acceptable results are obtained.

After detection or re-detection has been accomplished, classification in accordance with the present invention may be performed. In particular, with respect to sleep analysis, sleep and wakefulness may be separated into six classes—awake, REM sleep, and sleep stages I-IV—, and where apnea is analyzed, apnea may be classified into three types—obstructive, central or mixed.

Classification of sleep and wake is done in epochs preferably of 30 seconds duration. The classification consists of a process of checking, consectively for all classes, whether the EEG, EOG and EMG patterns fulfill the criteria that identify one of those classes. If not, the sleep-wake stage of that particular epoch is designated as "undefined".

If the user chooses to do reclassification, it is performed off line with the previously recorded data. Reclassification can follow two basic approaches: the first allows the user to select another set of classification criteria from the Knowledge Base, while the second approach, for each of the aformentioned classes, allows the rules and reference levels of the corresponding classification criteria to be adjusted to the particular characteristics of the polygraphic data being taken from the subject under study. The rules are graphically presented to the user in matrix form: all of the classes aforementioned are on the horizontal axis and all of the possible constituting patterns along the vertical axis. The rules that are used are indicated and the reference levels listed in the corresponding matrix element. The rule used can be discarded and a new one selected using the mouse. In addition, the time period constituting the epoch (e.g., 30 seconds) over which the classification is carried out can be selected to be longer or shorter, e.g., for as long as 2 minutes and as short as 2 seconds. Reference levels for all constituting patterns can be displayed separately for each sleep stage at a time. The reference levels are indicated as horizontal lines in rank curves that show all the values of that pattern over the entire recording time ranked according to magnitude. Relatively long periods of stable sleep, as, for example, stage IV, II and REM, will appear as horizontal plateaus in the monotonically decreasing curves. Adjustment of a reference level can be done by dragging a particular "reference line" to a desired position using the cursor control mouse. Adjustment of a reference level can also be facilitated after using a cursor indication of a certain interval in the trend curves that is typical for a particular sleep stage. The mean values of the relevant patterns over this period is calculated and indicated in the ranks curve to serve as a guideline. Adjustment of rules and/or levels may then be followed by reclassification over the entire time period of the recording. After inspection of the results and comparison with the original classification, the new results can be accepted or rejected by the operator. The automatic classification performed by the system can be overridden by the operator in various ways, as by manipulation of a horizontal cursor over the trend curves that indicate detected artifacts or "motility". In such a case, those epochs in which such a curve exceeds the cursor level are designated as "undefined". Various ways of manual editing of the classification can also be performed by the user, as discussed further below.

Classification of the various types of apnea is carried out over the entire time of recording. It consists of checking, consecutively for all three types of apnea, whether the amplitude and frequency of respiration, the phase angle between the rib cage and abdomen movements, the intercostal EMG, and the position of the body during the detected apnea fulfill the criteria that identify one of the three types of apnea. If these factors do not meet the criteria for any of the three types of apnea the particular detected apnea is designated as "undefined". If the user chooses to do reclassification it is performed off-line using the stored feature data. Two basic approaches are allowed in reclassification: The first allows the user to select another classification criteria from the Knowledge Base, while in the second approach, for each of the three types of apnea the rules and reference levels can be adjusted to the respiratory characteristics of the subject under study. Rules are again graphically presented in a matrix: the three types of apnea are along the horizontal axis with all possible constituting signal parameters along the vertical axis. The rules and actual reference levels that are used are indicated in the corresponding matrix elements. Rules that are used can be discarded and new ones chosen using the mouse. Reference levels for all of the characterizing parameters can be displayed for one type of apnea at a time. The reference levels are indicated in scattergrams that show the value of parameters for the particular type of apnea detected over the entire recorded time in relevant relationship to each other. Adjustment of a reference level can be accomplished by dragging a particular "reference line" to a desired position using the mouse. Adjustment of rules and/or levels is typically followed by reclassification over the entire time of the recording. After inspection of the results and comparison with the original classification, the new results may be accepted or rejected by the operator. The automatic classification can be overridden by the operator by manipulation of a horizontal cursor in the trend curves, for example indicating "motility"; the apnea occuring in those epochs where the curve exceeds the cursor level is then designated as "undefined". Different ways in which manual editing of the apnea classification can be accomplished are described further below.

The system of the present invention also provides for the generation and display of graphical presentations of the combined analysis, in time synchronized relationship, of several physiological functions and variables such as sleep, brain functioning as expressed by the fluctuations of the EEG signals, respiration, cardiac function (e.g. heartrate) nocturnal penile tumescence, and body movement activity level. This synoptical overview provides the clinician with a tool for studying the relationship between the several functions and variables in time correlation. The time span over which a synopsis can be displayed is selectable between a maximum span of, for example, 24 hours, and a minimum span of, for example, 2 hours, to allow a broad range of clinical applications. The effective time resolution of such a synopsis is determined by the time span displayed and the resolution of the screen (for example, 2 hours corresponds to 7.5 seconds, 24 hours to 1.5 minutes, etc.). In the preferred embodiment, the synopsis shows the results of the classification of sleep into stages and of detected anpea into different types in combination with the patterns and variables that constitute the classification. This display format first serves the purpose of showing relevant information which is possibly lost in the process of classification. Second, it provides the necessary means for quality assessment of the classification and for a global quality assessment of the detection of patterns. This assesment can be done by the clinician by visual inspection of the relationship between the detected patterns. For example, sleepspindles are probably erroneously detected if there are simultaneously detected high frequency artifacts and if the muscle tension is high.

In the preferred embodiment of the invention, such a synopis presents values of some or all of the following parameters or variables averaged over a time interval which is a function of the resolution: (a) the classification of sleep in terms of the hypnogram; (b) the number of detected rapid eye movements; (c) the amplitude of EMG, derived from the chin; (d) the amplitude of "motility" measured using an accelerometer; (e) time duration of detected artifacts (3 types are preferably indicated using different colors for low frequency, high frequency, and broad-band artifacts); (f) the amplitude and frequency of the classical EEG background rhythms in combination with detected patterns such as K-complexes, theta and alpha bursts and sleepsplindles; these EEG phenomena are indicated for four EEG channels in one display that preferably shows two times the parameters for two averaged channels in a mirrored fashion; (g) the time duration of EMG bursts occuring in both legs, displayed in a mirror image fashion; (h) the time duration of detected hypopnea and apnea, with the color of the apnea displayed to the operator preferably indicating the type of apnea; (i) minimum/maximum values per 30 second epoch of the (averaged) amplitude of rib cage and abdomen movements; (j) minimum/maximum values of the (averaged) frequency of rib cage and abdomen movements; (k) minimum/maximum value of the phase angle between rib cage and abdomen movements; (l) minimum/maximum values of the repetition frequency of the intercostal EMG bursts; (m) oxygen and carbon dioxide saturation levels; and (n) minimum/maximum values of heart rate.

In accordance with the invention, it is also possible to provide, both during recording and real time analysis, on line (real time) synoptical display of the analysis results which are computed on an updated basis from the start of the analysis. For one subject, the synoptical display may be presented in a dual-timebase fashion, with a break point between the connected timebases at 50% of the width of the display. On the left side of the break point the synoptical display of the earlier portion of the analysis (that occuring since the beginning of the analysis) is presented at a timebase that is common for the interpretation of long term (circadian and ultradian) flucuations. This "standard" timebase is selectable between, for example, 2 and 24 hours, with a nominal selection of 8 hours. This corresponds to an analysis resolution between 15 seconds and 30 minutes, with a nominal resolution of 1 minute. On the right hand side of the break point, the synoptical display of the most recent analysis results are presented on a time base that allows for the interpretation of short and medium term fluctuations. This "expanded" timebase is selectable between 0.5 and 120 minutes, with a nominal selection of 15 minutes. This corresponds to an analysis resolution between 0.0625 and 15 seconds, respectively, with a nominal resolution of about 2 seconds. The most recent analysis results are displayed at the extreme right hand side of the expanded time base. Every epoch (e.g., every 30 seconds) new points that originate from the on-line analysis are added to the curves which constitute the synoptical display for the most recent past. All points in the expanded timebase are shifted to the left to accommodate the new points. The points that are shifted over the break point between the expanded and standard timebase are then integrated into the standard timebase, which then also shifts to the left but at a slower pace. This special display method allows for on-line trending of short term and long term phenomena in any of the displayed analysis results and for on-line monitoring of the most recent analysis results. If the analysis is terminated, the synoptical results can be redisplayed at the standard timebase over the full width of the display screen; a nominal selection of, for example, 8 hours now corresponds to a resolution of 30 seconds.

During the foregoing analysis and on-line trending, a point in time can be indicated in the standard timebase after activation of a so called "zoom" function. This function will redisplay the synoptical analysis results around the indicated point using an expanded timebase selected for synoptical display of the most recent past. The expanded timebase synoptical results now displayed are positioned at the left hand side of the break point between the standard and expanded timebase and will largely obscure the synoptical results displayed at the standard timebase. Because this function allows for the temporary expansion (zoom) of the earlier synoptical analysis results to the same timebase as used for the synoptical results of the most recent past, direct comparison between the two is possible. Termination of the "zoom" function will restore the original synoptical display of the earlier analysis results in the standard timebase.

During recording and on-line analysis, any subject connected to the analyzer can be selected at any time for on-line trending and monitoring as described above. After selection of another subject for trending, the synoptical display of the analysis results is built up in the dual-timebase format previously described. Immediately after selection, new points are added every epoch (30 seconds) to the most recent past as they become available.

The invention also allows for the trending and monitoring of multiple subjects simultaneously. For simultaneous trending of two subjects, the total display screen is vertically divided into two (half width, full height) windows. For simultaneous trending of up to four subjects, the total display screen is divided into four (half width, half height) windows. In each of these windows a synoptical display of the analysis results of a single subject is displayed. Each synopsis is displayed in a single timebase fashion. The nominal timebase is 8 hours but is selectable to other timebases, independently for each subject. Depending on the selected timebase, each synopsis is updated with the points from the on-line analysis as they become available. Again, each synopsis will shift to the left during entry of new data, the most recent analysis results being displayed at the right hand side of each portion of the screen. This function also allows for simultaneous multi-subject trending and monitoring with a user interactive selectable resolution.

In another aspect of the invention, following the recording of the initial analysis it is possible to provide a synoptical display over the full timebase at the left hand side of the screen and over a short timebase at the right hand side after activation of the so called Zoom mode. Zoom allows for indication of a point in time on a full timebase followed by retrieval of analyzed data around the indicated moment. After averaging of the analyzed data over an interval that corresponds with the screen resolution (x-direction) these averaged analyzed data are displayed. The time span is selectable between 120 minutes and 30 seconds and the corresponding time resolution (thus the interval for time averaging) is between 15 seconds and 0.0625 seconds, respectively. In this manner, the system of the invention may be used as a tool for visual exploration by the user of the analysis because a more detailed study of the relationships between variables is available then from a full timebase synopsis. Second, short term fluctuations of a particular physiological function or variable (e.g., periodic breathing with a cycle period in the order of minutes) can be studied by optimal matching of the timebase. Relevant short lasting phenomena can also be traced by matching the appropriate time resolution (e.g., a timebase of 10 minutes corresponds to a resolution of about 2 seconds, which is sufficient to reveal the individual EEG patterns seen during a microarousal). In this regard, the invention allows a quality assessment of the pattern detection after choosing an appropriate time resolution that reveals the individual detected patterns.

As a further feature, following the above described recording and analysis, synoptical display may be provided over the full timebase at the left hand side of the screen and display of raw data may be provided at the right hand side of the screen after activation of a so called "Raw" function. The function "Raw" allows indication of a point in time on the full timebase followed by retrieval of raw data gathered adjacent to the indicated moment in time and display of the data over a time span selectable between 120 seconds and 5 seconds (the corresponding bandwidth is about 1.5 Hertz and 35 Hertz respectively). In the preferred embodiment the "Raw" function is activated in a sequence following activation of the above described "Zoom" function. At that time, the right hand side of the screen is already occupied and the raw data will be displayed at the left. The raw data on the left hand side will obscure part of the full timebase synopsis except for the hypnogram. As a result, the screen shows a combination of (a) long term fluctuations in terms of the hypnogram, (b) short term fluctuations in the "Zoom" synoptical display, and (c) corresponding raw data. This display feature provides a tool to the clinician for ultimate and complete visual exploration of the recorded data with focus on the study of the outcome of the automated analysis and its relationship with the raw data. The actual moment in time over which the raw data are displayed is indicated in both short and full timebasis synopses (the hypnogram), thereby serving to orient the user in time. This aspect of the invention also serves as a tool for a complete quality assessment of the detection of patterns. After matching the timebase of the "Zoom" and "Raw" displays (e.g., 30 seconds) a one-to-one comparision is possible. Finally, for a selected epoch the "Raw" function can be used for manual editing of the ultimate classification.

The invention also allows a user to define the layout of the synopsis. In this regard, the user has great flexibility in tailoring the synopsis to the particular clinical application. This aspect of the invention allows selection of the number and order of displayed variables in three main catagories, namely sleep/wake, respiration and remaining variables. A minimum set of variables to be displayed for sleep/wake includes the following:

(a) the hypnogram, (b) occurance and duration of artifacts, and (c) a single channel of EEG variables, averaged over the available EEG channels.

A maximum set of displayed variables can include the following:

(a) the hypnogram, (b) the number of detected REMs, (c) the amplitude of EMG derived from the chin, (d) the amplitude of "motifity", (e) the occurance of artifacts (3 types, preferably indicated with different colors), (f) an individual display of analyzed EEG taken from up to 8 channels of EEG signals to reveal distribution over the scalp, and (g) a display of amplitude and burst activity in up to 4 channels of EMG activity.

The minimum number of variables to be displayed for respiration is none. A maximum set can constitute the following: (a) time duration of selected hypopnea and apnea, the latter classified according to type of apnea, (b) amplitude and frequency of up to 4 channels or oral and nostril air flow, rib cage and abdomen movements, (c) phase angle between rib cage and abdomen movements, (d) repetition frequency of detected intercostal EMG bursts, (e) oxygen and carbon dioxide saturation levels, (f) body position indication, and (g) sound.

The minimum set of remaining variables to be displayed is none. Variables that may be included are among others, the following: (a) heart rate, (b) up to 4 variables related to the measurement of penile tumescence, (c) body movement activity, and (d) misceleanous.

The system in accordance with the invention also provides a compact display of amplitude and frequency characteristics of a variety of EEG phenomena which vary over time. Assuming that the horizontal axis display corresponds to time, the vertical positive axis can correspond to amplitude and number of detected transient patterns within a time interval corresponding to the display resolution. The negative vertical axis can correspond to frequency. Up to 5 frequency areas can be displayed in a linear fashion; that is, the various areas can range from 0 to 5 Hertz, from 5 to 10 Hertz, etc. Also the variations can be formed in a semi-logarithmic fashion, for example, the consecutive areas going from 0.5 to 1 Hertz, from 1 to 2 Hertz, from 2 to 4 Hertz, and so forth. Inside the various frequency areas of the semi-logarithmic presentation, the scale can be made linear to ease the burden of interpertation. Different colors are preferably used for the display background activites and patterns occuring in the various classical EEG frequency bands. Furthermore, a differentiation is made in the display of the background activities and the separately detected transient patterns.

The amplitude of the background activity is indicated using a special type of histogram display. First, for each of the classical frequency bands there is a lower threshold value that can be modified by the user. The bottom portion of the histogram-bar to be drawn corresponds to the actual frequency plus the threshold. The top position of the histogram-bar corresponds to the actual amplitude. While drawing the bar, the saturation of the color preferably increases as the length of the bar increases in direct proportion with the amplitude. The frequency of the background activity is indicated with a dot having the appropriate color and a saturation that corresponds to the amplitude. As a result of this method of display, a minimal redundancy is created; that is, as the amplitude of a certain background rhythm decreases, it gradually vanishes and so does the dot line indicating the corresponding frequency.

Display of transient patterns is differentiated according to the time resolution that is used. If the interval time exceeds the time duration of a particular pattern, then the number of patterns within each such interval is indicated using a regular hystogram display. The bottom portion of the bar corresponds to the (mean) frequency of the pattern or patterns in the interval, and the length corresponds to the number of patterns per interval. If, on the contrary, the interval time of the resolution is shorter than the duration of a particular pattern, then its actual amplitude is indicated using a histogram display alternating between two saturation levels of the particular color chosen for the display. The bottom position histogram-bar corresponds to the actual frequency and the length of the bar to the actual amplitude.

The various EEG channels can be displayed individually or combined together. If they are combined together, it is possible to have mirror-wise display of 2 channels and/or the possibilty of ensemble averaging of the analyzed data over an indicated EEG channel prior to regular or mirror-wise display.

In the preferred embodiment 4 EEG channels are displayed in a 2 by 2 mirror-wise fashion. Four frequency areas are displayed in a semi-logrithmic fashion, going from 1 to 16 Hertz (i.e., from 1 to 2 Hertz, from 2 to 4 Hertz, etc.). The color for delta waves is preferably blue, for theta—purple, for alpha—red, for beta preferably yellow (or possibly for sigma/sleepspindle) and for beta 2—preferably white.

In another aspect of the invention, following the recording and possible initial analysis of data, the invention allows for an interactive visual inspection of the raw input data which constitute the poly(somno)-graphic recording from an individual subject. A so called "Scan" function displays all input variables that were involved in the recording procedure on the graphics display screen simultaneously. The ordering of input channels is the same as that during the recording, and the general format simulates a recording on paper. The timebase that corresponds with the full width of the screen is selectable, as is the vertical display gain. The raw input data on the screen can be updated in either a "page" or "scroll" mode. In the "page" mode the data are displayed on the screen in a static fashion. After some selected period of time, the data are replaced instantaneously with the data on the next "page". In the "scroll" mode, the raw input data are moving on the screen with a constant velocity in the horizontal direction, emulating recording on a standard paper feeding recorder. The speed by which pages are updated or at which the data are scrolling by is determined by the selected timebase and a graphic speed control function. The "real-time updates speed" is equal to the selected time base. If the selected timebase is, for example, 30 seconds, then a screen in any either page or scroll mode is completely replaced every 30 seconds. The speed control function provides for an instantaneous user interactive control of the factor at which the speed of the screen updates or is increased or decreased with respect to the real-time update speed. If, for example, a factor of 4 is selected with a timebase of 30 seconds, then the screen is completely refreshed every 7.5 seconds in either the page or scroll mode. The speed control has a speed factor range between 0 and 64 and also allows instantaneous selection of the update selection.

This implies that the raw data can be inspected with instantanous control of scannings in either the forward or backward direction. The scanning can be paused and continued at any time. Event messages can be tagged onto the waveforms at an arbitrary point in time and a hard copy can be initiated anytime.

A "Search" function allows the user to find moments or events in the raw data file under the control of the master program. One option provided is specification of a "time during recording"; the function will then search for that moment and display the corresponding raw input data. Another available option is searching for the raw data with which an event message was associated. Many additional options exist if the raw data are already analyzed, as they typically are. In that case, the hypnogram is displayed on the screen as well and the time instance of the currently displayed raw data is indicated on the time axis of the hypnogram. An option for the "search" function which is then presented is the ability to indicate with the graphic cursor a point in the hypnogram, after which the corresponding raw data are searched and displayed. Another option is the search for the occurance of detected patterns, such as, for example, the sleepspindle. Another option is a search for the occurance of a certain classification as, for example, the onset of the next REM-sleep period.

In another aspect of the invention, following recording and initial analysis, the system allows interactive visual exploration of the analysis results in relation to the raw input data which constituted the poly (somno)-graphic recording from a subject. The so-called "Scan" function displays all input channels that were involved in the recording and subsequent analysis on the graphics display screen simultaneously. The ordering of input channels is the same as during the recording, and the general format simulates a recording on paper. The timebase that corresponds with the full width of the screen is selectable, as is the vertical display gain.

The raw input data on the screen can be updated in either a "page" or "scroll" mode. In the "page" mode the data are displayed on the screen in a static fashion. After a selected period of time, the data are replaced instantanously with the data on the next "page". In the "scroll" mode, the raw input data are moving on the screen with a constant velocity in the horizontal direction, emulating recording on a standard paper feeding recorder.

Assuming that an analysis was done on the raw data, the "Scan" function has an option in which detected patterns may be indicated in the raw data display. With this option, the detected patterns, for example K-complexes or sleepspindles, are highlighted with respect to the background as they appear on the screen in either the page or scroll mode. This option provides the ultimate quality check as to whether the detection criteria are appropriate, as it allows a judgment by the user of both false-positive and false-negative detection errors. It will also show the classification that was determined by the system for the current epoch. These two features thus provide the explanatory aspect of the expert system approach that is embedded in the invention. Another available option allows the manual indication of patterns and a manual determination of the classification for the currently displayed epoch. This can be done to overrule part of a previous (automated) analysis, for example, detection plus classification. In the hypnogram or apnea classification curve of the final synoptical display, these overruling classifications are distingushed by a special color indication.

Manual indication of patterns and classifications can also serve as a supervised learning mode to establish new criteria which are available to the system. If done for a certain class of subjects, in combination with the internal data base management system the user can establish new analysis criteria matched to the class under study. After the new criteria are added to the Knowledge Base they can be used on a routine basis thereafter. Criteria for nonstandard patterns found in a particular recording can be easily established this way. This feature thus serves as an alternative to the regular a priorispecification of patterns, in which the patterns are described ahead of time in terms of minimum/maximum amplitude, frequency, time duration, and so forth.

Further objects, features and advantages of the invention will be apparent from the following detailed description when taken in conjunction with the accompanying drawings.

BRIEF DESCRIPTION OF THE DRAWINGS

FIGS. 8A and 8B illustrate the manner in which the cut-off and center frequencies of a band filter are determined.

FIGS. 13A-13D are graphs illustrating the manner in which an adaptive threshold is estimated from a time series for discrimination between stationary background and foreground transient pattern candidates.

FIG. 18 illustrates the display provided to an operator by the analysis system which shows the detection rules for a particular EEG pattern.

FIG. 23 shows a display provided to the operator by the analysis system of the emulated Reclitschaffen and Kales rules for the classification of sleep.

FIG. 29 is a display provided by the analysis system to the operator illustrating the classification rules for the various types of apnea.

DESCRIPTION OF THE PREFERRED EMBODIMENT

Figure 1:
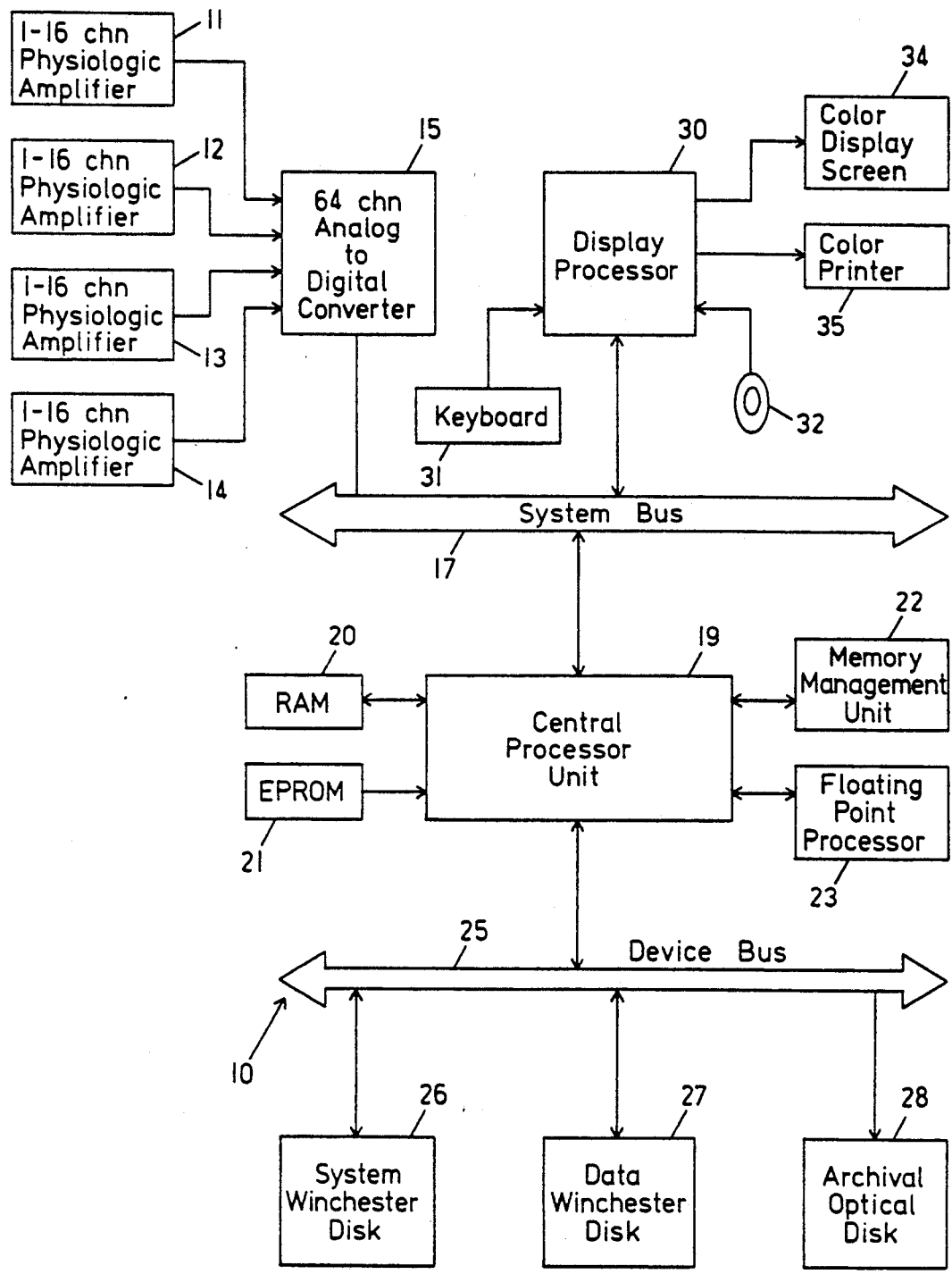
FIG. 1 is a schematic block diagram of the functional hardware components forming the system for analysis of long term physiological recordings in accordance with the invention.

The functional hardware components of a preferred embodiment of the system for analysis of long term physiological polygraphic recordings is shown generally at 10 in block diagram form in FIG. 1. The system 10 receives input data from several channels, which can include input data received by monitoring multiple channels from several patients, through several physiologic amplifiers, four amplifier sets 11-14 being shown in FIG. 1. The amplified and conditioned output signals from the physiological amplifiers 11-14 (e.g., Nicolet 1A96 electroencephalograph amplifiers) are provided to a multiple input channel analog to digital converter 15 (64 channels shown) (e.g., Burr-Brown MPV 906) which converts the analog input signals from the amplifiers to digital data which are transmitted over a system bus 17 (e.g., VME bus), of any standard configuration having sufficient bit capacity, preferably 16 bit or higher. A central processing unit 19 (e.g., Motorola MC 68020) is connected to the system bus and has associated therewith a random access memory (RAM) 20 and a read only program memory (EPROM) 21, a memory management unit 22, (e.g., Motorola 68851) and a floating point processor 23 (e.g., Motorola 68881), all arranged in conventional configurations and selected from various standard microcomputer components commercially available. The central processing unit 19 is also connected to a multi bit bus 25 (e.g., SCSI) which allows reading and writing of data from the central processor unit to various long term storage devices including a system disk 26 (e.g., Quantum Q204), a data disk 27 (e.g., Martor 4380), and a high density optical write once-read many archival disk 28 (e.g., Martor RXT-8005). The system bus is also connected to an input/output and display processor 30 (e.g., Nicolet BDP) which receives user input from a keyboard 31 and a cursor pointer device 32 such as a "mouse". The display processor controls graphics output information supplied to a color display CRT screen 34 (e.g., Hitachi HM4119) and a color printer 35 (e.g., Tektronix 4696). The system controller composed of the central processor unit 19 with associated memories 20 and 21 and the memory management unit 22 and floating point processor 23 control the acceptance of data from the physiological signal sources through the physiologic amplifiers 11-14 and from the user provided input from the keyboard 31 and mouse 32, and provide output information to the user through the display processor 30 to the color display CRT screen 34 and/or the color printer 35. The system program determines the manner of operation of the controller and the manner in which the physiologic data and the user inputs are translated to user communication information. The hardware components set forth in FIG. 1 are of standard design and well known in the art.

Figure 2:
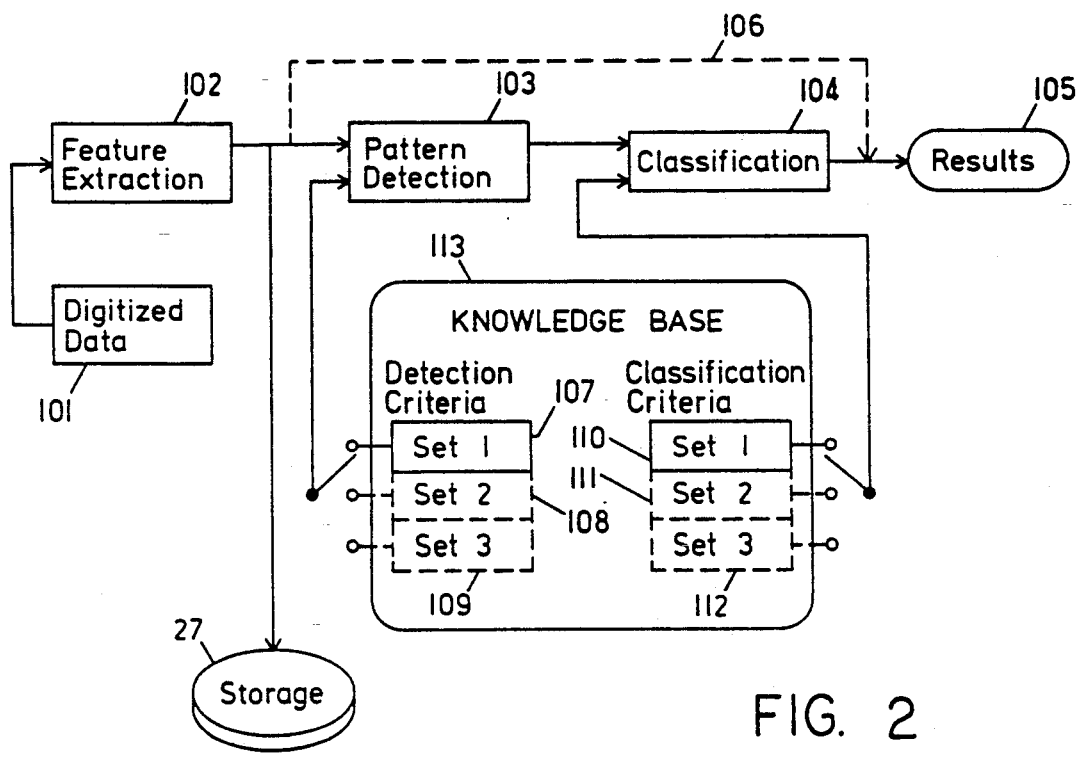
FIG. 2 is a block diagram showing the organization of the real time data processing in the analysis system.

The basic three steps of data reduction that are carried out by the system 10 during real time analysis are illustrated in block diagram form in FIG. 2. The digitized data 101 provided from the A to D converter 15 is operated upon, in turn, by feature extraction 102, pattern detection 103, and classification 104 to provide the final results 105 which are to be displayed to the user. For some variables, only extraction of features is necessary and these are diverted by a branch 106 and directly become part of the results. To carry out the procedures of pattern detection and classification, sets of criteria for detection 107-110 and classification 108-112 are needed. These may comprise a single set or the multiple sets illustrated. All of these sets form the so-called Knowledge Base 113 of the analyzer. The Knowledge Base comprises information that is stored on a long term storage unit for the system, such as the system Winchester disk 26 illustrated in FIG. 1. In addition to the real time processing that is carried out on the data following feature extraction, all of the extracted features are also stored on the data disk 27 for recall later. Prior to the initiation of analysis, the user may pre-select which of the sets of detection criteria are to be used and which of the sets of classification criteria are to be used, and these sets will then be fixed for use during the pattern detection and classification procedures during real-time processing.

Figure 3:
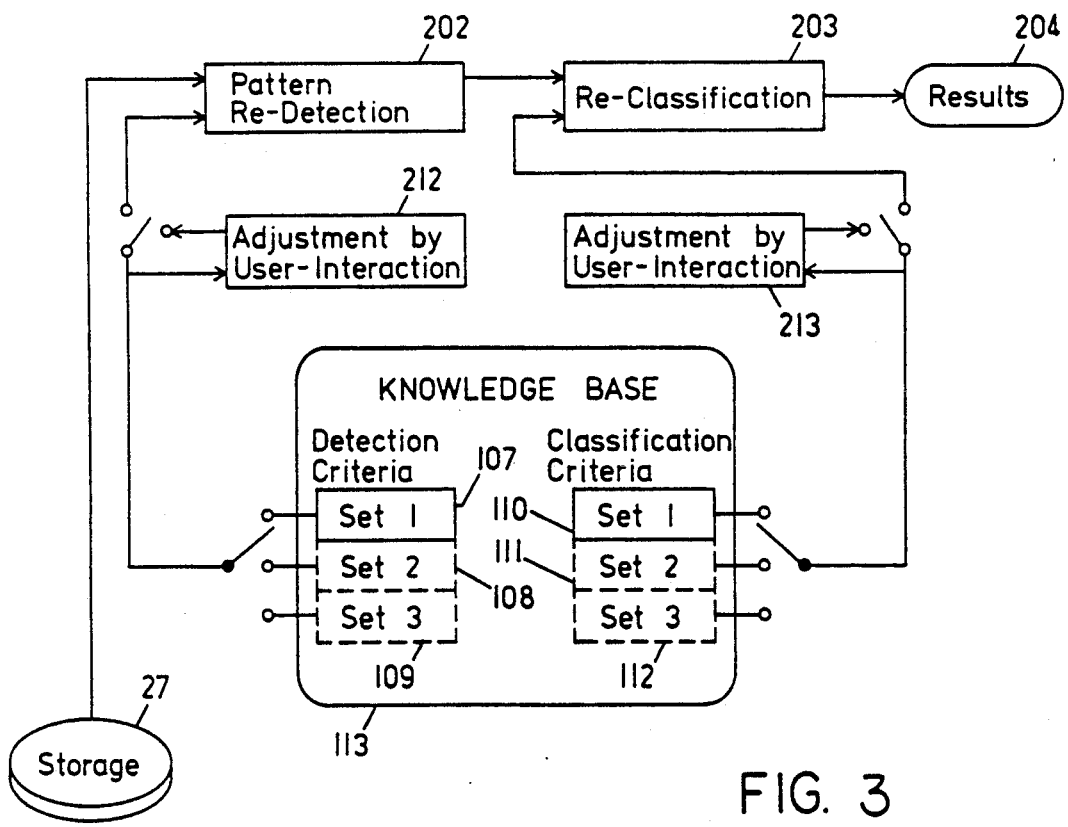
FIG. 3 is a block diagram showing the organization of the off-line interactive reanalysis of data in the analysis system.
Figure 4:
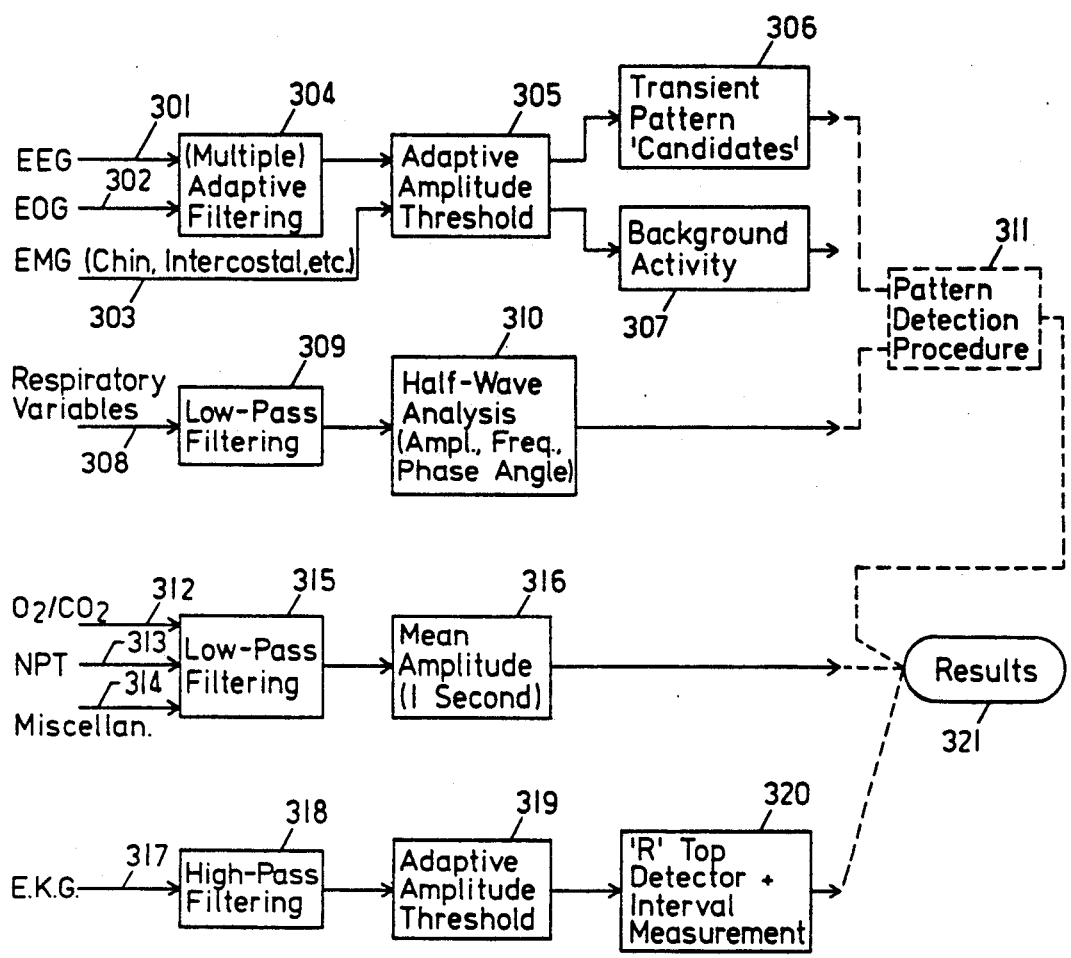
FIG. 4 is a block diagram showing the various steps in the extraction of features from the several input signals.

As illustrated in block diagram form in FIG. 3, the features stored on the storage device 27 may be subjected to re-analysis consisting of re-detection 202 of one or more patterns and/or reclassification 203 to provide more appropriate results 204. Re-analysis can be accomplished after selection by the user of a different one of the sets of detection criteria 107-109 and/or a different one of the sets of classification criteria 110-112 in the Knowledge Base 113. Detection criteria can be adjusted by a user interaction input 212 and adjustment of classification criteria can similarly be made by user interaction input 213.

Although the present analysis system is adapted to analyze a variety of signals picked up by physiological sensors, it is particularly suited to the analysis of those signals commonly encountered in examining the sleep-/awake state of a subject. FIG. 3 illustrates in block diagram form the various steps involved in the extraction of features from the various types of physiologic input signals commonly utilized in sleep/awake research. The EEG signals 301 (digital data streams corresponding to the multiple channel EEG input signals) are filtered in an adaptive manner 304 several times using a filter bank consisting of 5 band pass filters that adapt to the properties of the signals, done on an epoch by epoch basis (e.g., every 30 seconds) and preferably by processing two EEG channels in parallel. Depending on the average amplitude of all of the EEG signals coming out of the first band pass filter (corresponding to the delta wave portion of the EEG signals), the cut-off frequency of the high pass filter for the EOG signals 302 is selected to vary between 2.5 and 7.5 Hertz, corresponding to approximately 20 and 75 microvolts averaged amplitude of the delta waves, respectively. The EMG signal 303 is not filtered. However, the EEG, EOG and EMG signals are all subjected to an adaptive threshold procedure 305. For each epoch (e.g. 30 second interval), an amplitude threshold is estimated for each of the above mentioned signals to allow discrimination between so called "transient pattern candidates" 306, which constitute parts of the signal above the threshold, and background activity 307, which are the features below the threshold. The features derived from transient pattern candidates are stored only for the largest transient pattern candidates occuring in an epoch. For EEG signals, the maximum number is preferably 5 for each frequency band, while for EOG the maximum is preferably 10, for EMG derived from the chin and legs the maximum number is also 5, and for intercostal EMG the maximum number is preferably about 50. From the background activity 307 the mean amplitude (and mean frequency in case of band filtered EEG) over the 30 second epoch is calculated. In addition to the variables noted above, respiratory signals 308, other than oxygen and carbon dioxide saturation, and intercostal EMG have a low pass filter operation 309 performed on them using a rectangular finite impulse response (FIR) filter. Half wave analysis 310 is then applied and peak amplitude and frequency—as well as phase angle between the signal that represents rib cage and abdomen movements—are calculated. The transient pattern candidates from the EEG, EOG and EMG signals and the respiratory variables, after passing through the half wave analysis, are subjected to a further pattern detection procedure 311. For oxygen and carbon dioxide saturation signals 312, NPT signals 313, and all additional miscellanous low frequency variables 314, the signals are low pass filtered at a step 315 and an operation 316 calculating the mean values of these signals every second is performed. The low pass filtering 315 is preferably carried out using a rectangular FIR filter. After calculation of such mean amplitudes on a second by second basis, the outputs constitute part of the overall results 321 which also include the output of the pattern detection procedure 311. The electrocardiogram (EKG) signal 317 is first high passed filtered 318 using an FIR filter ($-0.25$, $+0.5$, $-0.25$ coupled to a sample frequency of about 70 Hertz) prior to estimation of an adaptive threshold at 319 and subsequent detection of the "R" top portion of the QRST sequence and calculation of interval times between R tops at 320. The minimum, maximum and mean heart rate per 30 second epoch are a direct part of the results 321.

Figure 5:
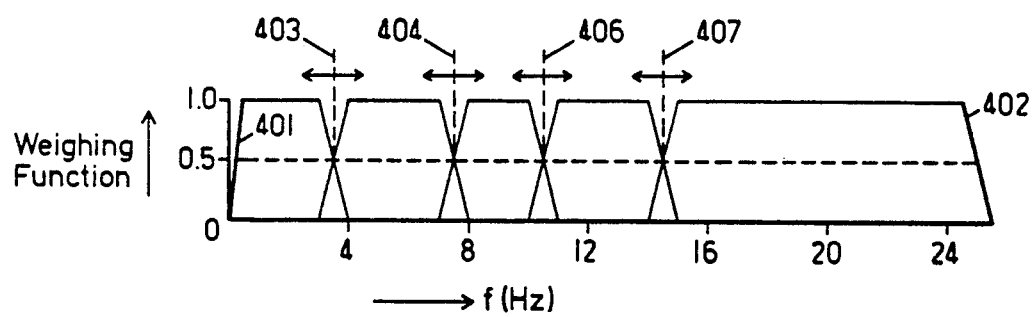
FIG. 5 is an illustrative graph showing the functioning of the adaptive filter bank in the analysis system.
Figure 6:
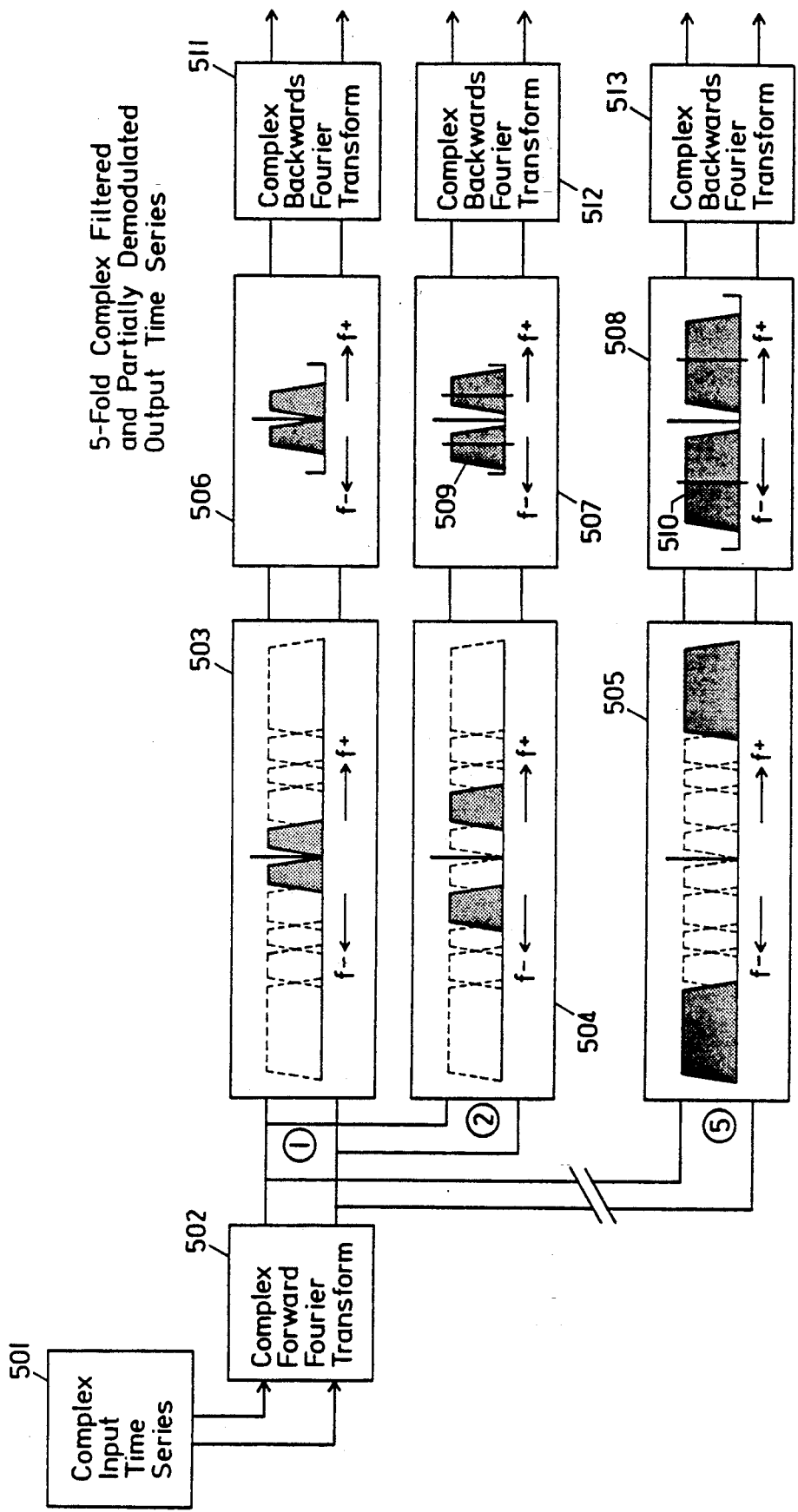
FIG. 6 is a block diagram showing the steps of multiple filtering and partial demodulation of the EEG signal data.
Figure 7:
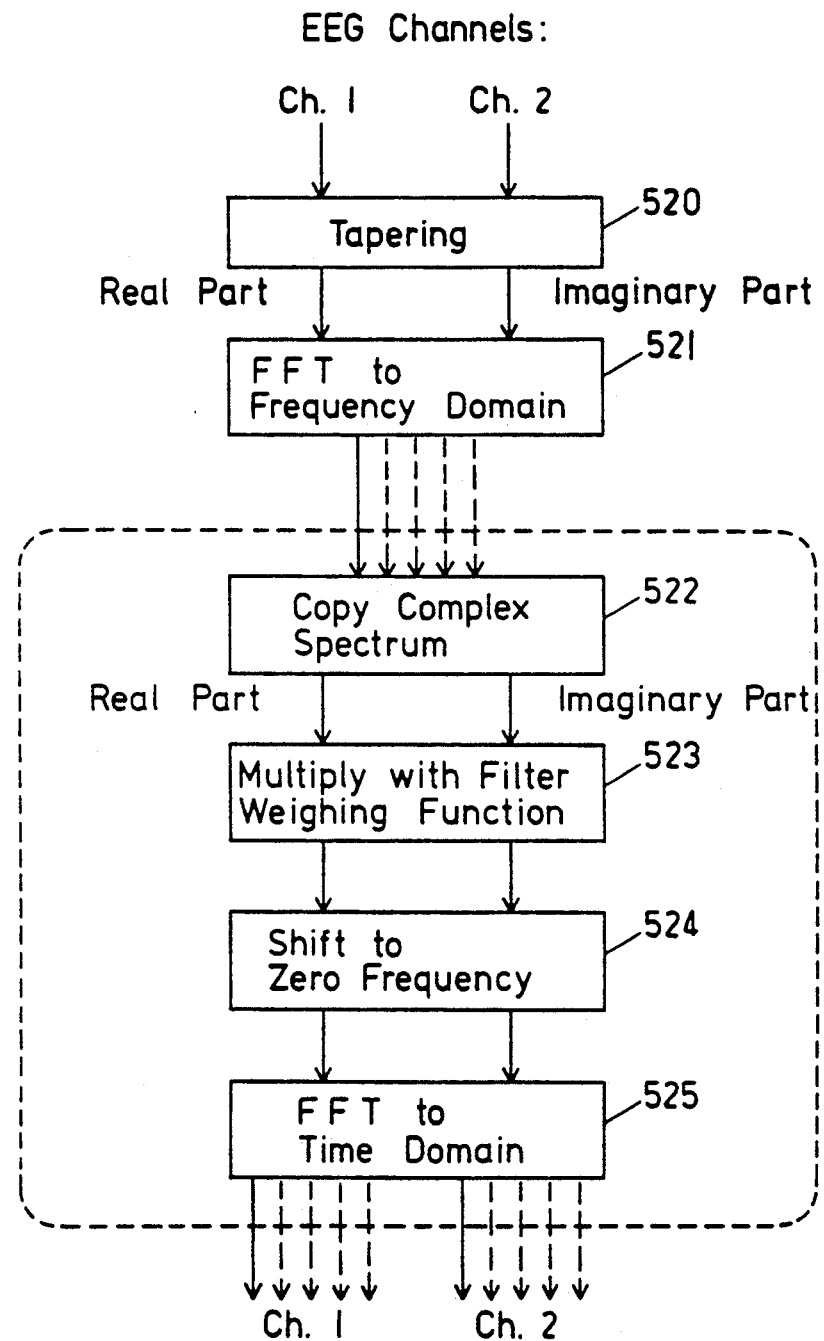
FIG. 7 is a flow diagram showing the operational steps in the 5-fold bandpass filtering and (partial) demodulation performed on th EEG signal data.

The adaptive characteristics of the prefered 5-fold filter bank used for the decomposition of the EEG signals into narrow band components is illustrated in the graph of FIG. 5. The overall bandwidth of the filter bank is user determined before analysis begins. The default cut-frequencies are at the low end, 0.35 Hertz with a linear slope over 0.5 Hertz width 401 (the cut-off frequency is the frequency where the weighting factor is 0.5) and, at the high end 402 at a frequency preferably of 25 Hertz with a linear slope over 1 Hertz. The remaining cut-off frequencies 403–406 illustrated in FIG. 5 can be varied and are updated every epoch of 30 seconds for each (or each pair of) EEG signal. The cut-off frequencies of adjacent filters are equal and correspond to the weighting factor being 0.5. The slopes of the intermediate cut offs are linear and have a width of 1 Hertz. FIG. 6 illustrates the actual epoch-wise 5-fold bandpass filtering and partial demodulation of up to 2 EEG signals in parallel. Where parallel processing of two channels of EEG is carried out, preferably the user will choose leads from identical parts of the brain, that is, e.g., symmetrical leads. The complex input time series data corresponding to the two channels of EEG digitized data are placed in a complex input time series buffer 501 and data therein is subjected to a complex forward Fourier Transform 502 to provide frequency domain output. The filtering begins with a multiplication of the complex output spectrum from the Fourier Transform with the real trapezoid-shaped filter weighting functions (3 of the 5 illustrated) 503, 504, and 505. Partial demodulation is accomplished by shifting the transmitted parts of the spectrum for each filter segment to the zero frequency in operations 506, 507, and 508 over a selected frequency range. Although only three filters are shown in FIG. 6, it is understood that each of the five fold band pass filters would be similarly operated upon. The frequency range over which the partial demodulation is carried out is determined by the number of data subjected to a Inverse Fourier Transform back to the time domain, the smallest number being a power of 2 and covering the desired bandwidth, and by the peak frequency within the band width that is positioned at $\frac{1}{2}$ of the Nyquist frequency (509 and 510 illustrated in FIG. 6) corresponding to the Inverse Fourier Transform. The procedure of partial demodulation is carried out to allow processing; for a regular demodulation is based on the construction of a so-called Hilbert pair that constitutes a signal with the real part of the Fourier Transform and the Hilbert pair (the original signal with a 90° phase shift) in the imaginary part. The positioning of the peak frequencies at half of the Nyquist frequencies is done to maximize the chance that after applying the Inverse Fourier Transform, the signals will be sampled at the moments in time that the peak amplitudes of the half waves occur and when the signals cross the base line. It is noted that a pure sine wave at half the Nyquist frequency corresponds to a time series having the following values: 0, $+1$, 0, $-1$, 0, $+1$, 0, $-1$, etc. The combined procedure of filtering and partial demodulation is completed by applying the Inverse Fourier Transform back to the time domain at 511–513. The parallel processing of signals and the partial demodulation is done in this manner to minimize the processing time. These functions, as performed by the computer controller central processing unit of the system, are shown in flow diagram form in FIG. 7. The input data from the 2 EEG channels is subjected to a tapering operation (520) and split into real and imaginary parts which are subjected to a Fast Fourier Transform procedure to provide frequency domain data (521). The complex spectrum is copied and stored (522), and the real and imaginary parts are multipled with the filter weighting functions (523) and then the real and imaginary parts are shifted to zero frequency (524). The reconstituted frequency domain data is inverse fast Fourier Transformed back to the time domain (block 525).

FIG. 8 illustrates the manner in which the center and cut-off frequencies of a bandpass filter are determined. Where the "signal portion" and "noise" portion power density spectra have the same value, illustrated as at the positions 604 and 605, the weighting-function as chosen equals 0.5 according to the Wiener filter criterion for optimal separation of stationary signal and noise. However, the individual spectra of the "signal" and the "noise" are unknown; only the spectrum of the combined signal plus noise" spectrum illustrated by the shaded area 603 in FIG. 8b is available. In practice, the frequencies corresponding to a chosen weighting factor 0.5 are determined by searching for local minima 606 and 607 in the "signal plus noise" spectrum. For reasons discussed above, the center frequency is positioned in the middle point 608 of the spectrum that will be subjected to Inverse Fourier Transformation back to the time domain.

Figure 9:
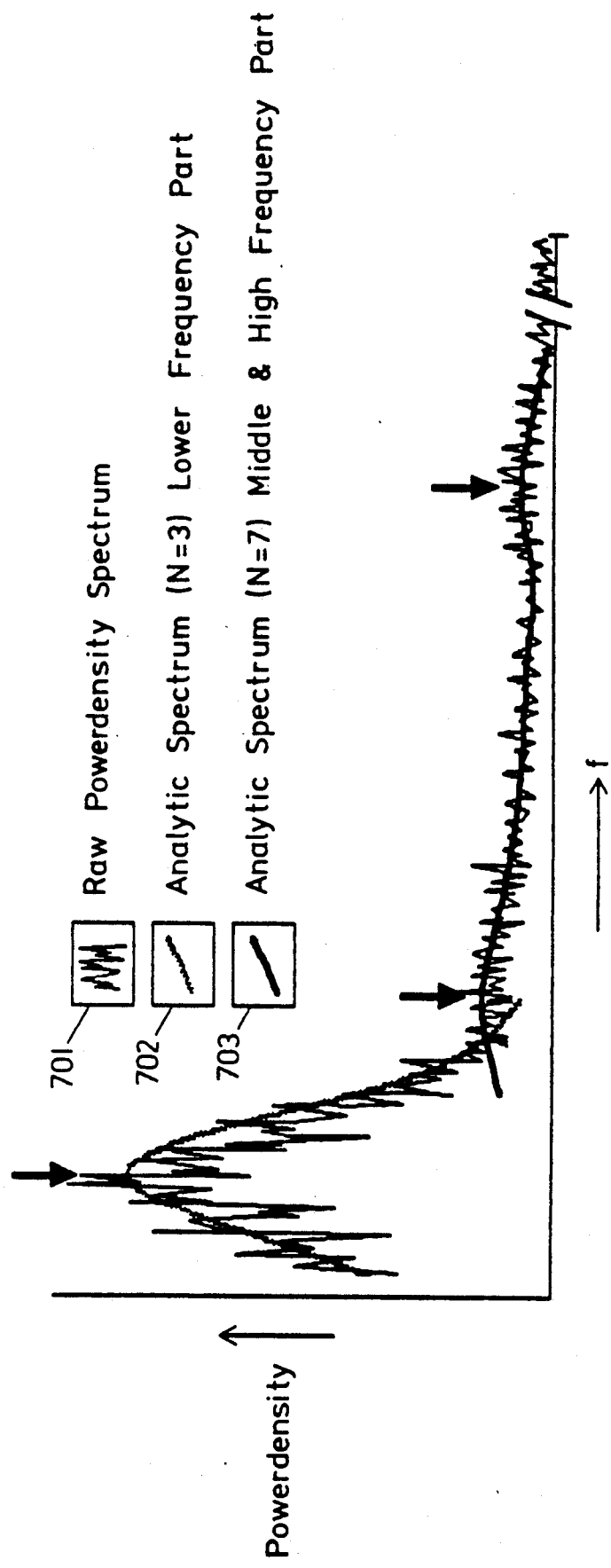
FIG. 9 illustrates the manner in which two analytical spectra are derived from parts of a raw power density spectrum.

FIG. 9 shows the manner in which two analytical spectra designated 702 and 703 are derived from parts of a raw density spectrum 701. Analytic spectra are calculated after solving the Yule-Walker equations based on the auto-correlation function. The auto-correlation function is calculated by Fourier Transformation back to the time domain of a part of the raw power density spectrum. The order of the model for the lower frequency part 702 of the analytic spectrum is 3, to allow for a trailing edge and a peak (delta); for the higher frequency part 703 the order is 7 to allow for a trailing edge and three peaks (theta, alpha and sleepspindle). If the total number of peaks found is not equal to 4, default values are used for the missing peaks or adjustments are made between adjacent filters if one peak is not found.

Figure 10:
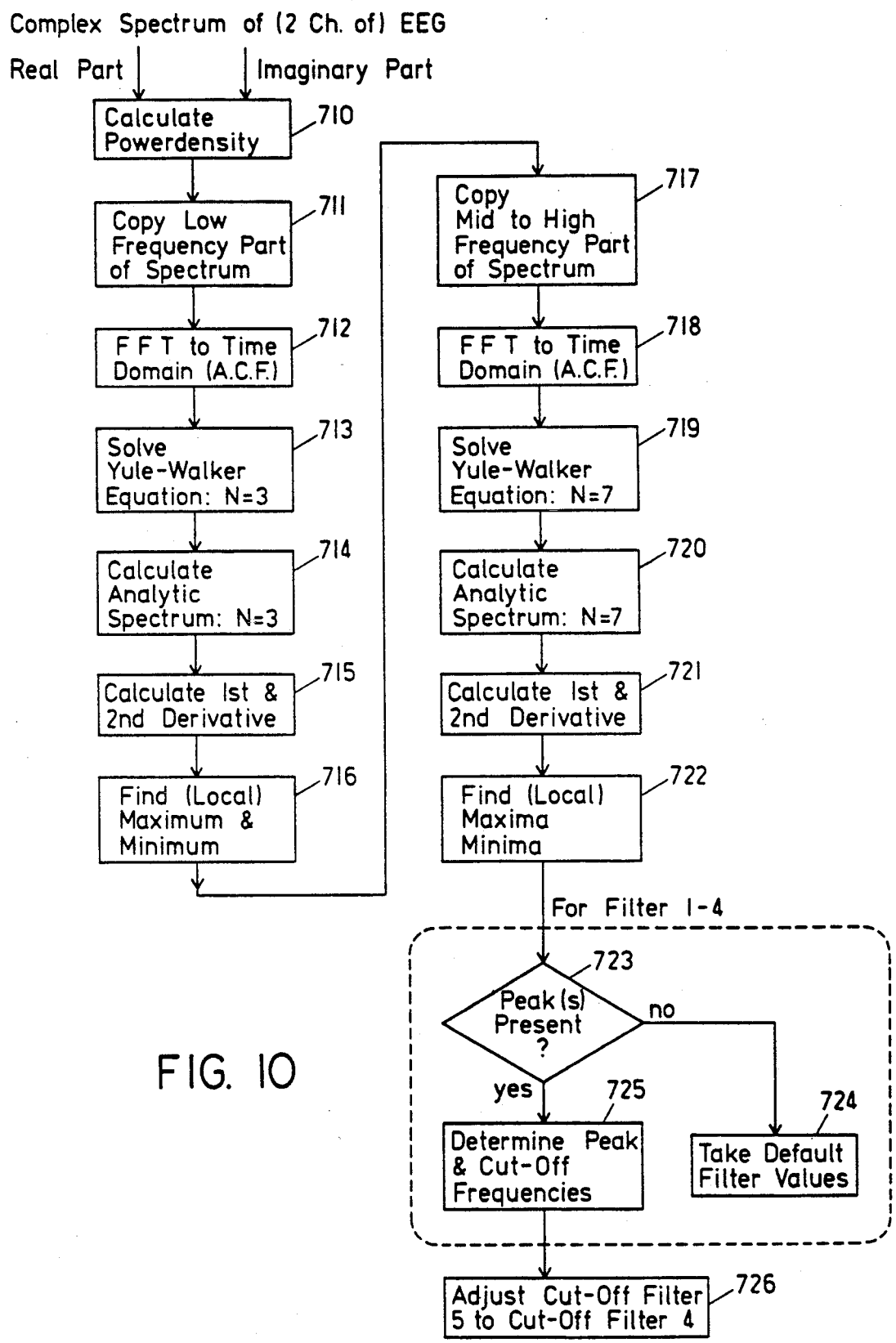
FIG. 10 is a flow diagram showing the steps in the calculation of the adaptive filter bank characteristics.

A flow diagram illustrating the program steps carried out by the computer controller during adaptive filtering is shown in FIG. 10. Taking the calculated complex spectrum of the two channels of EEG signals, the real part and the imaginary part are used to calculate the power density function (710) and the low frequency part of the spectrum is copied (711) and a fast Fourier Transform to the time domain is carried out (712) and an auto-correlation function is performed. The Yule-Walker equation is then solved with N=3 (713) and an analytic spectrum with N=3 is then calculated (714). The first and second derivatives of the calculated analytic spectrum are then determined (715) and the local minima and maxima located (716). The mid to high frequency part of the spectrum is then copied (717) and a fast Fourier Transform to the time domain is then performed (718) and an auto-correlation function computed. The Yule-Walker equation with N=7 is then solved (719) and an analytic spectrum with N=7 is calculated (720). The first and second deratives of the analytic spectrum are then found (721) and this information used in the usual manner to find the local maxima and minima (722). For each of the filters 1 through 4, the program looks to determine whether peaks are present (723); if not, default filter values are used (724). If the peaks are present, the program then determines the peak and cut-off frequencies (725), and when filters 1–4 are completed, the cut-off frequency of the fifth filter is adjusted to the cut off frequency of filter number 4 (726).

Figure 11:
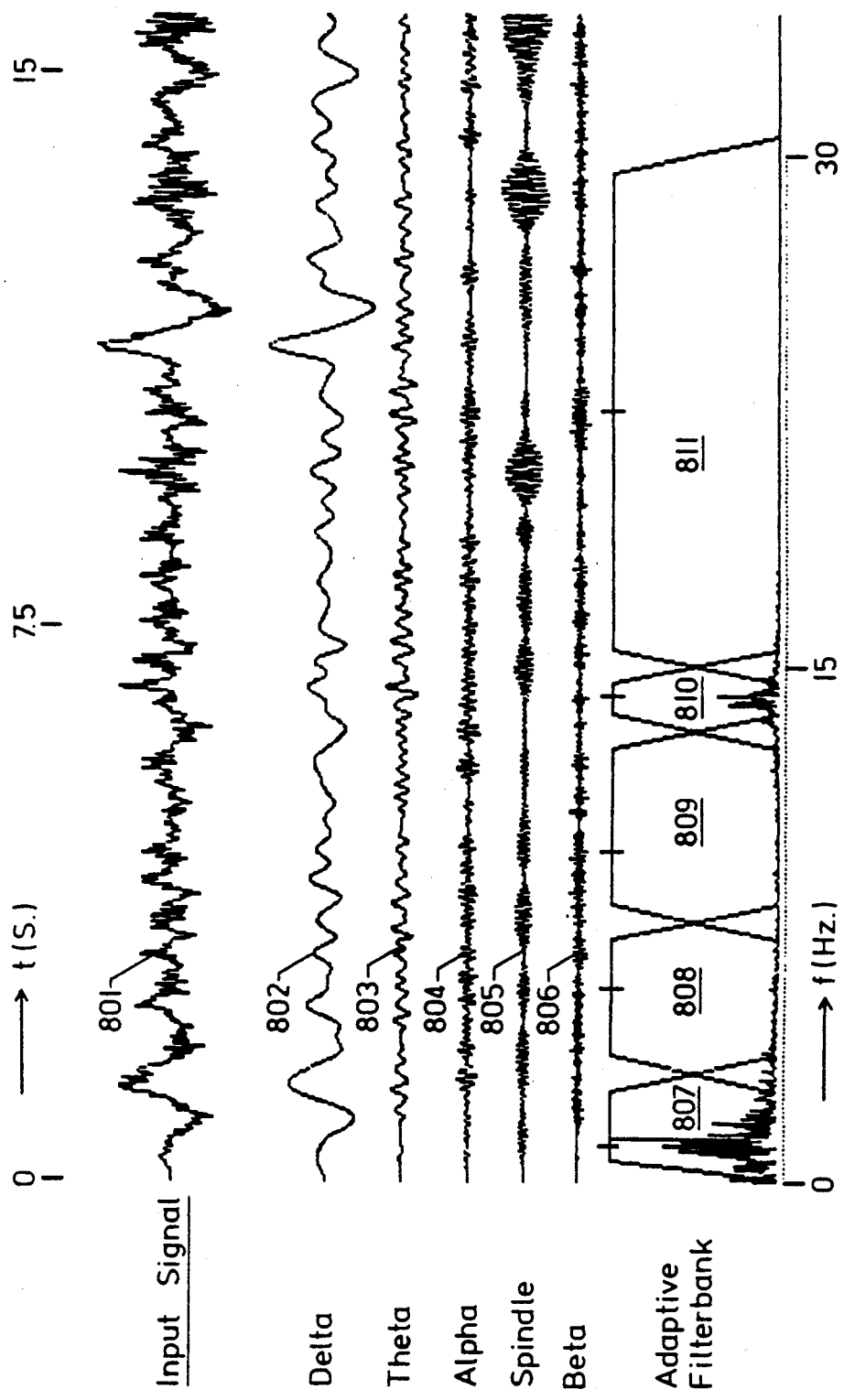
FIG. 11 is a graph showing typical examples of adaptive multiple filtering of an EEG signal.

FIG. 11 illustrates an input signal 801 and the outputs 802–806 of the several filters 807–811 forming the adaptive filter bank characteristics. The fourth filter, designated 810, is centered around the peak frequency of sleepspindles. The high cut-off frequency of the second filter 808 and the low cut-off frequency of the third filter 809 are taken from default filter bank values since there are no peaks in that frequency area.

Figure 12:
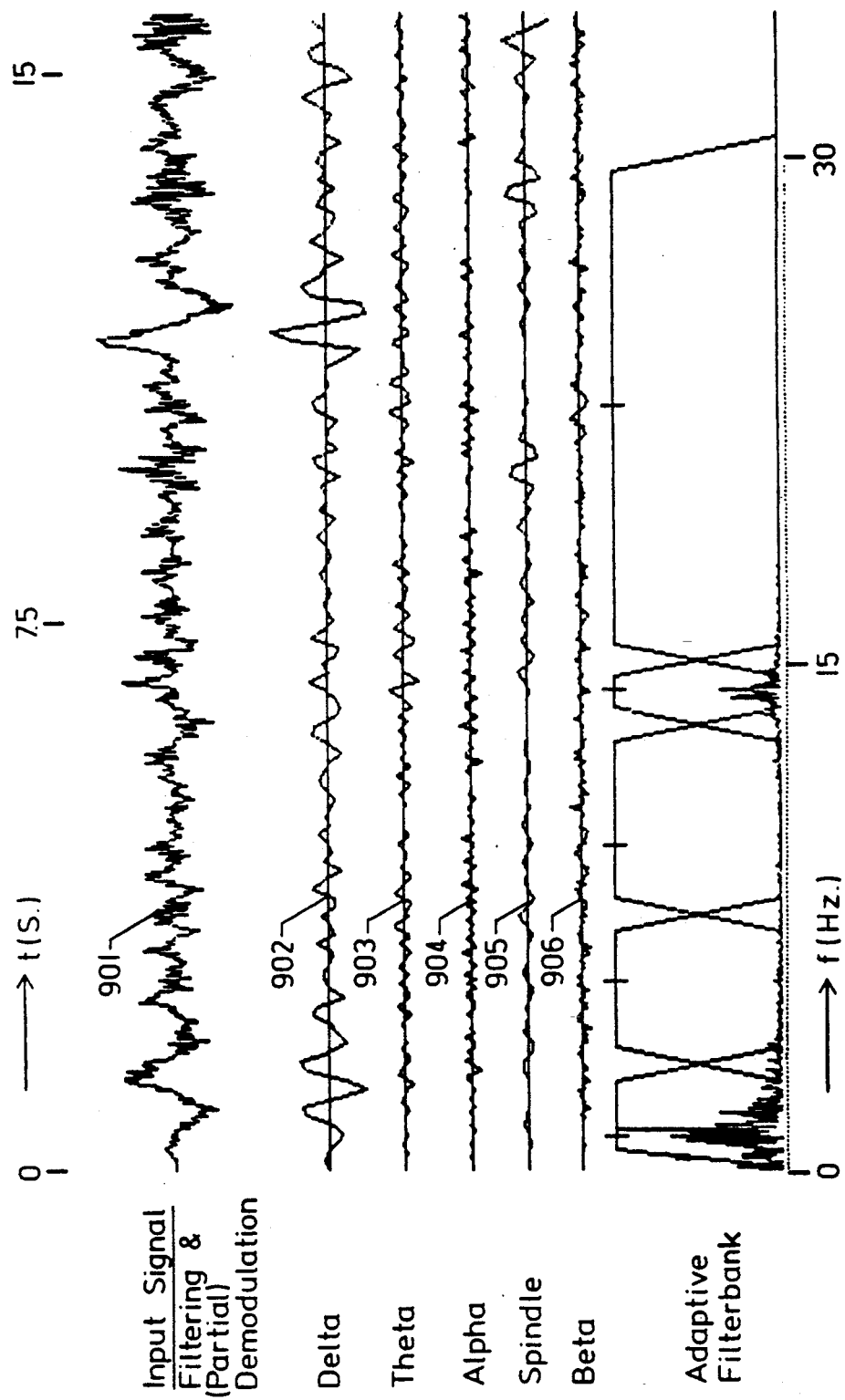
FIG. 12 are graphs showing typical examples of adaptive multiple filtering and partial demodulation of an EEG signal.

FIG. 12 illustrates the effects of combined filtering and partial demodulation applied to the same input signal 901 as displayed in FIG. 11 (the input signal 801). The number of data points needed to describe each of the output signals 902–906 is reduced because of the lower modulation frequency and narrower bandwidth for each of these signals as compared to the situation obtaining in the regular filtering functions 802–806; however, the envelopes for the filter portions are the same in both cases.

FIG. 13 illustrates the manner of operation upon a signal having, as shown in FIG. 13a, a stationary background activity level 1001 and a transient pattern 1002 having a substantially higher amplitude and a shorter duration. Taking the rectified peak amplitudes for all half waves and ranking these according to magnitude results in the sigmoid shaped curve 1003 shown in FIG. 13b for the stationary activity and a curve 1004 with a steep slope for the transient pattern. Adding the two signals 1001 and 1002 results in a rank curve "f(x)" shown at 1005 in FIG. 13c. Detection of the steepest slope portion 1006 and the optimal threshold 1007 for discrimination between transient and background activity can be accomplished by taking the first derivative of "f(x)" and multiplying by −1, resulting in the curve 1008 shown in FIG. 13c, which has maximum value at 1009. However, finding the peak amplitude of the first derivative may give quite inconsistent results when there is no steep slope (that is, no transient). Calculation of the mean amplitude at about 1010 provides a more stable estimate from a statistical view point. For a short lasting transient, the steep slope will be at the left hand side of the curve f(x), the point designated 1005 in FIG. 13c. The aforementioned mean amplitude will be toward the right hand side, thus giving rise to a negatively biased threshold level 1011. The use of such a biased threshold level generally will result in detection of a higher number of false positive transient patterns, as of the type illustrated by the pattern 1012 in FIG. 13d, and a lower number of false negatives as compared to the ideal threshold.

Figure 14:
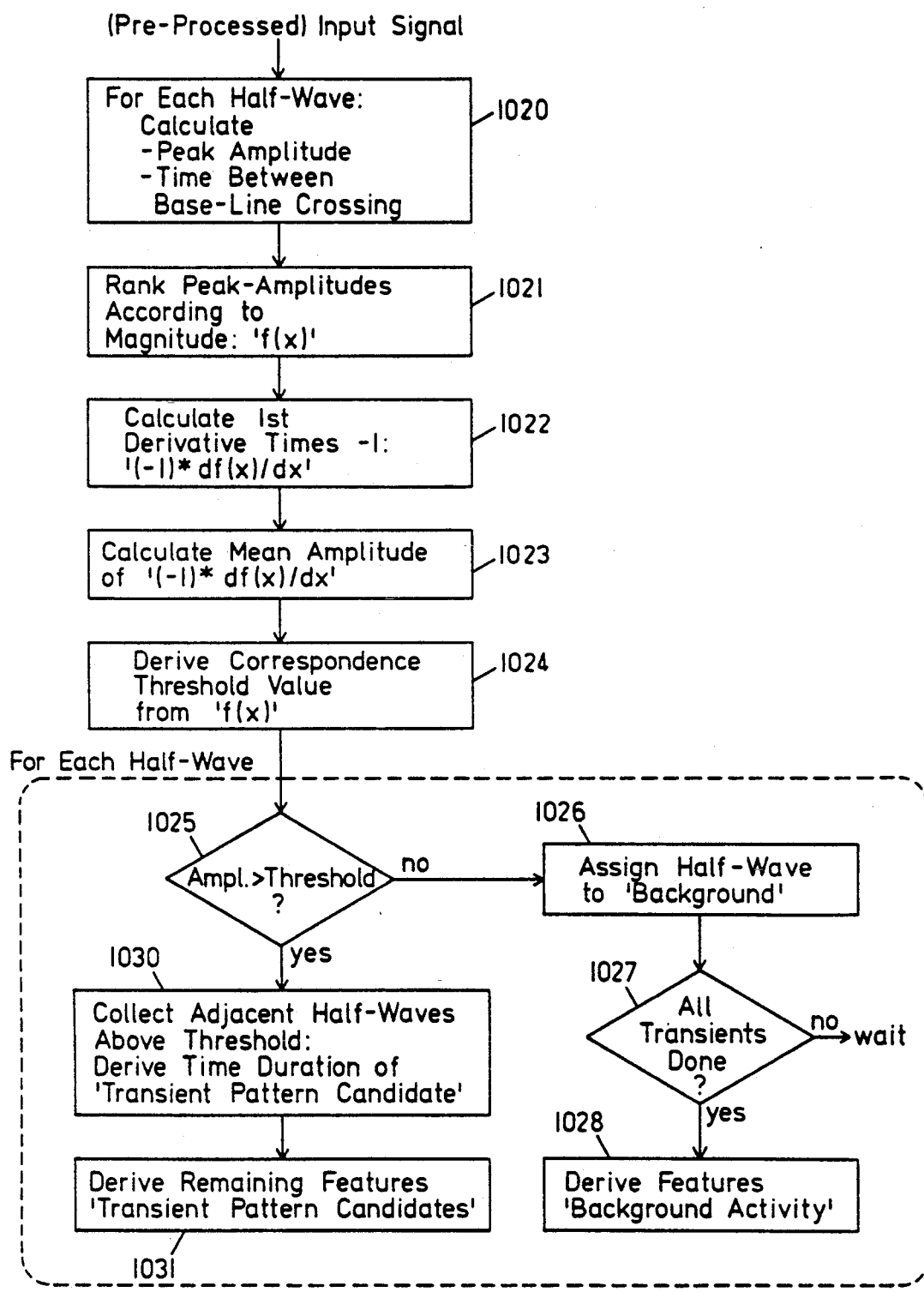
FIG. 14 is a flow diagram showing the program steps in the calculation of adaptive amplitude threshold and features.

The program steps carried out by the computer central processing unit of the analysis system during adaptive amplitude calculation is shown in the flow diagram of FIG. 14. The preprocessed input signal is rectifyed and for each half wave the peak amplitude and time between base-line crossings is calculated (1020) and the half wave peak amplitudes are then ranked according to magnitude to create the function "f(x)" (block 1021), and the calculation is made of the first derivative, times minus one, of the function f(x) (1022). The mean amplitude of the negative derivative of the function is then calculated (1023) and a corresponding threshold value is derived (1024). Then, for each half wave, the amplitude is compared to the threshold (1025) and if the amplitude is not greater then the threshold, the half wave is assigned to the background (1026). Thereafter, a check is made to see if all transients are done (1027) and if not, the program waits for further data; if all transients are done, the program derives the features of the background activity (1028). If the amplitude of the particular half wave was greater than the threshold, adjacent half waves above the threshold are collected and the time duration of the transient pattern candidate is derived (1030). Thereafter, the remaining features of the transient pattern candidate are derived (1031), and the program cycles until all the data is processed.

Figure 15:
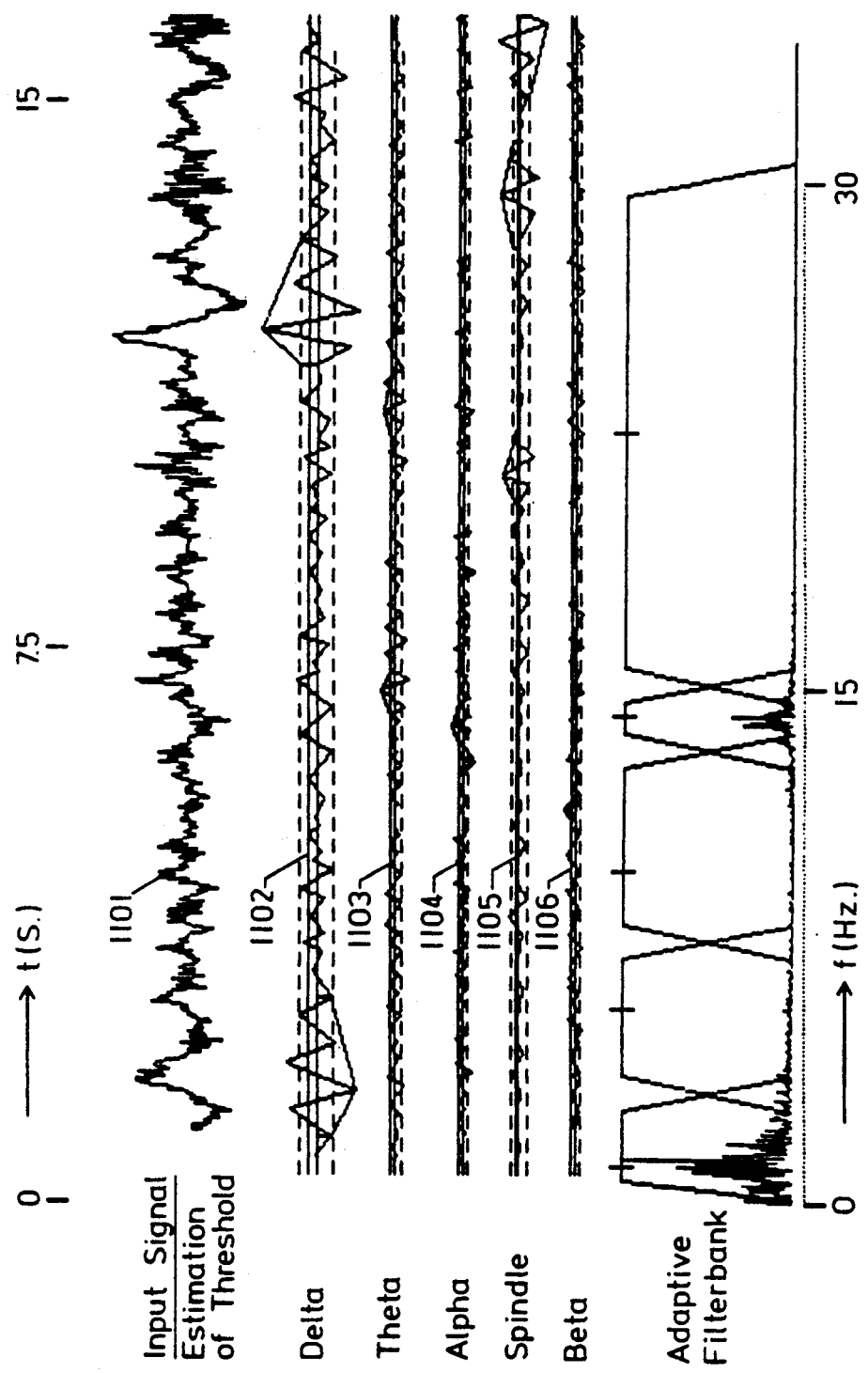
FIG. 15 are graphs showing typical examples of adaptive multiple filtering, partial demodulation of an EEG signal and multiple predetection of transient pattern candidates.

FIG. 15 illustrates results of applying the foregoing technique of estimation of an adaptive amplitude threshold to the outputs from all frequency bands 1102–1105 of a signal 1101. Only peak values of half waves are indicated in this example together with the times of onset and ending of "transient pattern candidates" exceeding the various thresholds.

Figure 16:
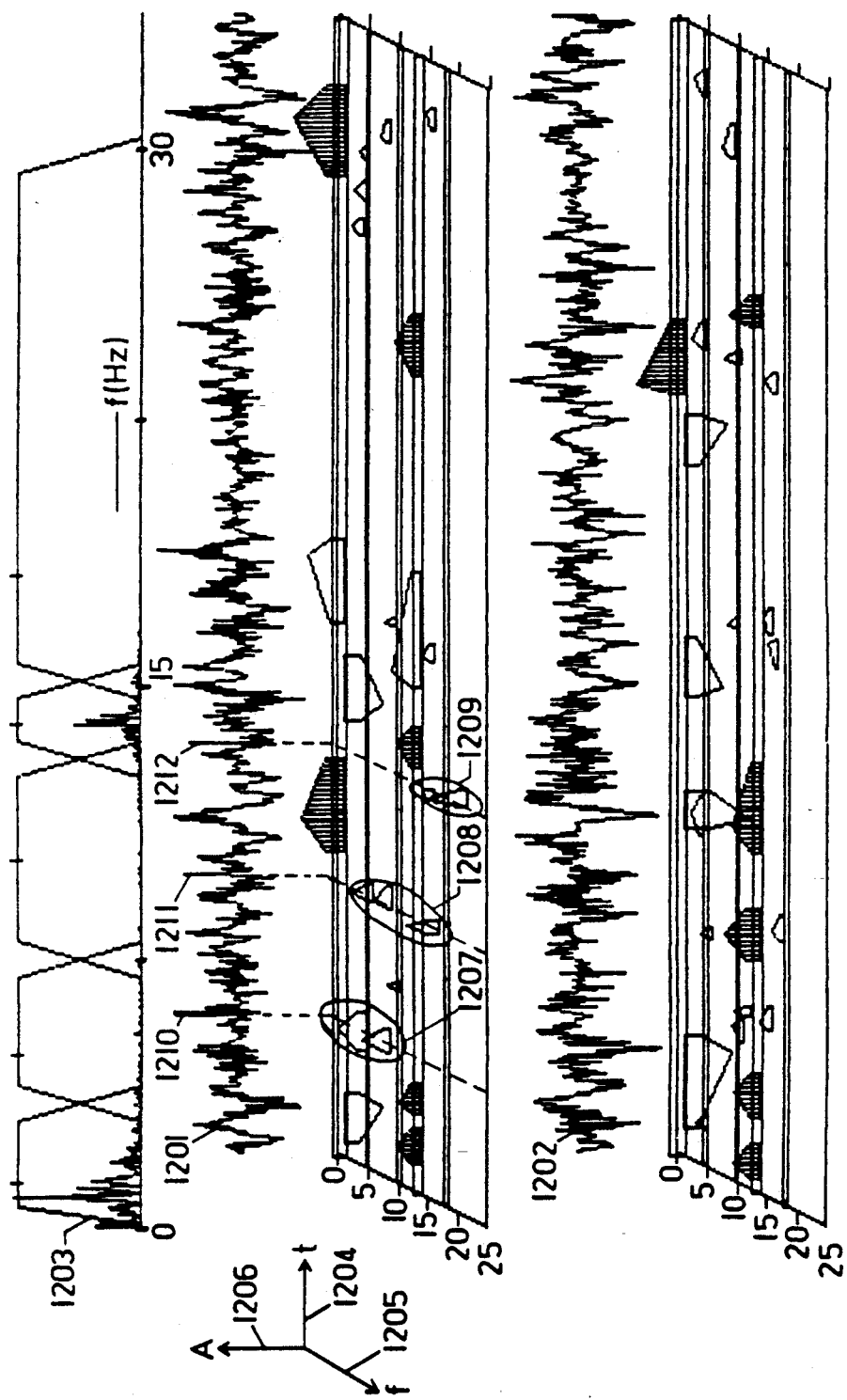
FIG. 16 are graphs showing typical examples of the results of the procedure of feature extraction and pattern detection for two EEG signals being processed in parallel.

FIG. 16 illustrates results of the feature extraction procedure for two EEG signal channels 1201 and 1202 processed in parallel over a 30 second epoch. The adaptive filter bank 1203 is shown at the top, and the extracted features are shown in a quasi 3-dimensional presentation of time, frequency and amplitude, designated in the coordinate system by the numbers 1204, 1205, 1206 in FIG. 16. Features that are extracted for each transient pattern candidate as well as for the background activities (mean amplitude, mean frequency) are clear from these graphs. Features that are extracted for the transient pattern candidates are peak amplitude, time of occurance of a peak, time of onset, duration, and mean amplitude and for the EEG candidates mean frequency and four additional numbers. These four additional numbers for the EEG "candidates" include ratios between peak amplitude and frequency of possible simultaneously occuring "candidates" in two adjacent frequency bands. These four ratios allow for tracing harmonics and subharmonics. They furthermore allow for the detection of short lasting transient patterns that have a bandwidth broader than the widths of the band-pass filters used. Such patterns often give rise to simultaneous "ringing" of adjacent band-pass filters. This is illustrated in FIG. 16 by the simultaneous "ringing" of adjacent band filters at positions 1207, 1208, and 1209 from waveforms artificially added to the input signal which include a sharp wave 1210, a spike 1211, and a sharp spike 1212. In the example illustrated in FIG. 16, K-complexes (positive polarity but no synchrony are required in this example) and sleepspindles which are detected are indicated by shading of the corresponding "real" transient patterns.

Figure 17:
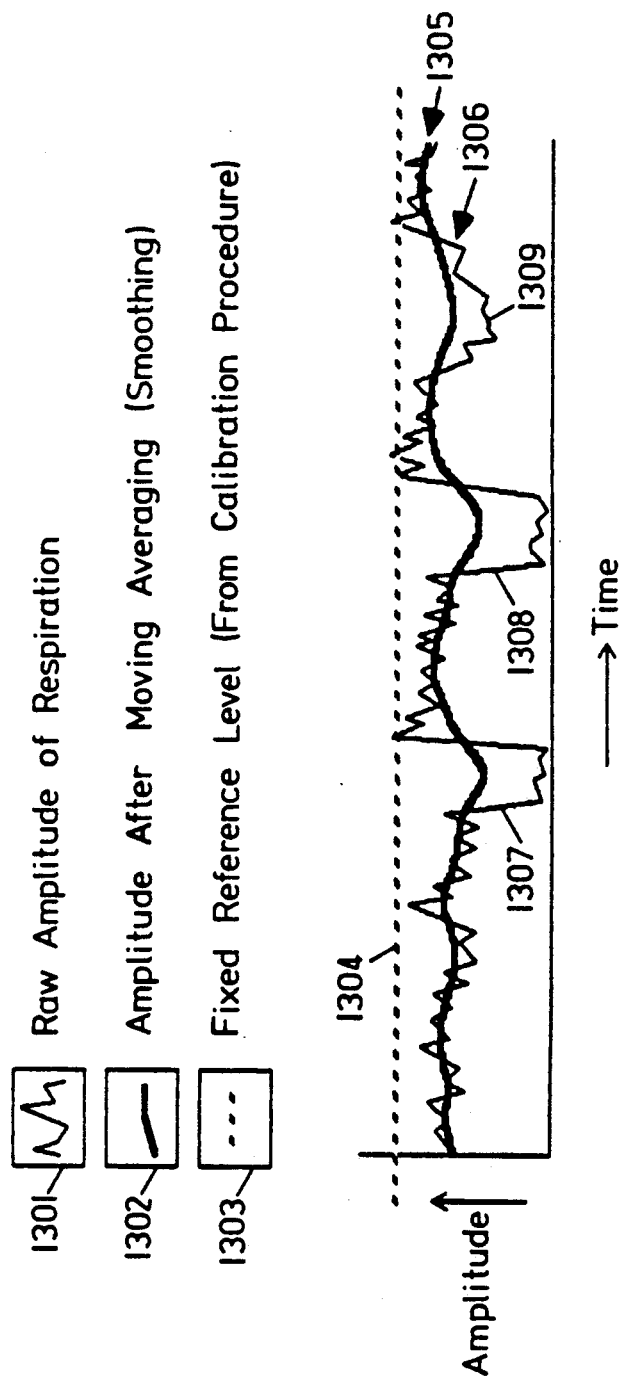
FIG. 17 are graphs illustrating a comparison of a respiratory parameter with two types of reference values to allow detection of hypopnea and apnea.

FIG. 17 illustrates a comparison of a respiratory parameter 1301 (the raw amplitude of respiration in this example) with two types of reference level functions so as to detect hypopnea (less than 75%) and apnea (less than 50%). In this example, the overall amplitude of respiration is substanially lower than the amplitude found in a calibration procedure carried out before starting the actual recording. As a result, the corresponding fixed reference level 1304 has a value which is too high, giving rise to false positive hypopnea and apnea. The second type of reference value indicated by the line labeled 1302 in FIG. 17 is a smoothed version of the raw amplitude 1301 of the respiration. By choosing an appropriate width of smoothing (2 minutes in this example) the adaptive reference value easily follows long-term shifts through the time of recording but fails to follow short term fluctuations (those lasting in the range of tens of seconds) as seen during the apnea periods labeled 1307 and 1308 or the short lasting hypopnea 1309. The use of a moving average reference level yields more consistent results in situations where long term fluctuations occur—for example, those caused by a degrading over time of the signals representing rib cage and abdomen movements.

FIG. 18 shows detection rules for a particular EEG pattern, in this case sleepspindles. The white or undarkened elements 1401 correspond to rules that are active and the black elements 1402 correspond to rules that are excluded or not used. The graphic of FIG. 18 is presented by the analysis system on the colored display screen 34 and allows the user to select inclusion and exclusion of rules by using a mouse to move a cursor over the positions of the rules to be excluded or included and clicking the mouse to select or deselect rules. When the mouse switch is checked, the elements will switch in a cyclic fashion between "bright" (active/included elements) and "dark" (disabled/excluded elements). When activating the elements labeled "synchrony", "context" and "combination", pop-up windows will appear that contain the pertinent rules.

Figure 19:
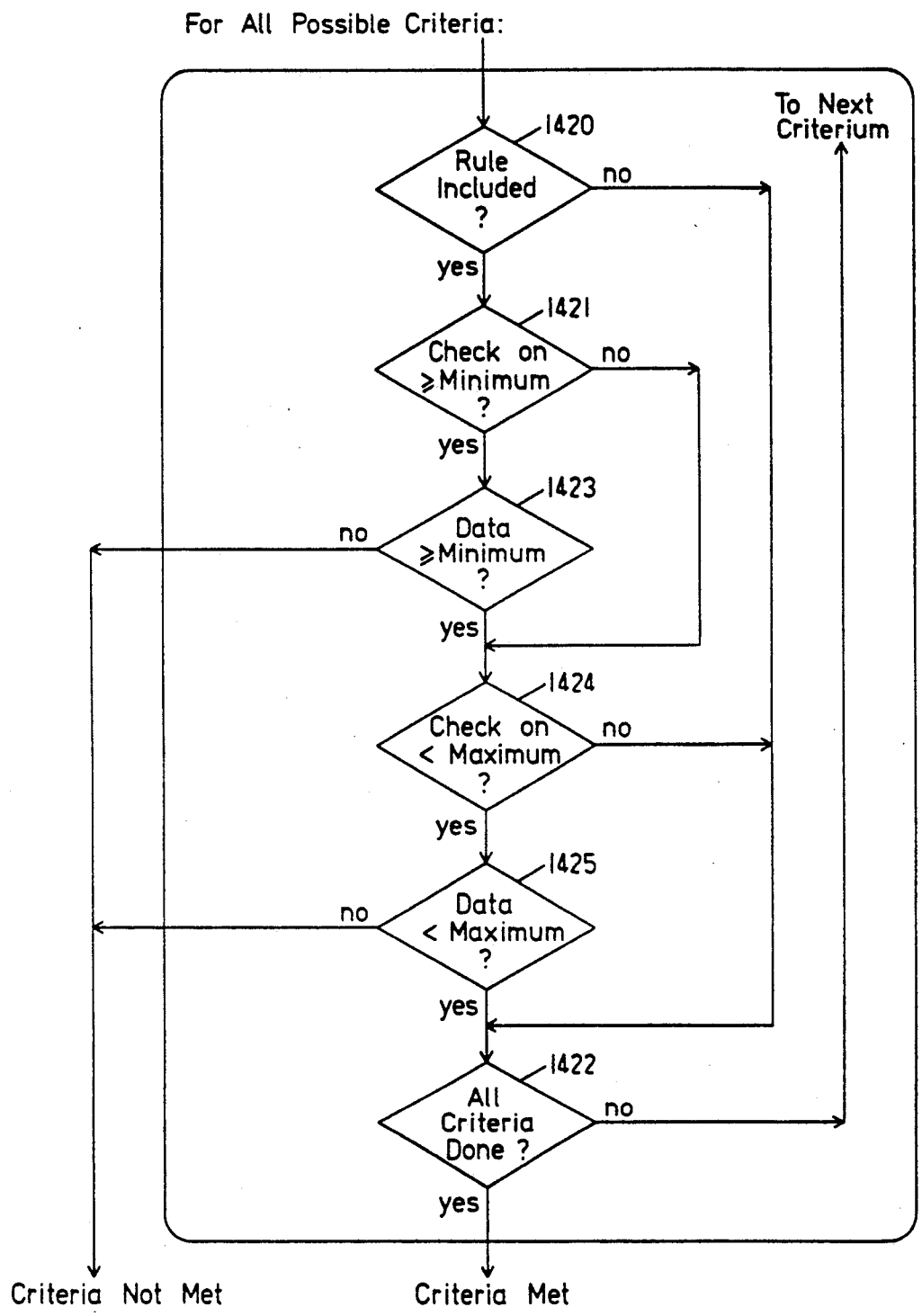
FIG. 19 is a flow diagram illustrating the checking of criteria (rules and reference levels).

The manner in which the system program checks criteria (applicable both to pattern detection and classification) is shown in the flow diagram of FIG. 19. First, the program checks to see if a particular rule is included (1420) and, if so, checks to see if the rule requires that the candidate be greater than or equal to a minimum (1421). If a rule is not included at 1420, the program determines whether all criteria are done (1422) and, if so, the program signals that all criteria are met for that pattern candidate and the candidate is saved. If all criteria are not done, the program cycles to get another criterion. If the rule requires greater than or equal to the minimum at 1421, the program determines whether the data are greater than or equal to the minimum (1423). If not, the program signals that the criteria are not met and cycles to obtain another pattern candidate. If it is determined at 1421 that the rule does not require a minimum, the program checks whether the rule requires a maximum (1424); if not a check is made to determine if all criteria are done (1422). If a maximum is required, the candidate is checked to determine if it is less than the maximum value (1425) and if not a signal is given that the criteria are not met and the program obtains another pattern candidate. If at 1425 the candidate data are less than the maximum, a check is made to determine if all criteria are done (1422); if so, the criteria-met signal is provided, and if not, another criterion is obtained. If, at decision point 1423, the data is found to be greater than the minimum, the program then checks to see if the rule requires less than a maximum value; if not, the program determines whether all criteria are done (1422), and if so, the program determines whether the data are less than the maximum value. If not, a criteria not met signal is given, and if so, a check is made to see if all criteria are done (1422). The program continues to cycle in this manner until all criteria are done.

The pattern detection criteria for EEG signals can include some or all of the following: (1) low frequency artifact, (2) broad band artifact, (3) high frequency artifact, (4) delta background and burst activity, (5) theta background and burst activity, (6) alpha background and burst activity, (7) beta 1 background and burst activity, (9)K-Complex, (10) sleepspindle, (11) sharp wave, (12) spike, (13) custom 1 through custom 4 patterns. EOG type criteria include rapid eye movement and slow eye movement. EMG type signals include EMG burst, and motility signals include motility burst.

Figure 20:
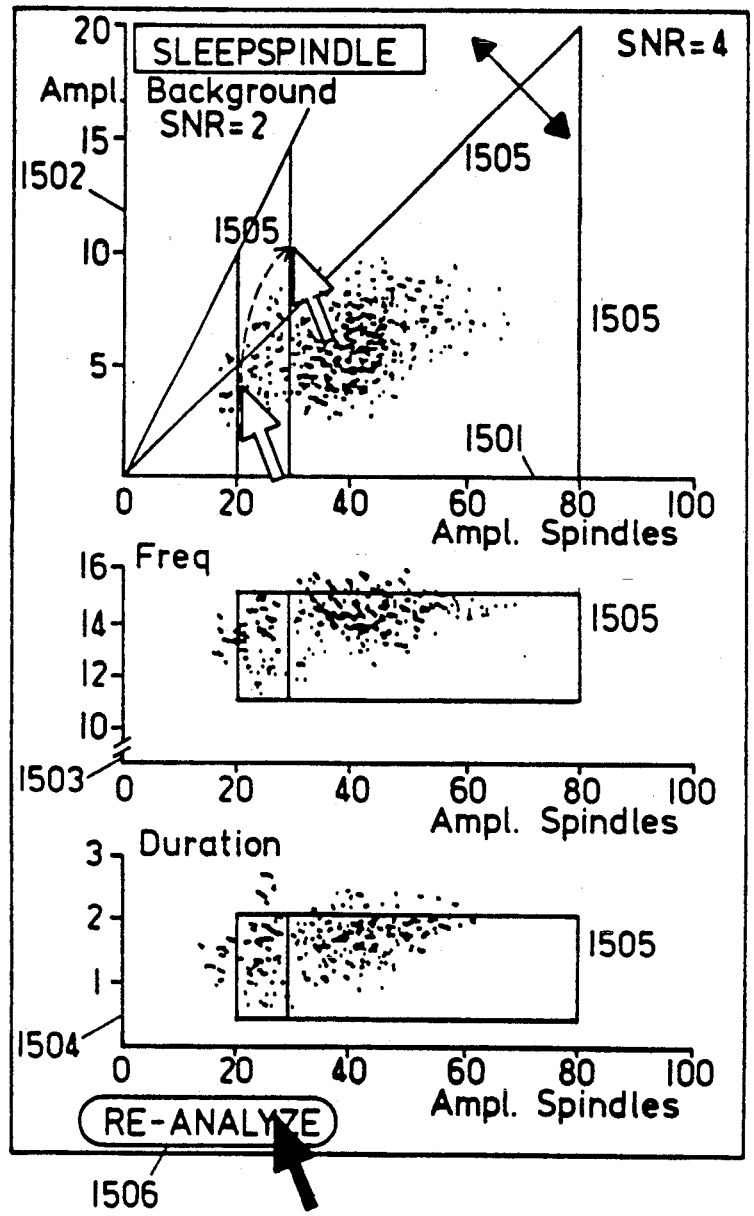
FIG. 20 shows the display provided by the analysis system to an operater illustrating detection levels for a particular EEG pattern in conjunction with multiple scattergram displays of features of transient pattern candidates extracted over the entire recording time.

FIG. 20 shows the presentation on the video display screen 34 of the detection levels for a particular EEG pattern in conjunction with a multiple scattergram display of features of transient pattern candidates extracted over the entire recording time. For all indicated scattergrams, the horizontal axis represents the peak-to-peak amplitude of the detected pattern candidates 1501, in this example, sleepspindles. Going from the top down, the vertical axes represent the amplitude of background activities 1502, the frequency range 1503, and the time duration 1504 of the candidates, respectively. Thus, the user can easily verify whether there is a reasonable matching of reference levels and actual analyzed data values. Any reference level 1505 can be adjusted using the mouse and the cursor arrow to drag a "reference line" to another position; in the example being illustrated in FIG. 20, the "minimum amplitude" for spindle detection is being dragged from 20 to about 30 microvolts. After at least one modification is done, an active re-analysis can be started by placing the cursor arrow on the "RE-ANALYSE" spot 1506 at the bottom of the screen.

Figure 21:
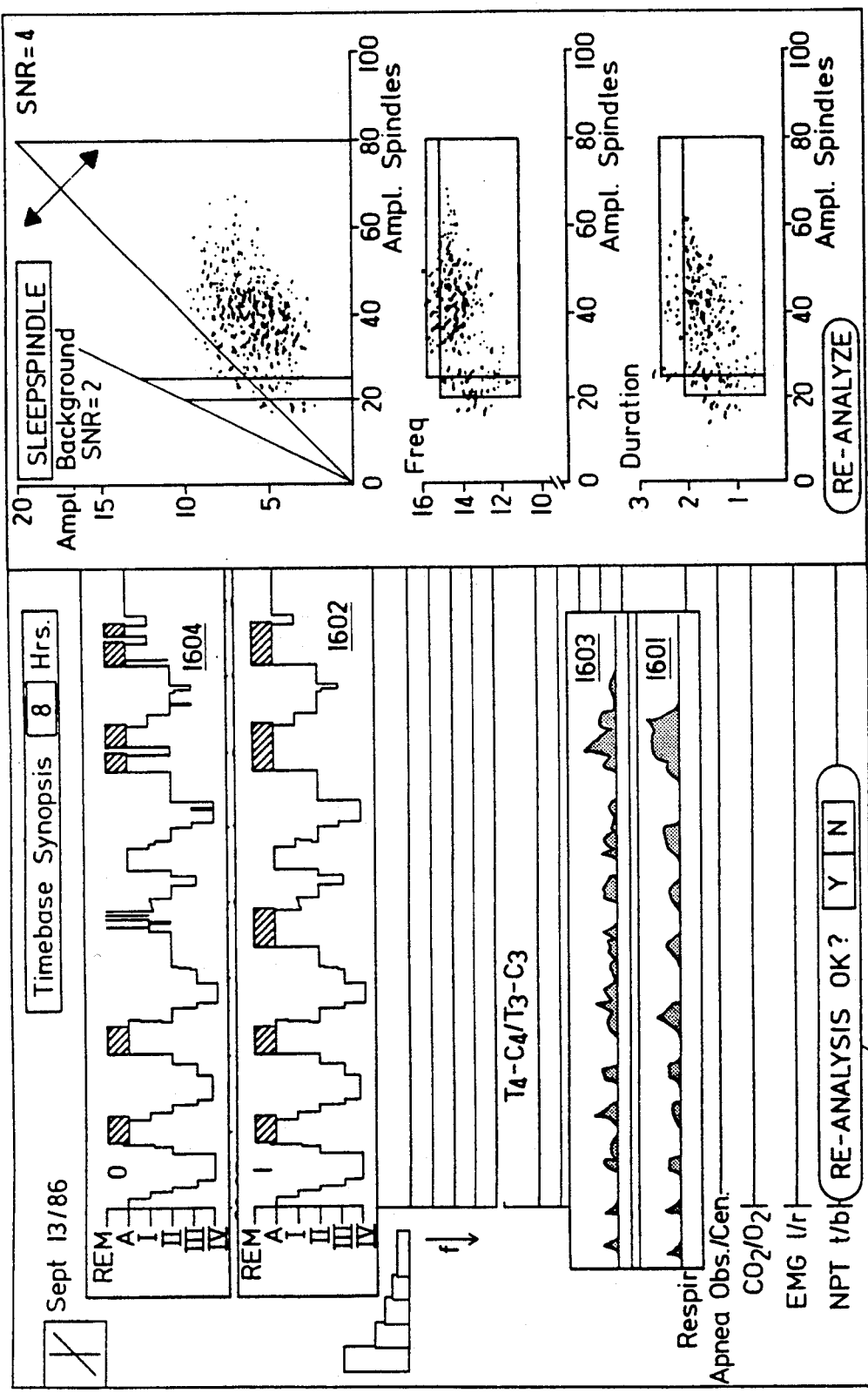
FIG. 21 shows the display provided by the analysis system to the operator which displays the results of re-detection of a particular EEG pattern and the effect of such re-detection on classification of sleep.

FIG. 21 shows the display provided to the operator which illustrates results of an exemplary redetection of a particular EEG pattern and the effect of that redetection on the classification of sleep. During and after the actual re-analysis the synopsis is dark except for the curve which indicates the behavior over time of the pattern 1603 being selected for redetection and the subsequent reclassification pattern of sleep 1604. Re-analysis is authorized or rejected by using the mouse to place the cursor on an authorization window 1605. In the example shown, the minimum amplitude threshold and the upper thresholds for frequency and time duration have been updated for better matching. As a result, the time course 1601, indicating the sleepspindles after redetection, shows a lower "noise-floor". This has a stabilizing effect on the new hypnogram 1602 because sleep stage II is now scored more reliably.

Figure 22:
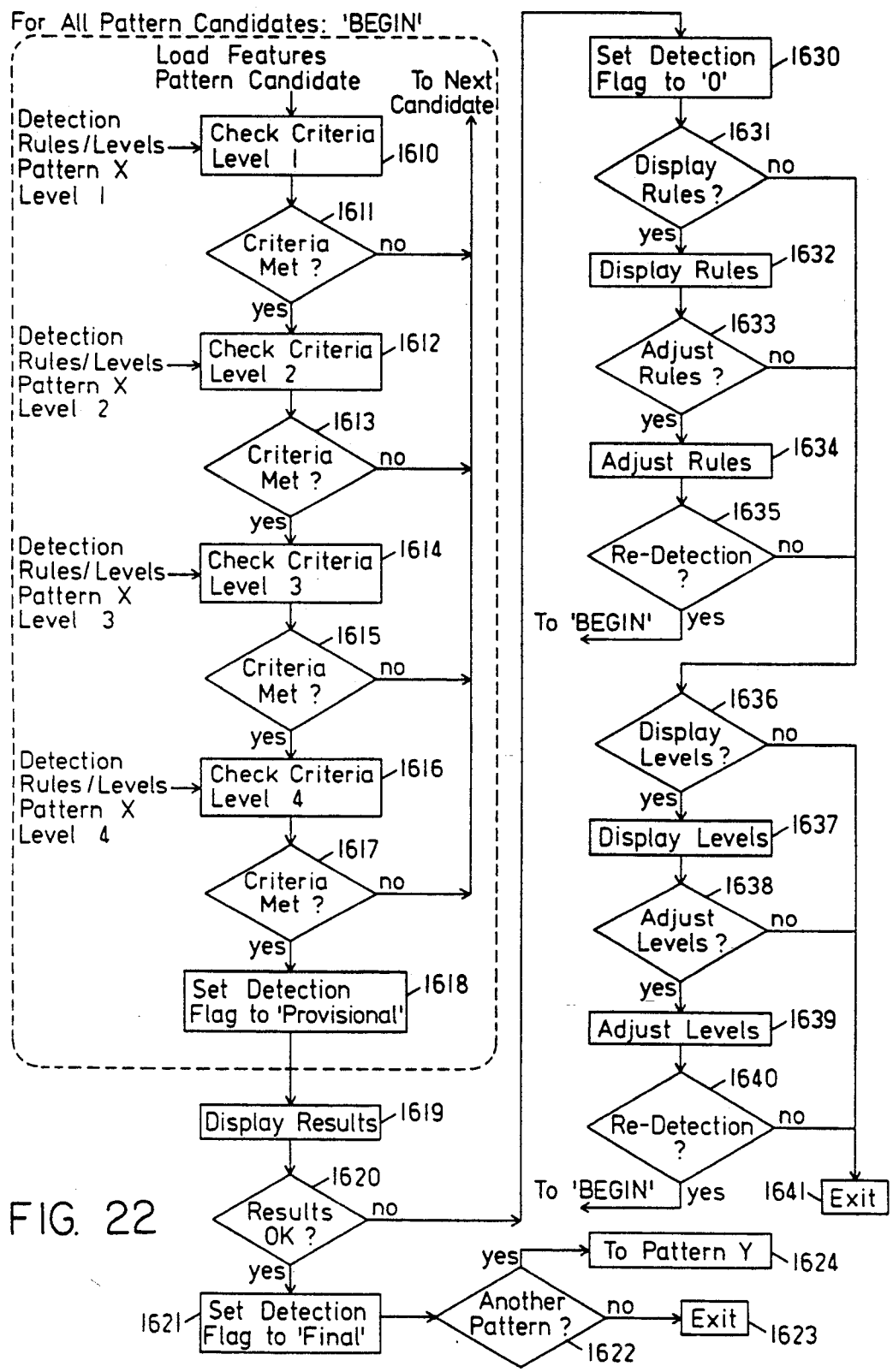
FIG. 22 is a flow diagram showing the program steps carried out by the analysis system and the detection and re-detection system.

A flow diagram showing the program steps carried out by the computer controller of the analysis system is illustrated in FIG. 22. The program begins by loading features of the pattern candidates into memory and applying the detection rules for the particular pattern at level 1 to see if the pattern candidates meet these criteria (1610). If the criteria are not met (1611) the program proceeds to review the next candidate; if the criteria are met the candidate is checked with respect to criteria level 2 (1612) and if these criteria are not met (1613) the program proceeds to the next candidate. If the criteria are met, the candidate is then checked against criteria level 3 (1614) and if these criteria are not met (1615) the program proceeds to the next candidate. If the third criteria of the third level are met, the candidate is checked against the criteria of level 4 (1616) and if these criteria are not met (1617) the program proceeds to the next candidate. If all the criteria are met, a detection flag is set to "provisional" (1618) and results are displayed to the operator (1619). The program then determines whether the results are acceptable (1620) and, if so, sets the detection flag to "final" (1621) and asks the user to perform redetection of another pattern (1622). If the user decides not to redetect another pattern, the program exits (1623); if another pattern should be redetected, the program proceeds to review the next pattern, designated pattern Y (1624). If the operator indicates that the results are not acceptable at the decision point 1620, a detection flag is set to "0" (1630) and the program checks to see if the operator wishes to display the rules (1631). If so, the rules are displayed (1632) and the program determines if the operator wishes to adjust the rules (1333). If so, the rules are adjusted (1634) in an interactive fashion with the operator and the program checks determine if redetection is selected (1635). If so, the program goes back to begin and loads the feature pattern candidates all over again. If at any of the decision points 1631, 1633 and 1635, the decision is no, the program proceeds to ask the operator whether to display levels (1636) and if not, the program exits (1641). If so, the levels are displayed (1637) and the program waits to determine if the operator wishes to adjust levels (1638). If not, the program exits; and if so, levels are adjusted (1639) and the program determines if redetection is requested (1640). If not, the program exits; and if so, the program returns to Begin to load another feature pattern candidate.

FIG. 23 illustrates a display on the CRT screen of display device 34 of the Rechtschaffen and Kales rules for the classification of sleep which have been retrieved from the Knowledge Base. The default epoch duration displayed in the box 1701 is 30 seconds. The matrix of rules has the sleep stages along the horizontal axes and the constituting patterns along the vertical axes. Reference levels are listed in the matrix (e.g., "higher than 75 microvolts" for "delta" activity in sleep stage IV). The bright elements 1702 in the matrix indicate rules that are active; they are included in the sleep classification. The dark elements 1703 are rules that are disabled; they take no part in the classification. The inclusion or exclusion of rules is accomplished by moving the cursor using the mouse to the appropriate matrix element and clicking the mouse. The epoch duration can be modified (for example, to time periods of 120, 60, 30, 20, 15, 10, 5 and 2 seconds) by pointing to the "scrolling arrow" 1704 with the cursor and clicking the mouse.

Figure 24:
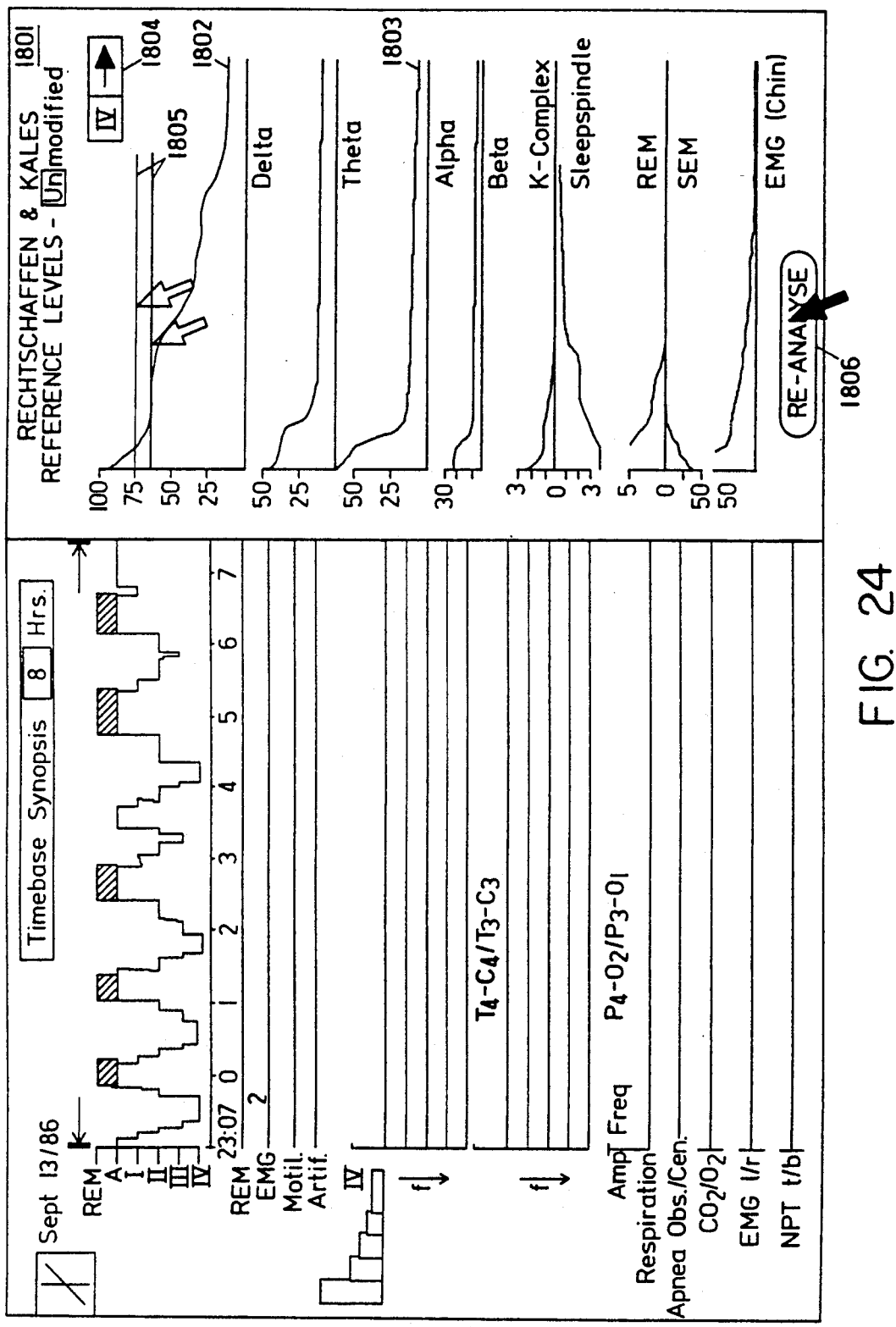
FIG. 24 shows a display provided by the analysis system to the operator illustrating one strategy for modifying reference levels by the operator to effect reclassification of sleep.

FIG. 24 illustrates a color display CRT screen provided by the analysis system which illustrates a strategy for modifying reference levels to accomplish the reclassification of sleep. Reference levels 1801 for sleep classification are retrieved from the Knowledge Base. They are displayed at the right side of the screen in conjunction with the actual measured values of the patterns, being the input parameters for the sleep classification. The values are ranked according to magnitude prior to display. Relatively long periods of stable sleep, as stage IV, stage II, and REM, will now appear as plateaus in the monotonically decreasing "Delta" curve 1802. Patterns that have an "on-off" behavior, for instance, alpha activity 1803, will typically show two distinct levels. Reference levels in the curves are displayed only for one stage at a time (stage IV in this particular example). Other stages may be selected by the operator by moving the cursor with the mouse to the box 804 containing the black arrow. Different stages will appear in a cyclic fashion (preferably IV, III, II, I, Awake, REM). Reference levels for the selected sleep stage can be modified by clicking the mouse when the cursor is on the displayed level or levels and dragging the reference line or lines 1805 to another position. Reference levels for other sleep stages can be adjusted after pointing the cursor to the box 1804 to select another stage. After at least one level is modified, an active re-analysis can be started by clicking the standby "RE-ANALYSE" box 1806 at the bottom of the screen.

Figure 25:
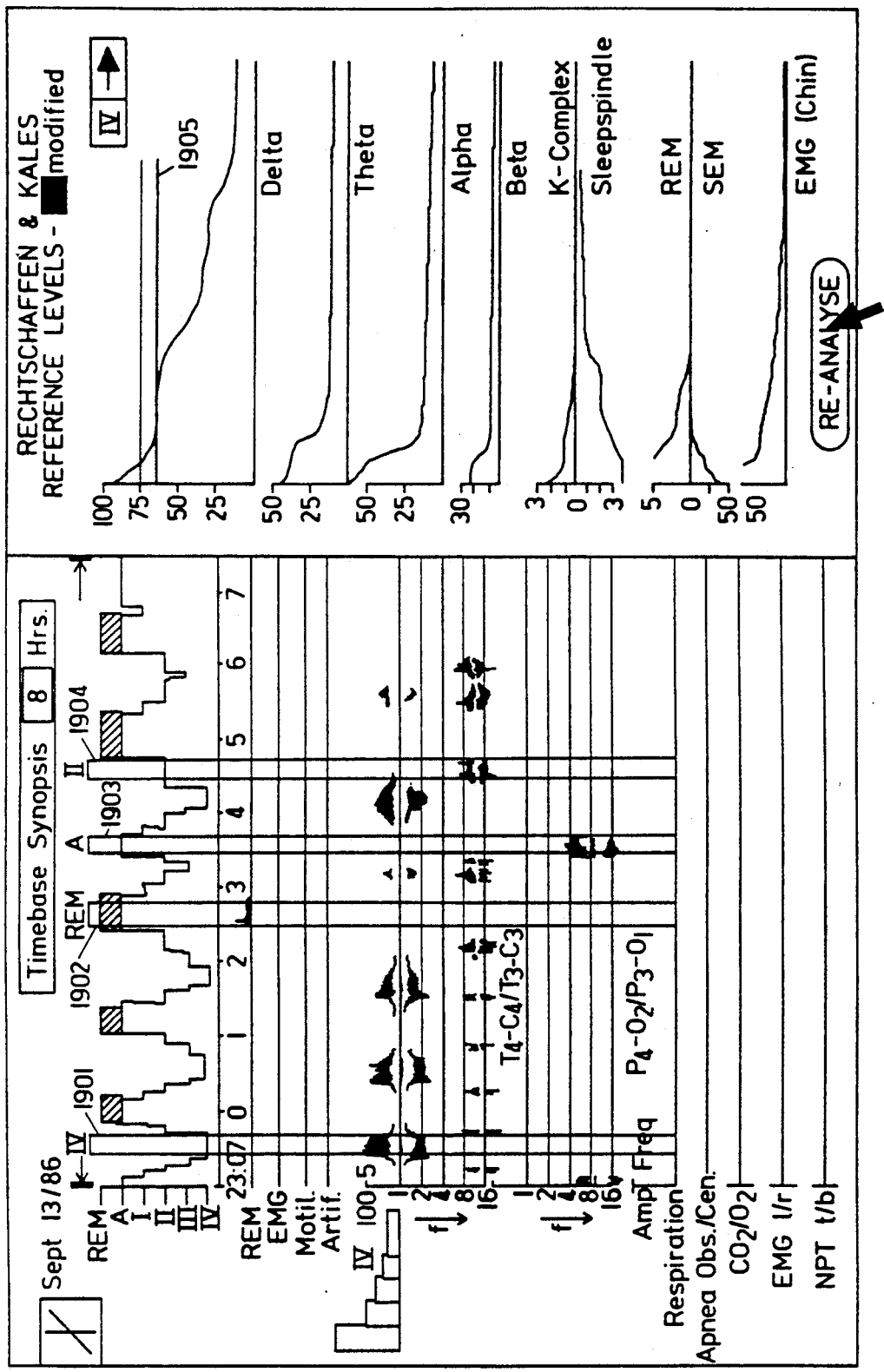
FIG. 25 shows a display provided by the analysis system to an operator showing the results of another strategy by the operator to modify reference levels to effect the reclassification of sleep.

In the representation of the display screen of FIG. 25, another strategy for modifying the reference levels to reclassify sleep is illustrated. This strategy consists of indicating typical periods for the various sleep stages in the synopsis using the verical cursor (stage IV at 901, REM sleep at 1902, Awake at 1903, and stage II at 904 in this example) followed by a calculation of mean values for the stages. For those stages that are not indicated, mean values will be determined by linear interpolation between adjacent stages. These mean values are indicated in the right side window, and in the example only the new value for the delta curve 1905 is indicated. With these mean values as a guide, the user can now decide how he wishes to modify the various levels and thereafter do a re-analysis with the modified levels.

Figure 26:
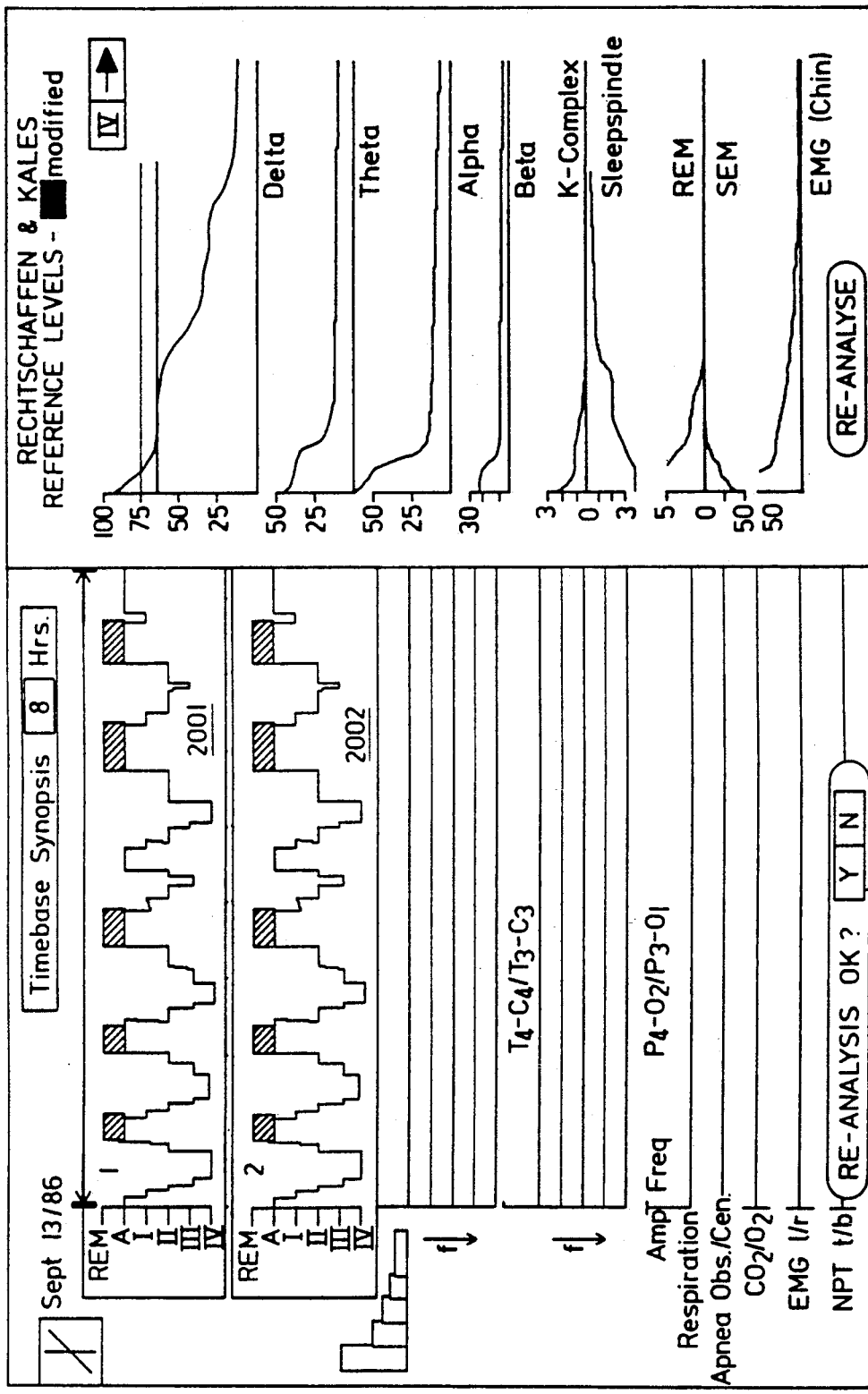
FIG. 26 shows a display provided to an operator by the analysis system showing the results of the reclassification of sleep.

A representation of the display on the CRT screen in FIG. 26 illustrates a typical result of the reclassification of sleep. During and after the actual re-analysis, the synopsis will be dark except for the classification of sleep curve 2001. The result of re-analysis (resulting in the re-classification of sleep) will appear in a separate bright window 2002. In this example the adjusted (here the decreased) level of delta activity for sleep stage IV gives rise to an increase of stage IV as a percentage of the total. This can be easily concluded in this example by comparing cycle 2 and 3 of both hypnograms. The re-analysis must be authorized or rejected by the user. Authorization is done by clicking the mouse when the cursor is on the Y at the bottom left window 2003. Rejection is indicated by clicking the mouse when the cursor is on the N. The new hypnogram 2002 will then replace the previous hypnogram 2001 as displayed on the screen.

Figure 27:
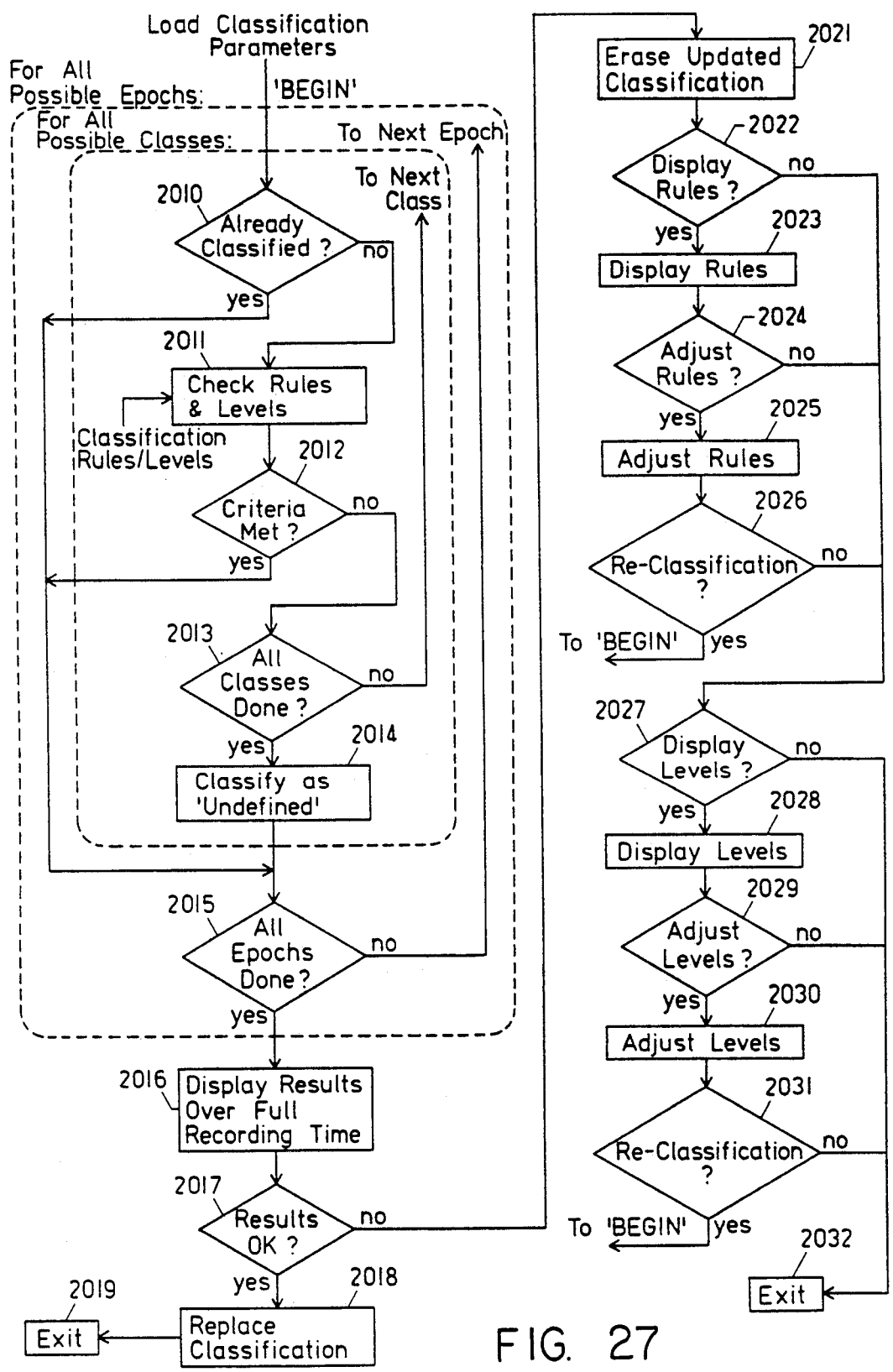
FIG. 27 is a flow diagram showing the program steps carried out by the analysis system in the classification and reclassification procedure.

A flow diagram showing the program steps carried out by the analysis system during classification and reclassification is illustrated in FIG. 27. For all consecutive epochs, after the program begins it checks whether a particular epoch has already been classified (2010) and, if not, checks the contributing parameters against the rules and levels (2011) and determines whether these criteria are met (2012). If not, the program checks to see if all classes are done (2013) and if not, goes on to the next class. If all classes are done, the particular epoch is classified as undefined (2014) and if all epochs are done (2015) results are displayed (2016). If at the decision point 2010, it was found that the pattern was already reclassified, and at decision point 2012 that the criteria for a particular class are met, those results are displayed if all epochs are done. The program then checks to see if the operator approves the results (2017) and, so, replaces the classification (2018) and exits (2019). If the results are not acceptable to the operator, the updated classification is erased (2021) and the operator is asked whether the rules are to be displayed (2022). If so, the rules are displayed (2023) and the program waits for input from the operator as to whether the rules are to be adjusted (2024). If so, the rules are adjusted (2025) interactively, and the program requests the operator to determine whether reclassification is to occur (2026). If so, the program returns to Begin and checks for all epochs whether a particular epoch was already classified. If at the decision point 2022 the rules are not to be displayed or at decision point 2024 the rules are not to be adjusted or at decision point 2026 reclassification is not to take place, the program then proceeds to determine whether levels are to be displayed (2027) and if so, displays the levels (2028). Once the levels are displayed, the program checks to see whether the operator wishes levels to be adjusted (2029) and if so proceeds to adjust the levels (2030) interactively with the operator. The program then checks to see if whether reclassification is requested (2031) and if so, returns to Begin. If at the decision point 2027 levels are not to be displayed, at decision point 2029 levels are not to be adjusted and at decision point 2031 reclassification is not to take place, the program exits (2032).

Figure 28:
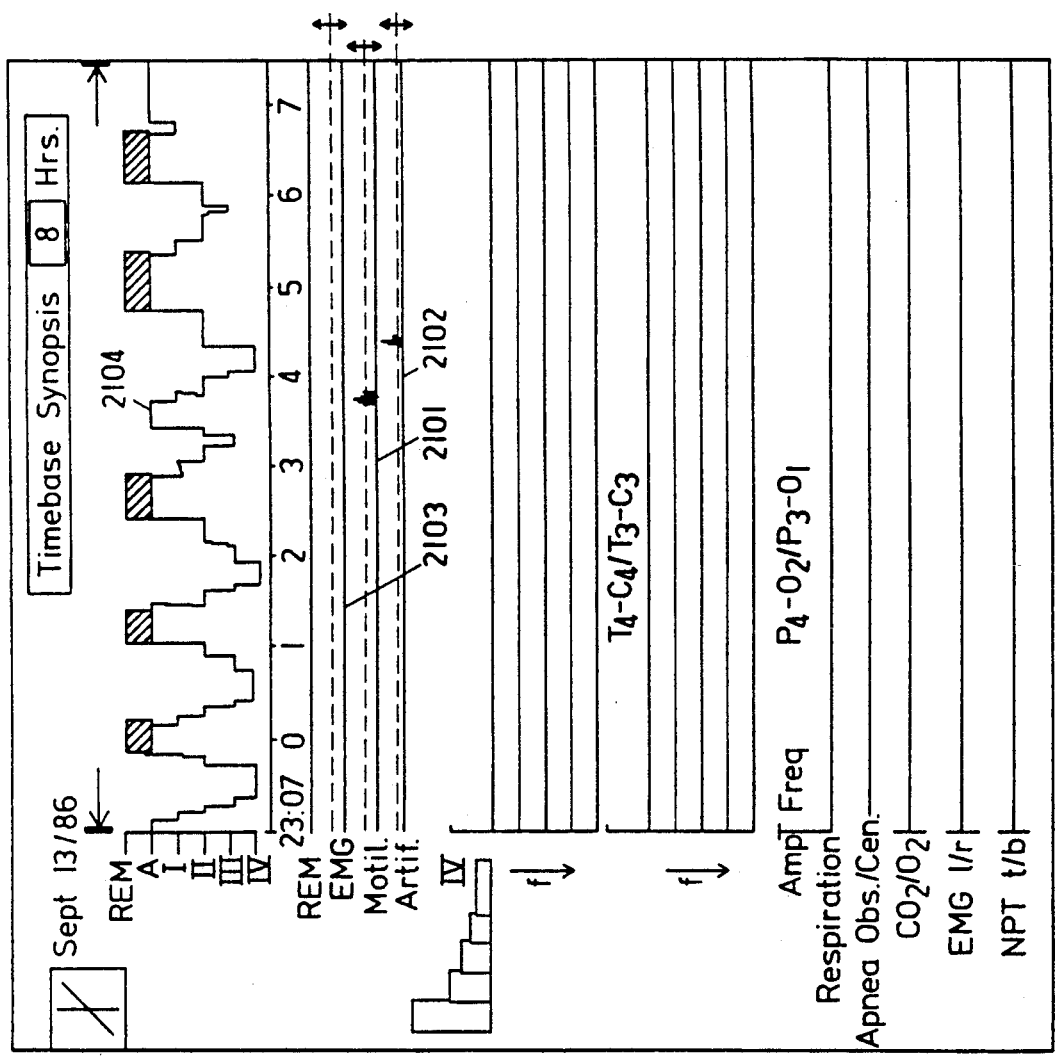
FIG. 28 shows a display provided to the operator by the analysis system illustrating how some variables can be used for interactive artifact rejection with the objective of avoiding misclassification of sleep.

FIG. 28 shows a CRT screen display illustrating the manner in which variables can be adjusted for interactive artifact rejection in an effort to avoid misclassification of sleep. Using the mouse, the operator can place a threshold level cursor on variables such as "motility" 2101 (if measured), detected artifacts 2102 and/or EMG 2103. For those epochs where such a variable exceeds the cursor level, the classification of sleep becomes "undefined"; this is indicated to the user by omitting the graph of the hypnogram 2104.

FIG. 29 is a CRT screen display showing the classification rules for the various types of apnea from the Knowledge Base. The matrix of rules has the type of apnea along the horizontal axis and the constituting patterns along the verical axis. Reference levels are listed in the element of the matrix. The bright elements 2201 in the matrix indicate rules that are active. The dark elements 2202 are rules that are inactive or disabled. Inclusion or exclusion of rules is accomplished by placing a cursor over the appropriate element within the matrix and clicking the mouse to enter the desired state.

Figure 30:
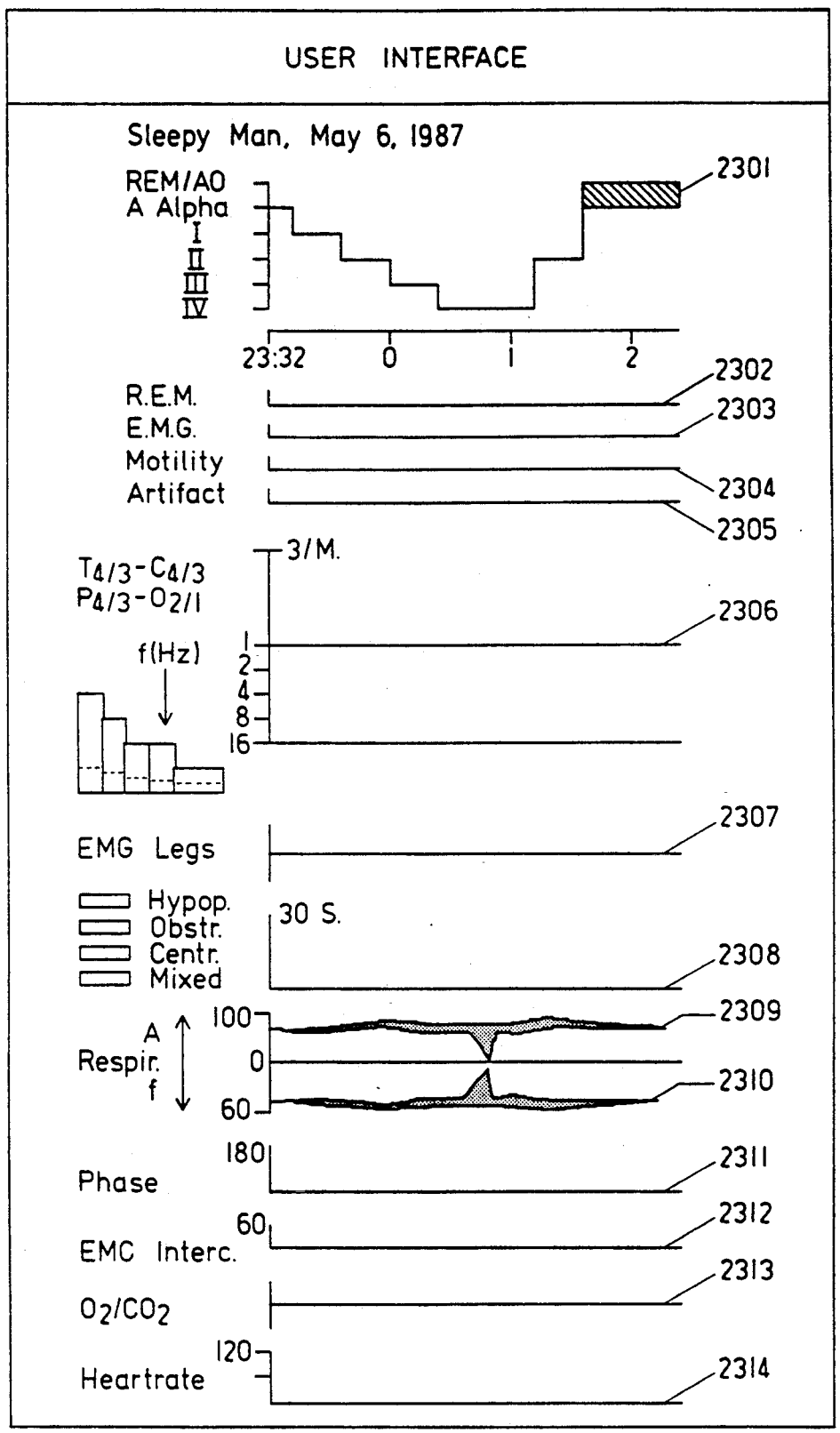
FIG. 30 is a display provided by the analysis system to an operator which shows an example of the multiple variables that can be displayed in a synopsis.

FIG. 30 is an example of a CRT screen display by the system showing the multiple variables that can be displayed in a synopsis. In this typical example, going from the top down, the following are seen:

(a) the classification of sleep in terms of the hypnogram 2301, (b) the number of detected rapid eye movements 2302, (c) the amplitude of EMG 2303 derived from the chin, (d) the amplitude of "motility" 2304, (e) the time duration of detected artifacts 2305 (three types are indicated using different colors for low frequency, high frequency and broad band artifacts), (f) amplitude and frequency of the classic EEG background rhythms in combination with detected patterns such as K-complexes, theta and alpha bursts and sleepspindles, illustrated by the graph labeled 2306 (these EEG phenomena are indicated for four EEG channels in one display that each show two times the parameters for two averaged channels in a mirrored fashion), (g) time duration of EMG bursts 2307 occuring in both legs, displayed mirror-wise, (h) time duration of detected hypopnea and apnea 2308, the color of the curve for apnea indicating the type of apnea, (i) minimum/maximum values 2309 per 30 second epoch of the (average) amplitude of rib cage and abdomen movements (the area in between minimum and maximum values are shaded as an example), (j) minimum/maximum values 2310 of the (average) frequency of rib cage and abdomen movements, (k) minimum/maximum values 2311 of the phase angle between the rib cage and abdomen movements, (l) minimum/maximum values 2312 of the repetition frequency of intercostal EMG bursts, (m) oxygen and carbon dioxide saturation levels 2313, and (n) minimum/maximum values 2314 of heart rate.

Figure 31:
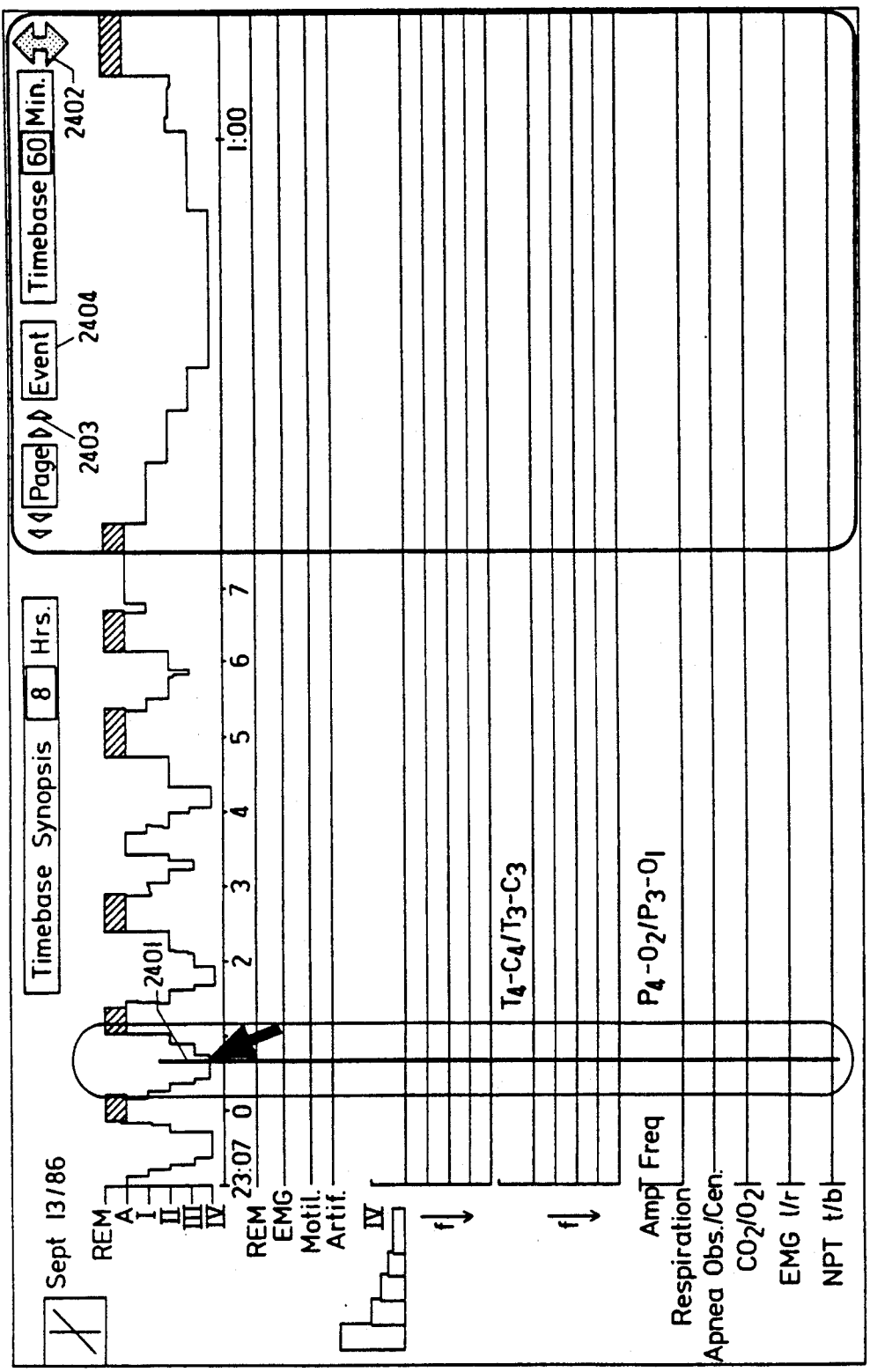
FIG. 31 is a display provided by the analysis system to the operator illustrating the pattern in which the "Zoom" function magnifies a part of the synopsis.

FIG. 31 illustrates a CRT screen display showing the manner in which the "Zoom" function provides for an expansion of a selected part of the synopsis. A moment in time is selected by the user by manipulation of the cursor 2401. A portion of the synopsis, centered around the indicated time of the cursor is then enlarged ("zoom") and appears at the right side of the display. The zoom time base can be modified using the "scrolling arrow" 2402 to scroll adjacent portions of the synopsis into the portion of the synopsis that is enlarged and displayed. The timebase is selectable between 120 minutes and 0.5 minutes, corresponding to a time resolution of 15 seconds to 0.625 seconds, respectively. Forward and backward "paging" ("a page" here is related to the zoom timebase) is done by placing the cursor on one of the associated arrows 2403 and clicking the mouse. The outer arrows correspond to a full "page" advance, while the inner arrows correspond to a half page advance. The Event bar 2404 allows the entry of text with the current time being automatically associated by the system with the text entered. Applications of this zoom function include the following examples. A time base of 90 minutes will, in general, cover one complete sleep cycle. Thus, a resolution of about ten seconds allows for detailed inspection of portions of the sleep cycle. A time base of 30 minutes corresponds to a resolution of about 4 seconds, allowing for inspection of individual K-complexes and sleepsplindles. Short lasting (2 to 5 seconds) alpha bursts, as those which occur during microarousals, will be revealed. This timebase is also suited for analyzing "rhythmic breathing" patterns. A timebase of 10 minutes corresponds to a resolution of less than 2 seconds and a time base of 5 minutes corresponds to a resolution of less than one second. These time bases allow for evaluation of the relationship in time between, for example, the apnea/hypopnea and microarousals. A time base of 0.5 minute corresponds to a resolution of 0.0625 seconds. Combined with a display of raw data over 30 seconds, this allows for a one-to-one checking of the validity of the detection and quantification of the individual signal patterns.

Figure 32:
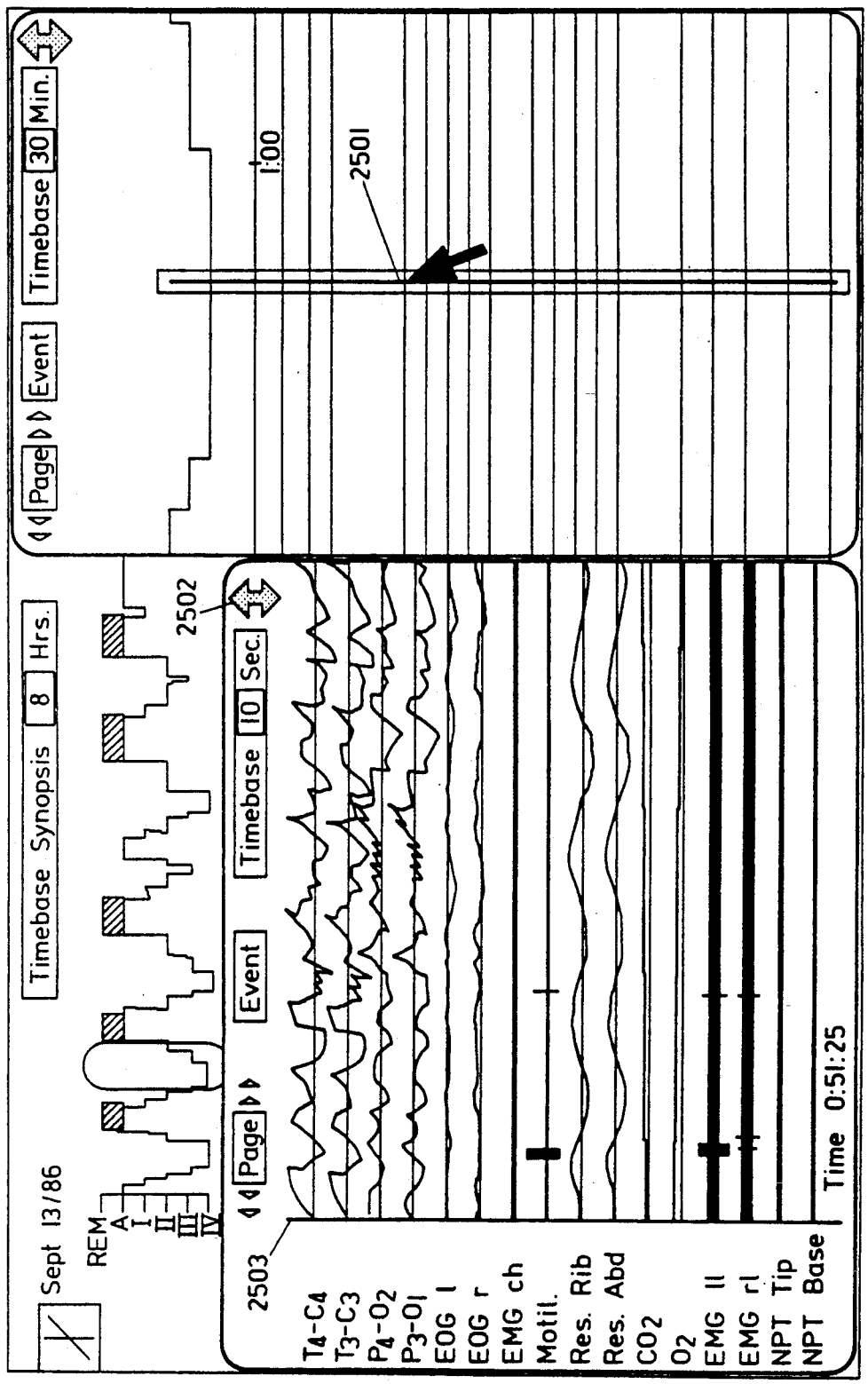
FIG. 32 is a display provided to an operator by the analysis system which illustrates the manner in which the "Raw" function displays raw data, in the example shown, this is in conjunction with the "Zoom" function.
Figure 33:
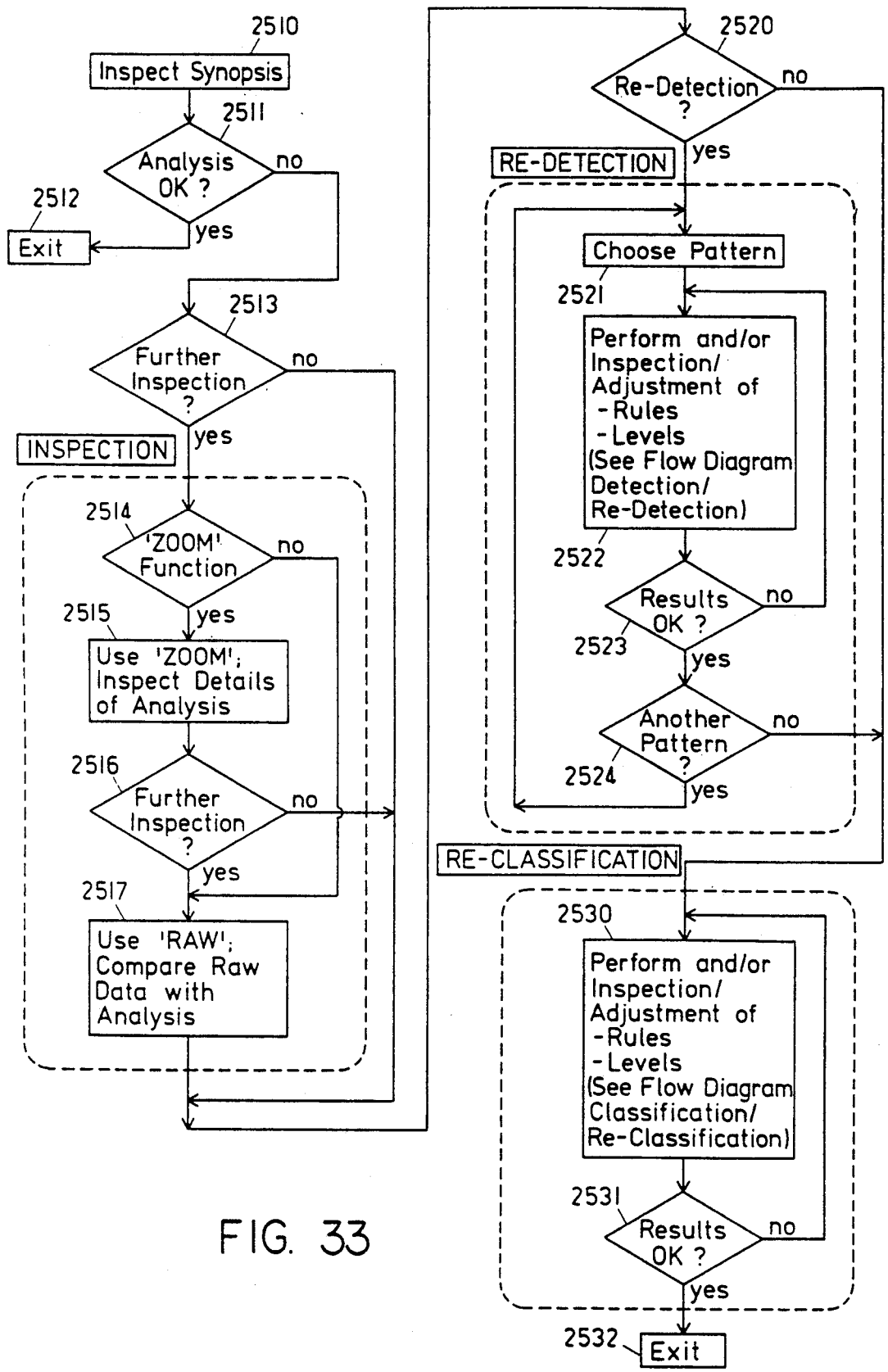
FIG. 33 is a flow diagram showing the program steps carried out by the analysis system during the usage of the re-analysis function.

FIG. 32 shows the manner in which the "Raw" function (in this example, shown in conjunction with the "Zoom" function) allows the operator to inspect the raw data. A particular point in time can be indicated by the operator by using the mouse and cursor pointer to drag the cursor to the desired position 2501 and release the mouse button. Raw data will be recalled from the data disk 27 and displayed on the screen which was recorded over a time span between 5 and 120 seconds, centered around the indicated moment in time. This time span will be illustrated in the Zoom window (or in the synopsis, if the "raw" function is activated without activating the "zoom" function). In the example displayed in FIG. 33, the raw data window obscures the synopsis except for the hypnogram. The raw data is displayed in a common polygraphic format. The time base can be modified by moving the cursor with the mouse to either end of the "scrolling arrow" 2502 and clicking the mouse. Forward and backward paging is lone by pointing with the cursor arrow to one of the associated arrows 2503 and clicking the mouse. The outer arrows correspond to a full page advance, the inner arrows to a half page.

A flow diagram showing the program steps carried out by the analysis system of the invention in using the re-analysis function is shown in FIG. 32. Initially, the program waits to allow the user to inspect the synopsis (2510) and then receive input from the user as to whether the analysis is acceptable (2511). If so, the program exits (2512); if not, the program waits to determine if further inspection is required (2513) and if not avoids any further inspection. If further inspection is required, the program determines whether the Zoom function is chosen (2514). If so, the zoom is used to inspect details of analysis (2515) and a check is made whether further inspection is required (2516). If not, the program avoids further inspection; if so, the program uses the "raw" function to compare the raw data with the analysis (2517) and which is also used if the Zoom function is not chosen. After completion of inspection, the program goes on to the re-detection block and firsts checks to see if re-detection is required (2520) and if not goes immediately to reclassification. If re-detection is required, a pattern is chosen (2521) and detection is performed and adjustments interactively of rules and levels is carried out (2522). If the results are not okay (2523) the program loops back to re-perform the detection and adjustments. If the results are acceptable to the user, the program checks to determine whether another pattern should be redetected (2524). If so, the program loops back to choose another pattern and if not, the program goes on to reclassification. Upon entering re-classification, classification is performed and the adjustment of rules and levels is carried out interactively (2530) and when completed, the program checks to see if the results are acceptable to the user (2531). If not, the program loops back to re-perform classification and adjustment of rules and levels; if the results are acceptable the program exits (2532).

Figures 34A, 34B:
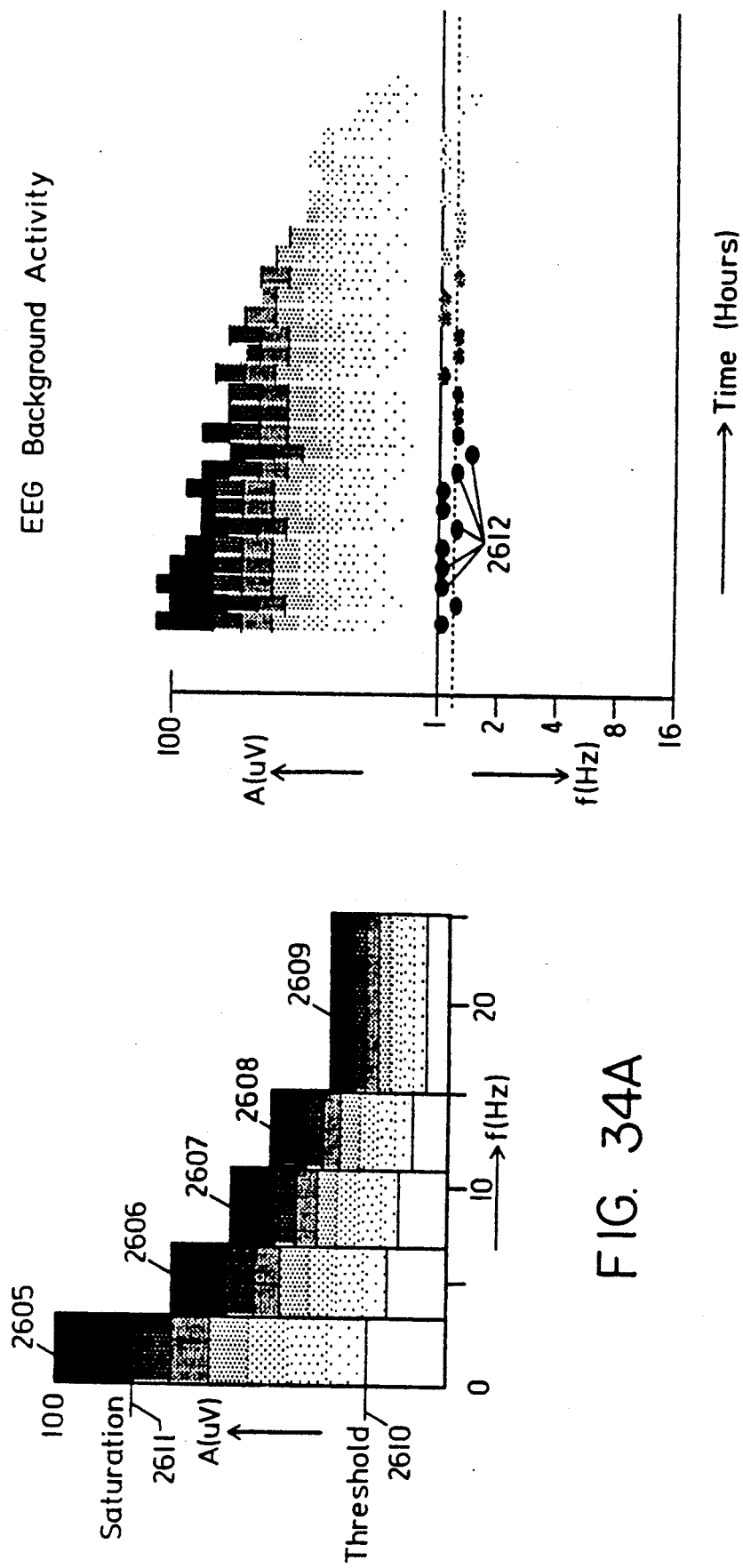
FIGS. 34A and 34B are graphs displayed by the analysis system to the operator which illustrate the principle of the display of rhythmic EEG background activity.

FIG. 34 shows a manner in which the rhythmic EEG background activity can be displayed to the user on the CRT display screen. In FIG. 34b, the horizontal axis corresponds to time and the positive vertical axis corresponds to amplitude in microvolts. The negative vertical axis corresponds to frequency in Hertz. Up to five areas of frequency can be displayed in a linear fashion, for example, with the various areas ranging from 0 to 5 Hertz, from 5 to 10 Hertz, etc. Alternatively, the frequency areas can be displayed in a semi-logarithmic fashion, for example, with consecutive areas going from 0.5 to 1 Hertz, from 1 to 2 Hertz, from 2 to 4 Hertz, etc. Inside the various frequency areas of the semi-logarithmic presentation, the scale is preferably always linear to ease the task of interpretation. As illustrated pictorially in FIG. 34a, different colors denoted 2605-2609 may be used for the display of background activities occuring in the various classical EEG frequency bands. The amplitude of the background activity is preferably indicated using a special type of histogram display. First, for each of the classical frequency bands there is a lower threshold value 2610 and a saturation value 2611 which can be modified by the user. The bottom position of the histogram-bar to be drawn corresponds to the actual frequency plus the threshold. The top position of the histogram-bar corresponds to the actual amplitude. The analysis systems draws the bar on the screen in a manner such that the saturation of the color for each histogram-bar increases as the length of the bar increases proportional with the amplitude. The frequency of the background activity is indicated for each histogram with a dot 2612 having the appropriate color and a saturation that corresponds to the amplitude. As a consequence of this method of display, minimal redundancy is created, inasmuch as the amplitude of a certain background rhythm decreases, it gradually vanishes and so does the dot indicating the corresponding frequencies.

Figure 35:
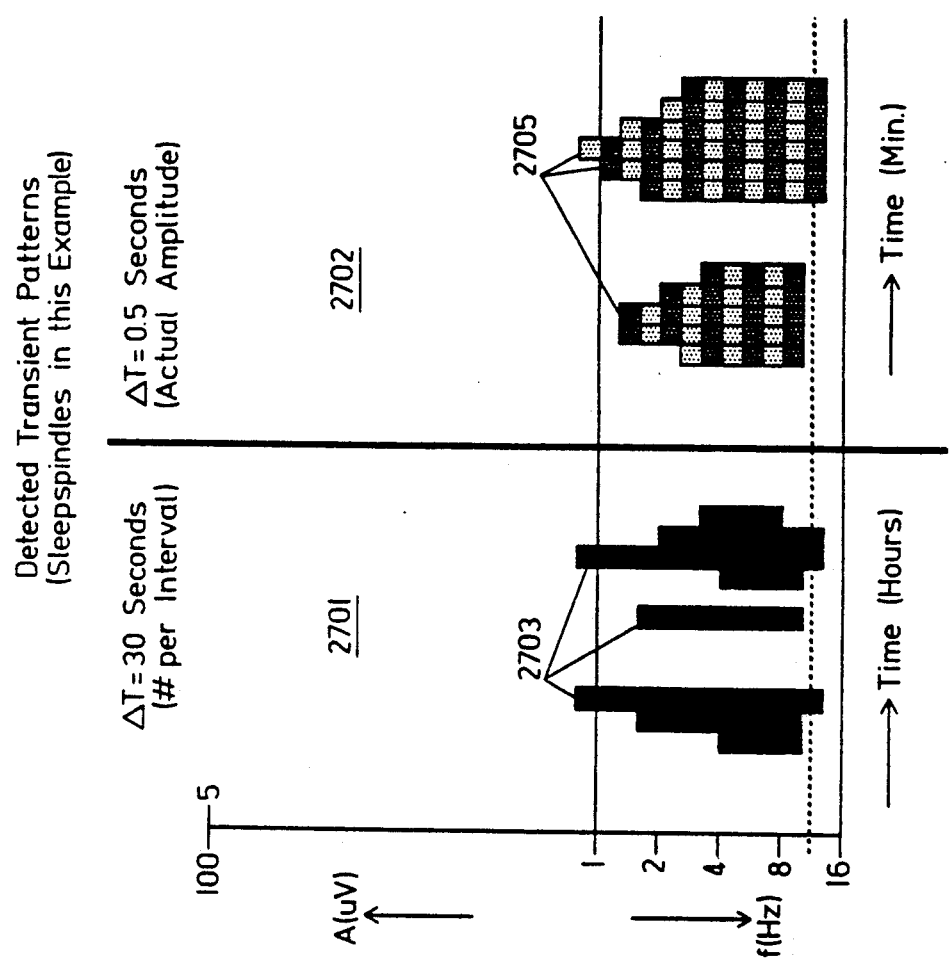
FIG. 35 is a display provided by the analysis system to the operator which illustrates the principle of the display of detected transient EEG patterns for 2 typical timebases.

FIG. 35 illustrates the display provided by the analyzer system for showing detected transient EEG patterns for two typical timebases which are designated 2701 and 2702. The display of the two patterns is differentiated according to the time resolution used, 30 seconds in one case and 0.5 second in the other case. If the interval time exceeds the time duration of a particular pattern, for example, the timebase pattern 2701, then the number of patterns within such an interval is indicated using a regular histogram display indicated at 2703 in FIG. 35. The bottom position of the bar in this display corresponds to the (mean) frequency of the patterns in the interval, and the length corresponds to the number of patterns per interval. If, on the other hand, the interval time of the resolution is shorter than the duration of a particular pattern, such as may be the case for the time base 2702, then its actual amplitude is indicated using a histogram display alternating between two saturations levels of a color as indicated by the histogram bar 2705 in FIG. 35. The bottom position of the histogram bar again corresponds to the actual frequency and the length of the bar to the actual amplitude in microvolts.

Figure 36:
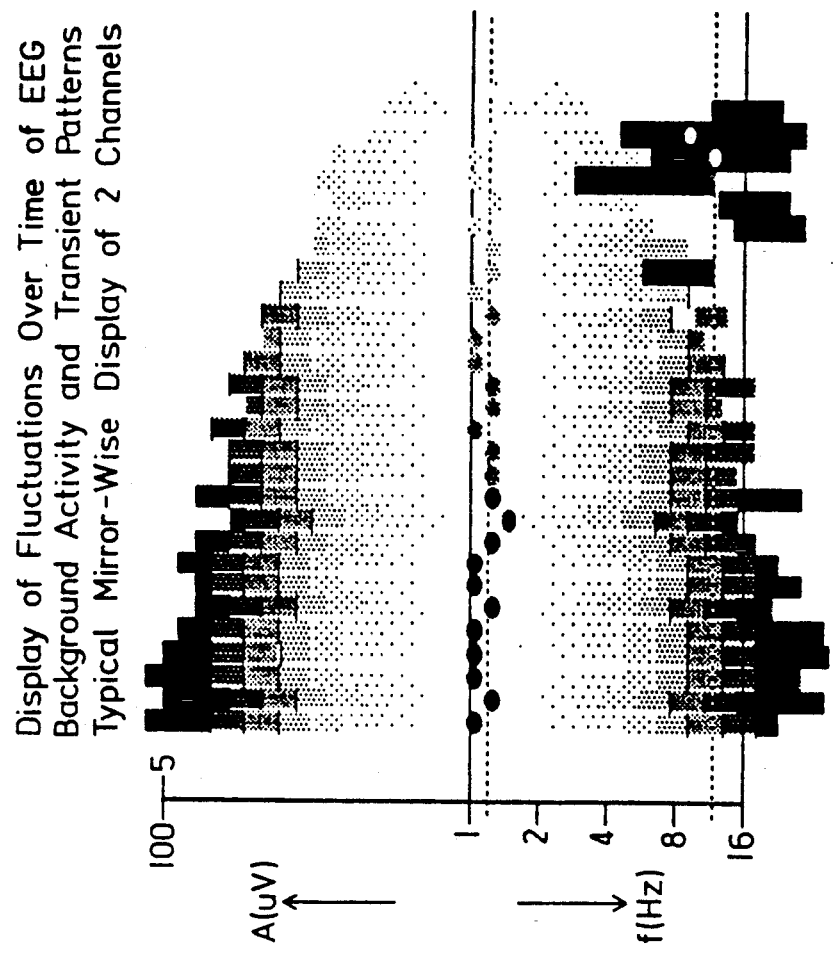
FIG. 36 is a display provided to an operator by the analysis system which illustrates the principle of display of combined EEG channels in a mirrored fashion.

FIG. 36 shows an illustrative display by the analysis system of combined EEG channels. The various EEG channels can be displayed individually or combined; if combined, it is possible to provide mirror-wise display of two channels and/or ensemble averaging of the analyzed data over indicated EEG channels prior to regular or mirror-wise display. A mirror-wise display of the two channels is illustrated in FIG. 36.

Figure 37:
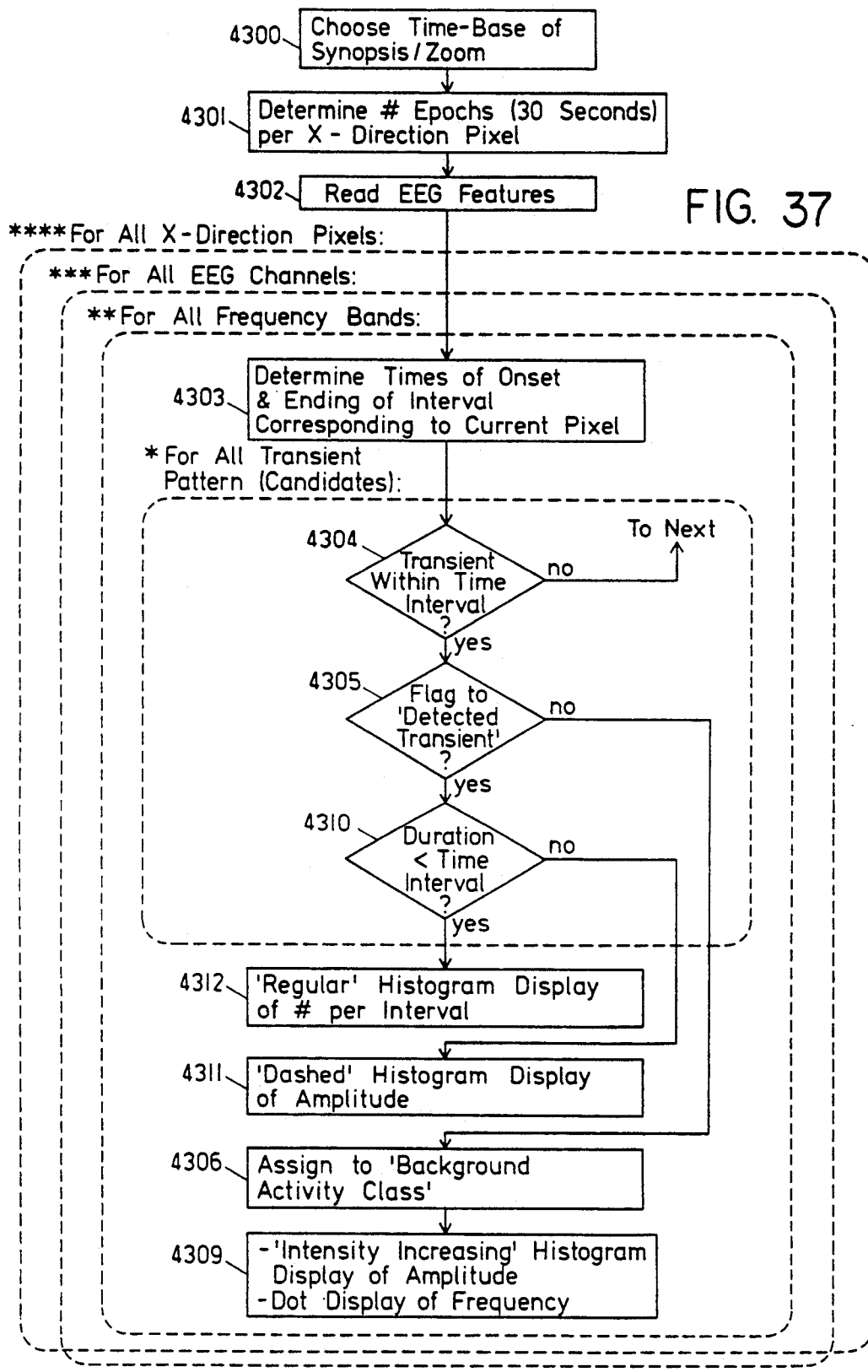
FIG. 37 is a flow diagram showing the program steps carried out by the analysis system during the EEG display.

A flow diagram of the program steps carried out by the analysis system for analyzed EEG display is shown in FIG. 37. The program first checks to determine the time-base selected by the operator for the Synopsis/Zoom (4300) and then determines the numbner of epochs (30 seconds long) per x-direction pixel (4301). The EEG features are then read (4302) and the times of onset and ending of the interval corresponding to the current pixel are determined (4303). A determination is then made whether the transient pattern candidate is within the time interval (4304) and if not, the program goes on to the next pixel. If so, the program determines if a flag is set to "detect a transient" (4305), and if not, the candidate is assigned to "background activity class" (4306) and there ia sn "intensity increasing" histogram display of amplitude and a dot display of frequency (4309). If the flag is not set at 4305, a check is then made to determine whether the duration is less than the time interval (4310) and if not a "dashed" histogram display of amplitude is made (4311). If at the decision point 4310 it is found that the duration is less than the time interval, a "regular" histogram display of the number per interval is made (4312). These program steps are than repeated for all frequency bands, for all EGG channels, and for all x-direction pixels.

Figure 38:
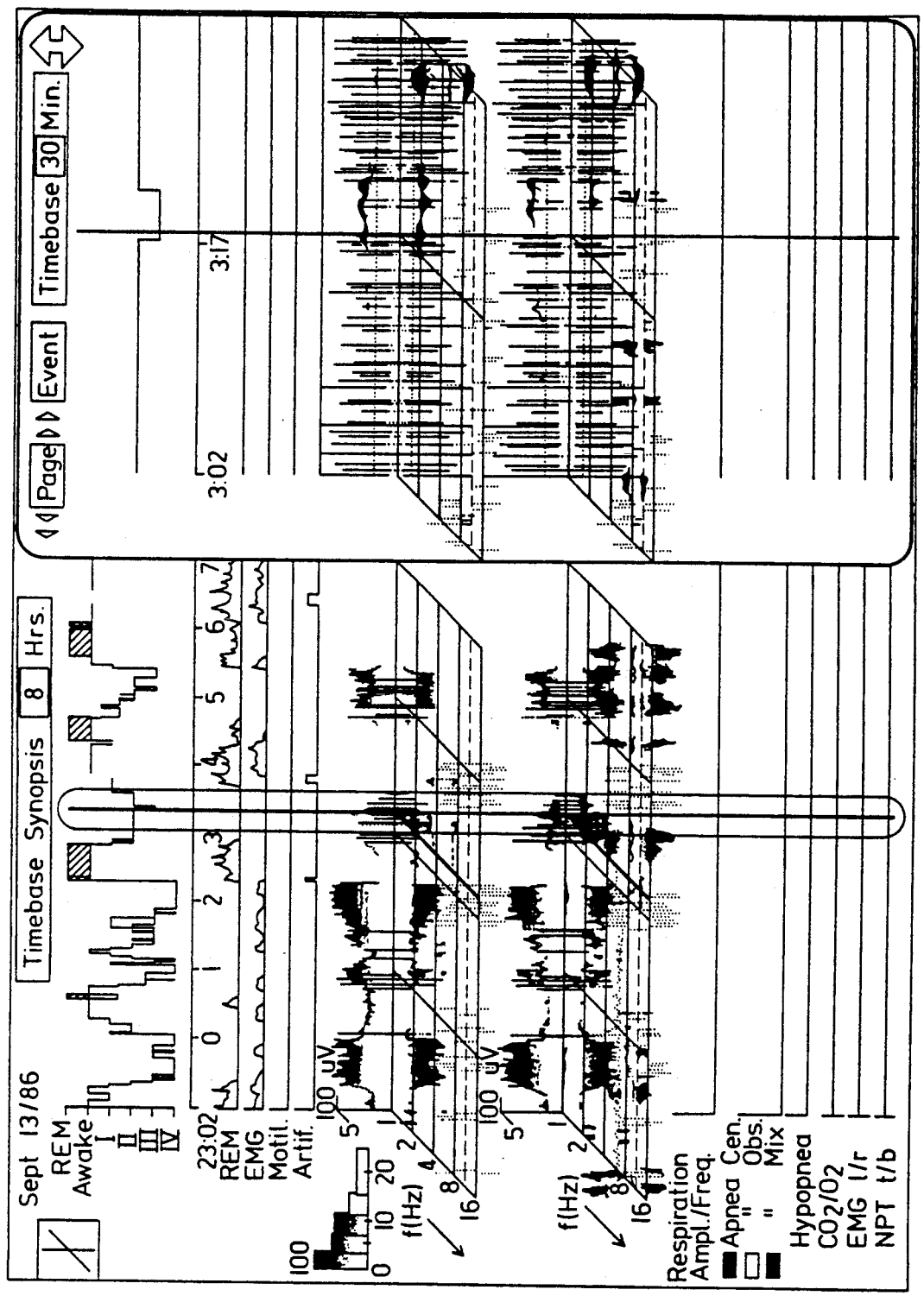
FIG. 38 is the form of a display provided by the analysis system to an operator which illustrates a synopsis over half the screen in combination with a "Zoom" display.

FIG. 38 is an illustration of the display by the system of a synopsis over one half of the screen in conjunction with a Zoom display over the other half of the screen which illustrates the special type of EEG display and the effects of the zoom function. The quasi 3-d presentation of time, frequency and amplitude aspects of the EEG is shown for exemplification of the display capabilities. If the 3-d mode is not selected, the default condition of the display will be in 2 dimensions. The positive veritcal axis of the EEG represents amplitude and number of detected patterns in an interval corresponding to the resolution. The frequency axis is vertical and skewed in this example. For purposes of clarity of illustration, only four frequency areas are shown here and the logarithmic frequency axis is chosen ranging from 1 to 16 Hertz. Preferably, different colors are used for each of the various frequency bands. The intensity of the colors is drawn on the color monitor proportional to amplitude. Symmetrical leads are displayed in a mirrorwise fashion. By presenting EEG data in this manner, periods of deep sleep will be predominently intense blue, light sleep will show yellow colored spindle activity and blue colored K-complexes, a period of awake will be predominately red, and REM sleep will be overall white. The Zoom window in this example covers 30 minutes. The increase of resolution has the effect that individual K-complexes (blue histograms) and short lasting (red-color) alpha bursts become visible, thus revealing possible microarousals.

Figure 39:
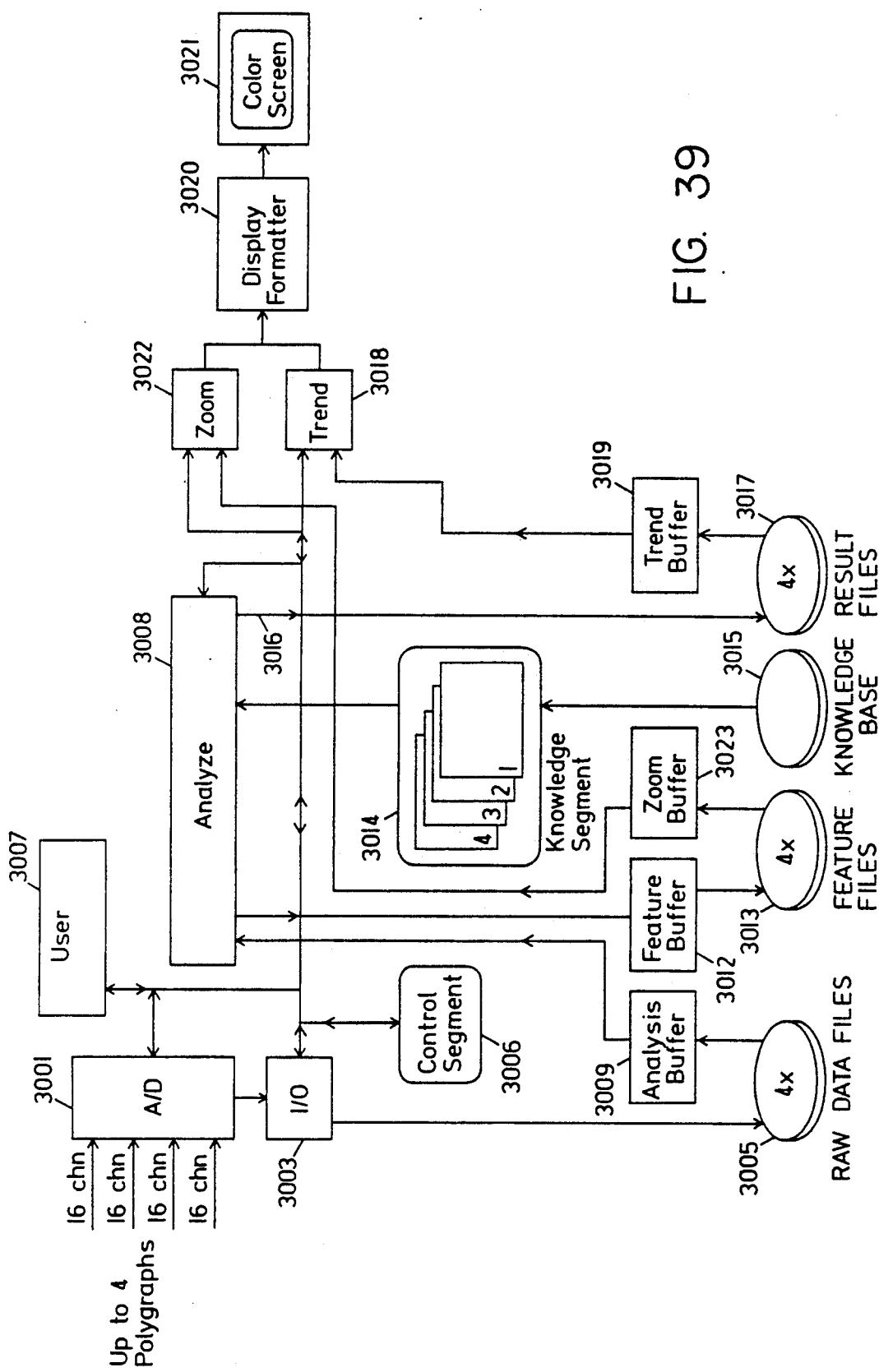
FIG. 39 is a block diagram of the functional steps performed during recording and on-line analysis, which shows the manner in which the Trend and Zoom functions are implemented.

The functional components of the system and their interaction during data acquistion and on line analysis for several subjects is shown illustratively in block diagram form in FIG. 39, and include operation of the Trend and Zoom functions. It is to be understood that the blocks and symbols shown in FIG. 39 are functional and do not necessarily correspond with any of the physical hardware components shown in FIG. 1, but may be carried out by one or more of those hardware components. The blocks shown in FIG. 39 essentially illustrate major process steps or groups of steps rather than hardware units. With reference to the figure, the input data from the multiple input channels from the several subjects is provided to an autonomous analog to digital process 3001 which samples the high level (1 volt IRIG level) analog output signals from several polygraphs or physiological amplifiers. In the preferred embodiment, the number of polygraphs can be selected from 1 to 4, but that number can be higher without fundamental changes in the operational system. In the preferred embodiment, the number of channels per polygraph is between and 4 and 16, but this number can also be increased without fundamental changes in the system. The analog signals can also be acquired from an analog tape recorder, which allows replay speed of perhaps up to 64 times the recording speed. After digitization in the converter 3001, the samples are stored in a buffer and submitted to an I/O process 3003 when the buffer is filled. A second buffer of equal size will be made available to the A/D process 3001 which is then filled with subsequent samples while the I/O process 3003 stores the samples of the first buffer in a Raw Data File 3005 on a disk, using a separate file for each subject.

A central control segment 3006 contains all the necessary control variables to synchronize the various processes. All the available processes have access to it to organize their interactions. The User Interface 3007 provides the initiation of the processing and channels all possible user intervention and selections. It is capable of interaction with the Control Segment 3006 and can also send messages to all of the available processes directly. Another autonomous Analyze process 3008 embodies all data analysis functions such as feature extraction, pattern detection and classification of sleep, respiration and other physiological variables. It obtains its input via an Analysis Buffer 3009 from the Raw Data Files 3005. The first step in the Analyze process 3008 is the feature extraction, i.e., the predetection of all defined transient patterns and the estimation of the background activity. The results of this are stored via a Feature Buffer 3012 in a Feature File 3013, using a separate file for each subject. Subsequently, the features (from the transient pattern candidates) are detected using the detection criteria read from Knowledge Segment 3014. Each of the subjects from whom recordings are taken has a separate set of criteria for pattern detection and classification of sleep and respiration. The criteria for each subject are selected prior to analysis from the Knowledge Base File 3015. The results from the pattern detection are stored in Feature Files 3013 and, together with the classifications, into a Result Files 3017, using a separate file for each subject. This constitutes the final point of the actual analysis. If via User Interface 3007 the Trend function is activated for one or more subjects the Trend process 3018 becomes active. It will read via Trend Buffer 3019 the analysis results from the appropriate Result Files 3017. Depending on various display parameters such as the requested timebase that are specified via User Interface 3007 and contained in Control Segment 3006, the Trend process 3018 submits the analysis results to Display Formatter 3020 which will produce the appropriate Trend (synoptical) display on Color Display monitor 3021. If via User Interface 3007 the Zoom function is activated, the Zoom process 3022 becomes active. It will read via Zoom buffer 3023 the appropriately integrated features from Feature File 3013. Depending on the requested zoom parameters, ( e.g., timebase) the data are submitted to Display Formatter 3020 which will produce the appropriate Zoom display in relation to the existing trend display on Color Display Monitor 3021.

Figure 40:
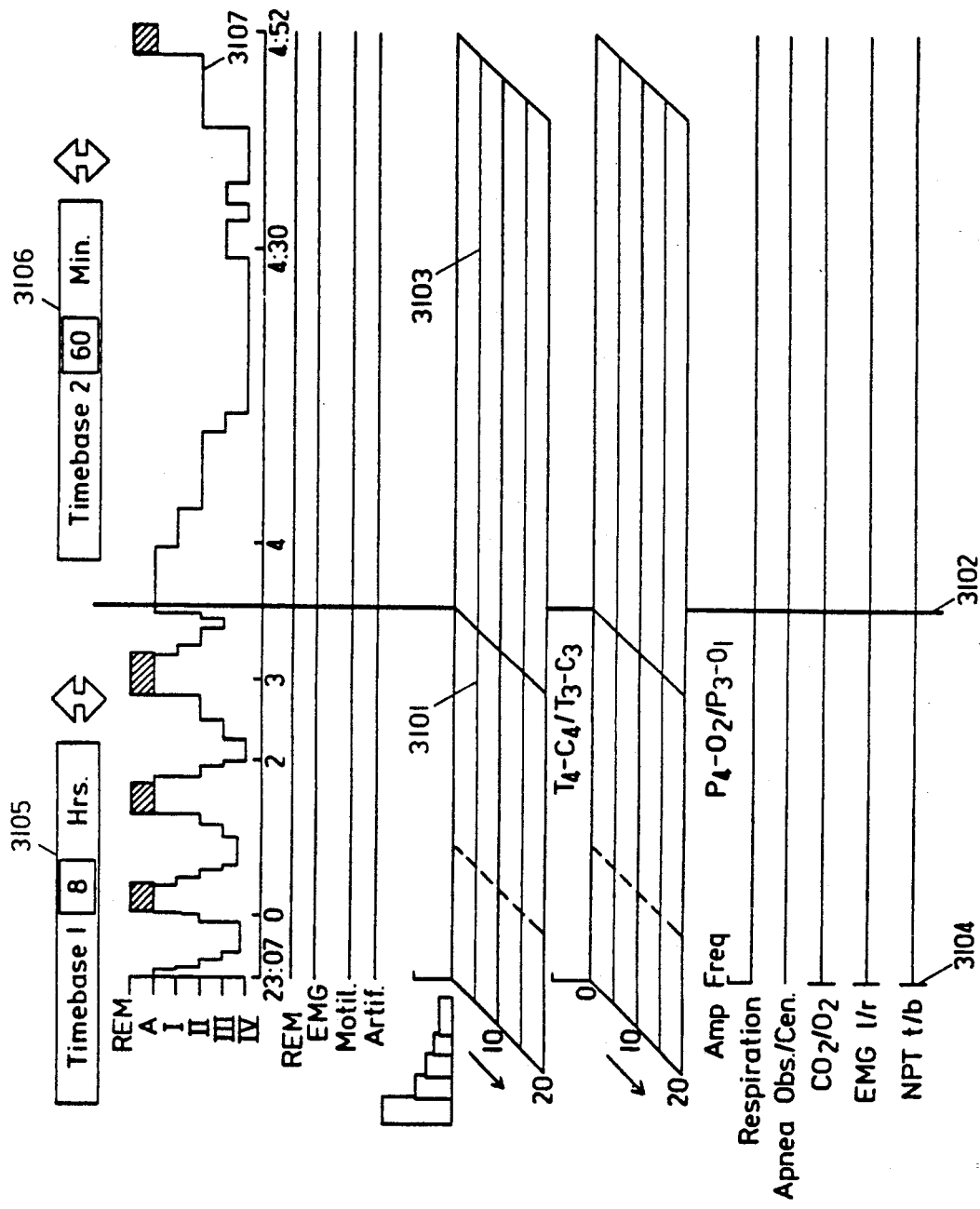
FIG. 40 is a display provided by the analysis system to an operator which illustrates the on-line trend display for one subject.

FIG. 40 shows a display screen provided for a typical on-line Trend display for a single subject. Shown in FIG. 40 is the dual-timebase display used to facilitate assesment of both long term fluctuations and short term fluctuations over the relatively "recent" past. With the major exception of the dual-timebase feature, the Trend display is similar to the synoptical display of FIG. 30. An additional difference is that in FIG. 40 the EEG background and patterns are displayed in a quasi-3 dimensional fashion. On the left side of the break point 3102 between the two time bases, the earlier part of the synoptical analysis results 3101 are displayed on the standard time base. On the right hand side of the break point 3102, the most recent part of the synoptical analysis results 3103 are displayed on an expanded time base. The start of the analysis period 3104 is displayed at the very left hand side of the standard timebase. The actual value for the standard timebase can be specified using a scrolling value bar 3105, with the user increasing or decreasing the timebase by using the cursor pointer positioned on the up or down arrows associated with the scrolling value bar. Similarly, the actual value for the expanded timebase can be specified using the scrolling value bar 3106. Typically, every 30 seconds new analysis points are added to the very right hand side of the expanded time base at the position 3107 and corresponding analysis points are shifted off of the left hand side of the expanded timebase into the right hand side of the standard timebase.

Figure 41:
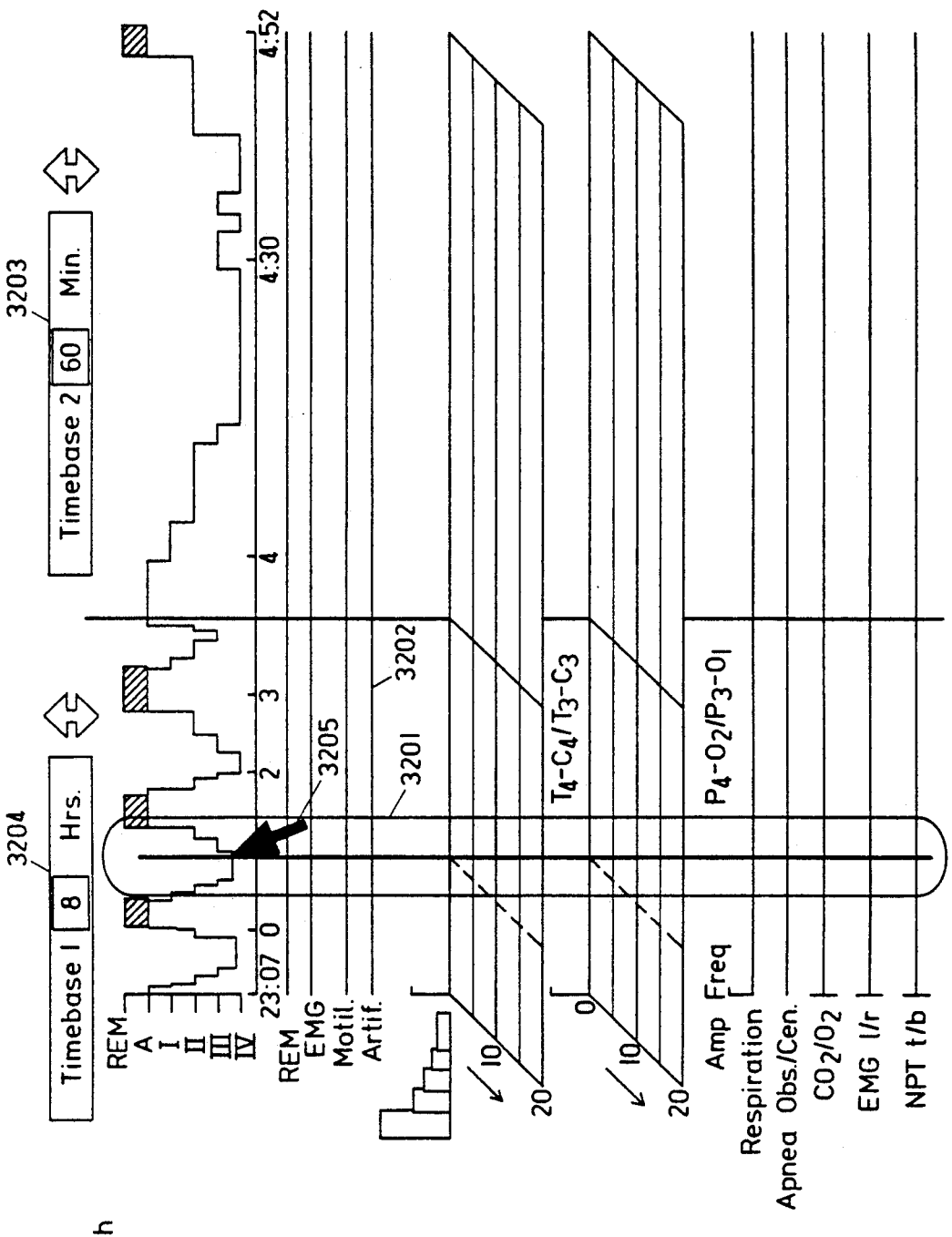
FIG. 41 is a display provided by the analysis system to an operator which illustrates the initiation of the Zoom function.

FIG. 41 illustrates the manner in which, after activation of the Zoom function, a moment in time is indicated in the standard time base part of the Trend display. After activation of the Zoom function, Zoom Indication Window 3201 becomes visible superimposed on the standard timebase part 3202 of the Trend Display. The time-width of the Zoom Indication window is equal to the selected expanded timebase 3203, projected onto the standard timebase 3204. Using the mouse and cursor 3205, the Zoom Indication window can be dragged to any position within the standard time base part 3202 of the Trend display. Release of the mouse button will register the Zoom Indication window position.

Figure 42:
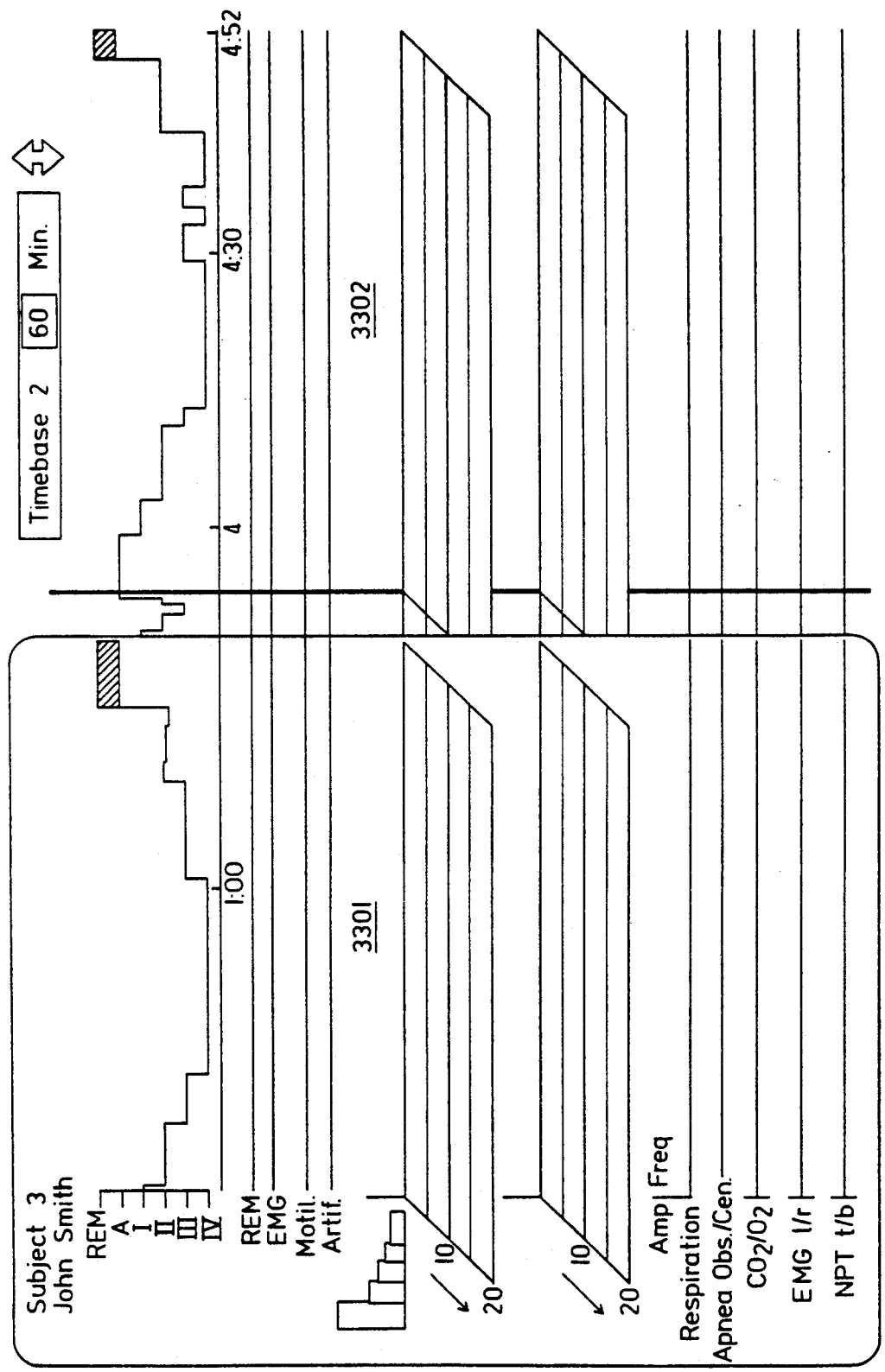
FIG. 42 is a display provided by the analysis system to an operator which illustrates the Zoom function.

The illustrative CRT screen display of FIG. 42 shows how by using the Zoom function and Trend display, the information derived from the most recent past 3302 can be compared with a period from the earlier part of the analysis 3301, which is now displayed on the same time base.

Figure 43:
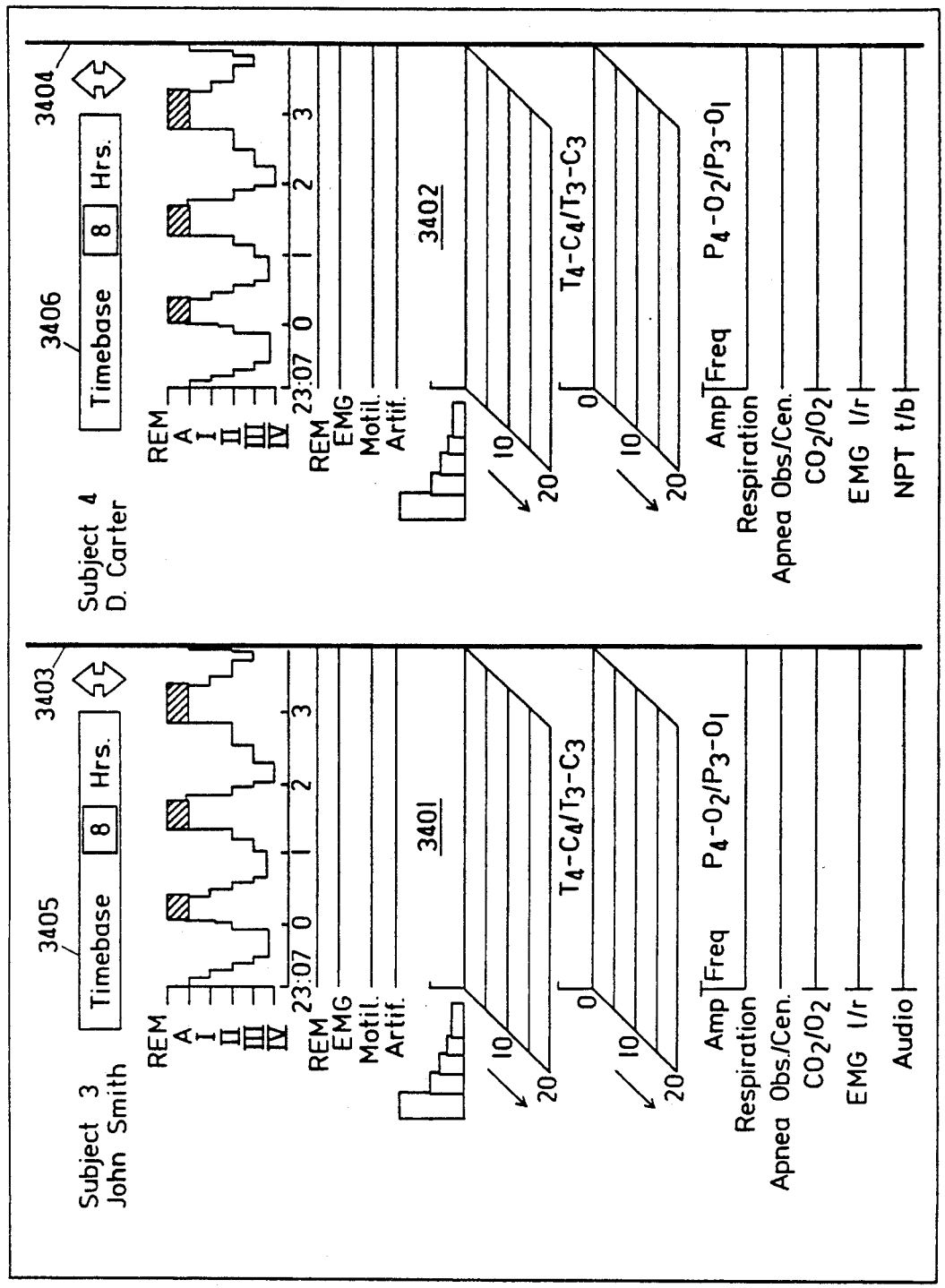
FIG. 43 is a display provided by the analysis system to an operator which illustrates the Trend function for two subjects simultaneously.

FIG. 43 is an illustrative CRT screen which shows how the synoptical Trend display of analysis results can be shown for two subjects simultaneously. On the left hand side of the display screen, the synoptical analysis results 3401 of one subject are displayed. The synoptical analysis results 3402 for another subject are displayed simultaneously on the right hand side of the screen. Typically, every epoch (e.g. every 30 seconds) new analysis points are added to the right hand side of the Trend display of the first subject at point 3403. Consequently, the whole Trend display shifts to the left side. The same happens for the other subject at the point 3404. The timebase for the Trend display of both subjects can be selected independently. A scrolling value bar 3405 displayed on the screen can be used with the mouse and cursor to select the timebase for the first subject, and a second scrolling value bar 3406 can be used with mouse and cursor to select the timebase for the other subject.

Figure 44:
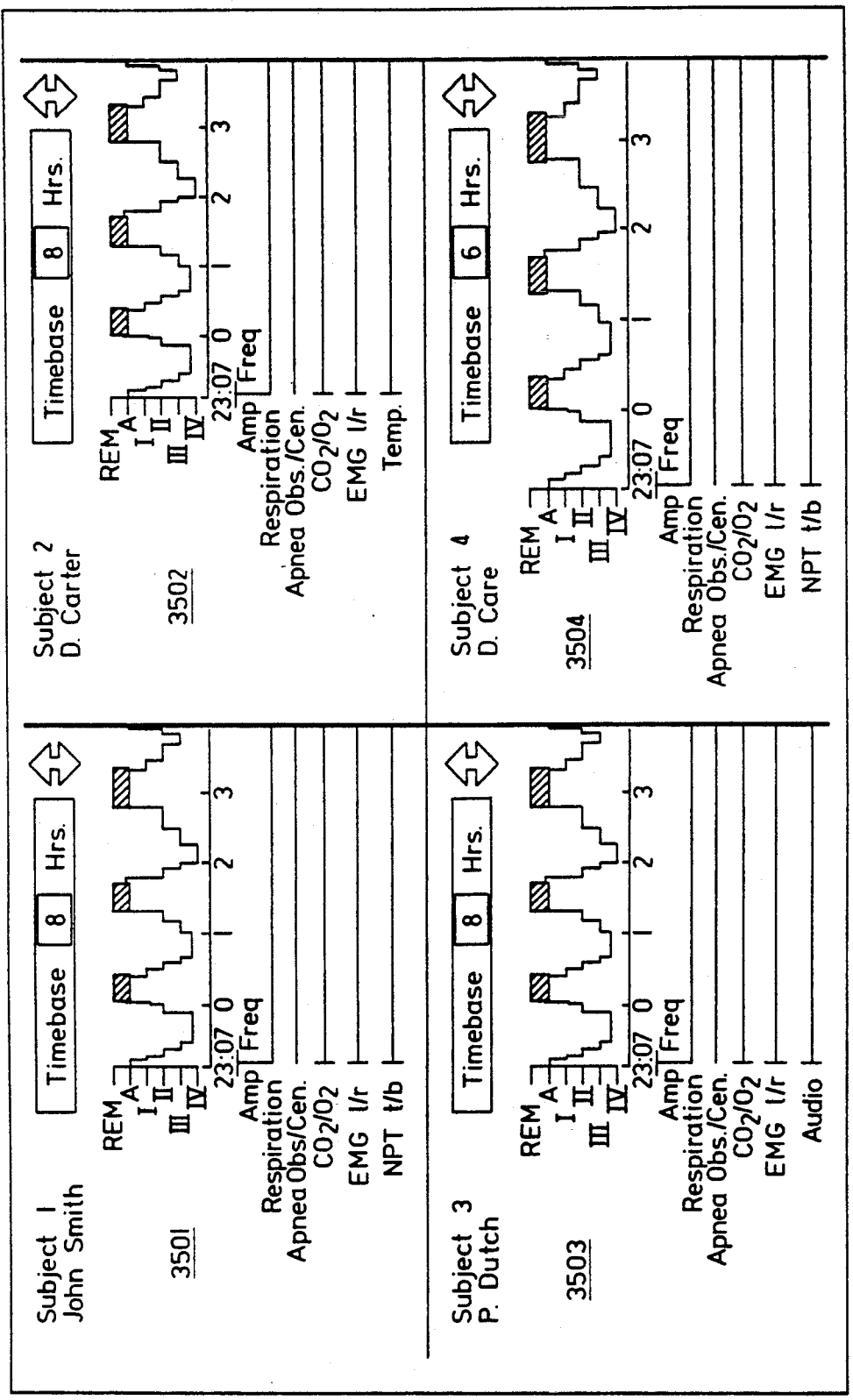
FIG. 44 is a display provided by the analysis system to an operator which illustrates the Trend function for 4 subjects simultaneously.

The illustrative CRT display screen of FIG. 44 shows the manner in which the synoptical Trend display of analysis results can be displayed for 4 subjects simultaneously. With respect to Trending of one or two subjects simultaneously, only half the display height is available. This typically implies that fewer variables may be displayed per subject, although this result is not necessary at the expense of display size. The results displayed in the manner of adjusting the timebase are the same as described above for the display of FIG. 41 for two subjects. The synoptical display 3501 shows analysis results from subject 1, display 3502 shows analysis results from subject 2, display 3503 shows analysis results from subject 3, and display 3504 shows analysis results from subject 4. The timebase for each subject can be selected independently of the timebase for the other subjects.

Figure 45:
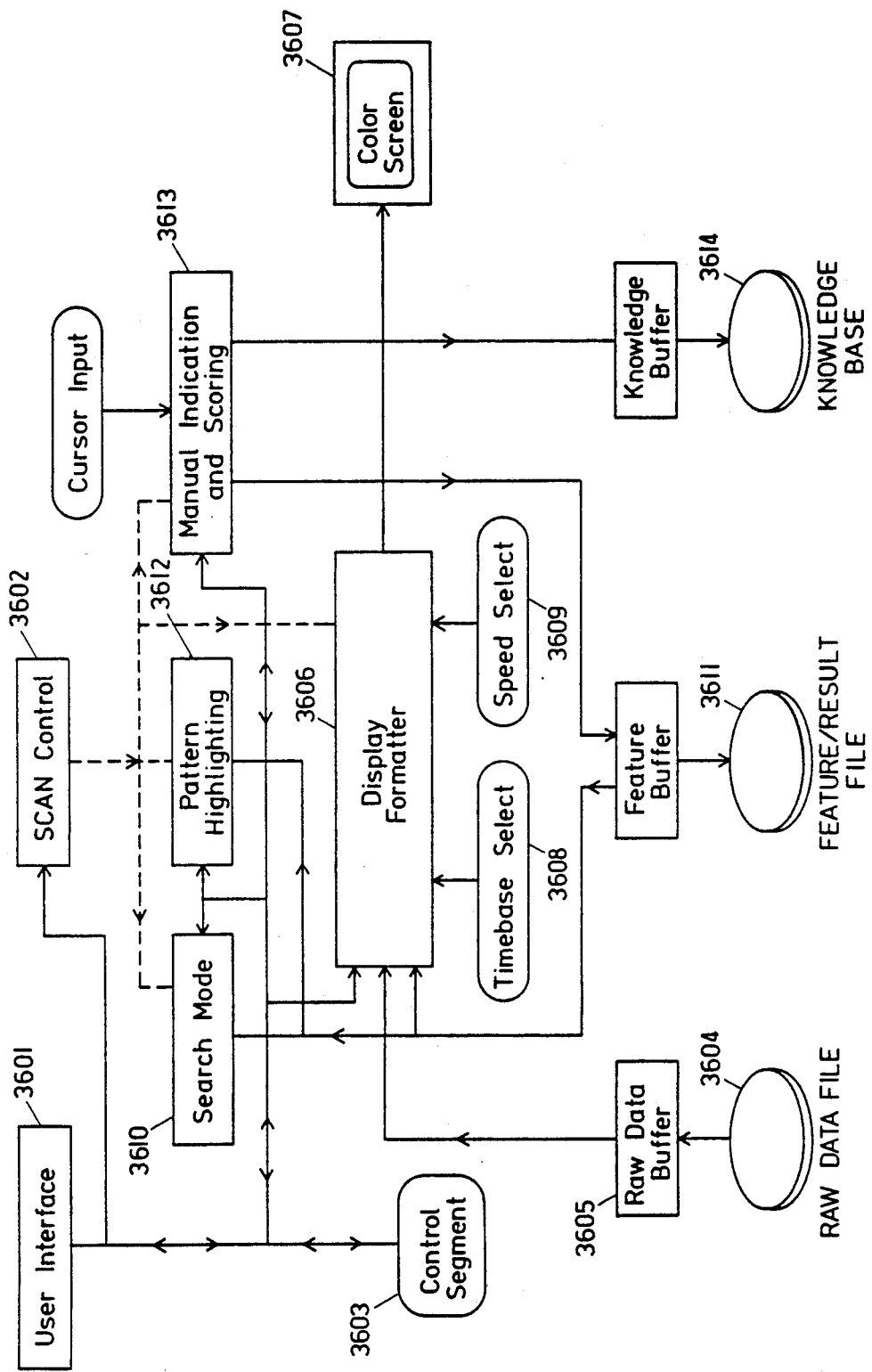
FIG. 45 is a block diagram illustrating the functional components of the system during the Scan function which allows raw input data to be visually explored in relationship to the results of the analysis.

The functional components of the analysis system during the Scan function are illustrated in FIG. 45. During the Scan function, raw input data can be visually explored in relationship to the results of the analysis. The same general User Interface Process 3601 that was described with respect to FIG. 39 (User Interface 3007) allows selection of the Scan function. All functions carried out are controlled from a central Scan Control Process 3602 that initiates various subprocesses via Control Segment 3603. The input to Scan control consists of messages from User Interface 3601, passed again via Control Segment 3603. Thus, through this path the operator can select and terminate the various subfunctions. The most basic subfunction is the display of the raw input data in either "page" or "scroll" modes. The raw input (recorded) data is read from the Raw Data File 3604, via buffer 3605. This data is submitted to a Display Formatter 3606, which implements the actual display of the data on the Color Graphics Screen 3607. The Display Formatter displays the data in either "page" or "scroll" mode depending on the mode requested via the User Interface 3601 and reflected in Control Segment 3603. Display Formatter 3606 gets additional input from Time Base Selector 3608 and Speed/Direction Selector 3609. Time Base Selector 3608 determines the time base over which the raw data is displayed on the screen. Speed/direction selector 3609 determines the direction in which the display of the raw data is updated, either forwardly or backwardly in time, and the speed with which the display updates occur.

Another subfunction is the Search Mode. The Search Mode subfunction 3610 accepts various types of events that each specify a time instant in the Raw Data File for which the search is to be made. In the prefered embodiment, the Search Mode accepts (1) a moment in time, within the recording period, specified in an "hour: minute: second" format (e.g., 3: 12: 00 am), (2) a moment in time indicated with a cursor along the time axis of the hypnogram, displayed simultaneously with the raw data, (3) the next or previous occurrence of a pattern (e.g., sleepspindle) with respect to the current position, (4) the next or previous occurance of the onset of a sleep stage (e.g., REM) with respect to the current position, (5) the next or previous occurrence of an "event" (e.g., CPAP applied) with respect to the current position, and (6) the next or previous occurrence of a respiratory disturbance such as an apnea or hypopnea in the context of the current position. Other events or combinations of events can be added in a similar fashion. Depending on the specified event, the Search Mode subfunction 3610 will access the Feature or Result File 3611 to search for the occurrence of such an event, compute the corresponding position in Raw Data File 3604, and instruct Display Formatter 3606 to display this raw data on the Color Screen 3607.

Another subfunction is Pattern Highlighting 3612. If the Pattern Highlighting subfunction is activated, it will search in Feature File 3611 for the occurrence of detected patterns (e.g., K-complexes, sleepspindles, Rapid Eye Movements) within the currently displayed raw data on the Color Screen 3607. If, during analysis, patterns were detected within the displayed interval, they are highlighted in the raw data on the screen with the same color which was used for such patterns in the synoptical display of the analysis results. If the raw data are updated on the screen in either the "page" or "scroll" mode, all detected patterns are highlighted in such a manner as long as they appear on the Color Graphics Screen 3607. The Pattern Highlighting subfunction 3612 will also highlight occurances of apnea and hypopnea and will indicate the sleep stage that was classified for the current raw data on the screen.

Another subfunction is Manual Indication and Scoring 3613. With this subfunction, transient patterns, for example, K-complexes, can be indicated manually on the Color Screen 3607 by means of a graphical cursor. In addition, the classification for the currently displayed raw data epoch can be indicated. This can be done so as to overrule part of a previously performed automated analysis of sleep or respiration data. The manually indicated patterns and classifications are marked as such and appear with a different color in the appropriate curves of the synoptical display of the analysis results. The Manual Indication and Classification subfunction 3613 is also capable of performing indications of patterns and classifications on a raw data file that was not analyzed previously. In so doing, it can serve as a supervised learning device to establish new criteria based on the indicated patterns and classifications. The newly established criteria can be stored in Knowledge Base 3614 to be used for subsequent analysis or combined with other criteria to establish group criteria.

Figure 46:
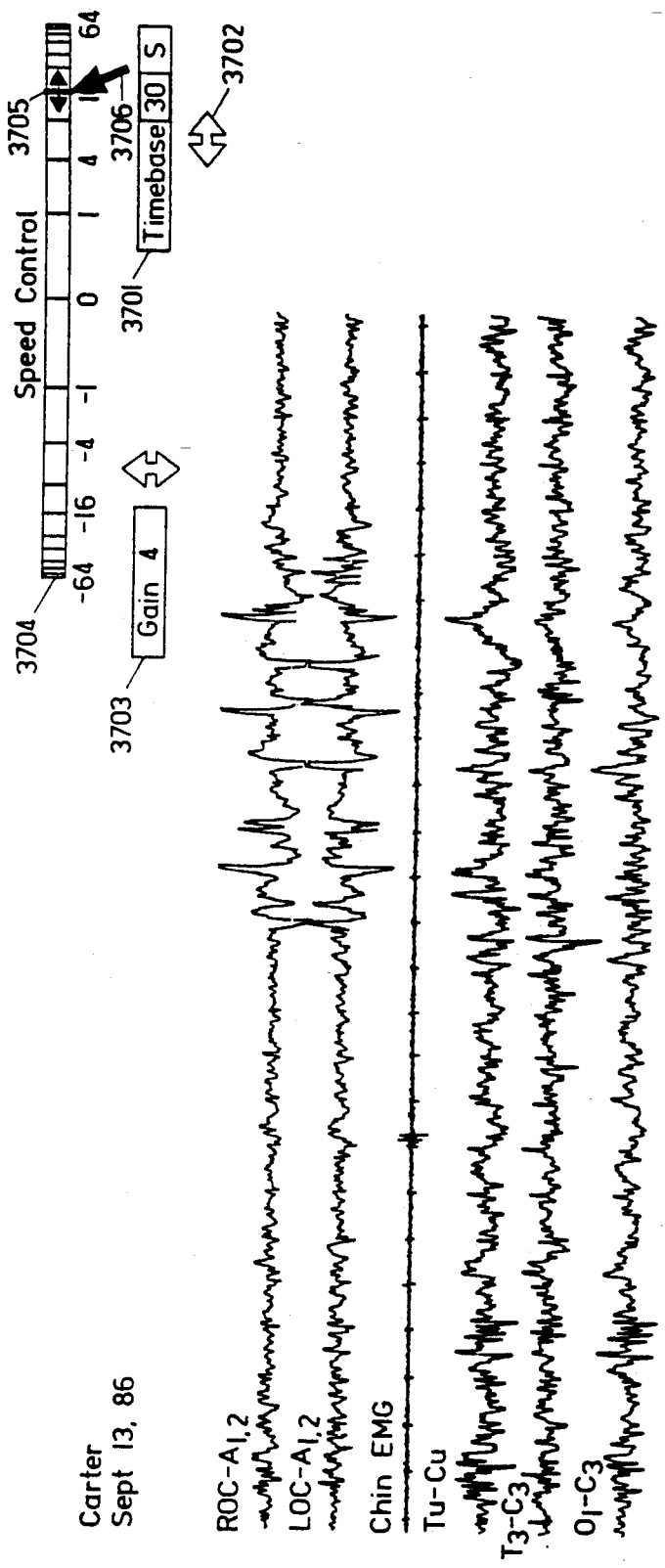
FIG. 46 is a display provided to an operator by the analysis system which illustrates a typical example of the preferred operation of the Scan function, reflecting the display on the colorgraphics screen during a regular scan of raw data in either the "page" or "scroll" mode.

FIG. 46 is an illustrative screen display of a typical example of the preferred manner of implementation of the Scan function showing the data on the Color Graphics Screen during a regular scanning of raw data in either the "page" or "scroll" mode. The middle part of the screen shows a ten channel recording of data, reflecting a traditional polysomnographic recording on paper. A time base selection bar 3701 allows the user to select by use of the cursor and mouse an instantaneous selection of the timebase, corresponding to the elapsed time displayed over the whole width of the display screen. The time base is selected by "clicking" on either side of a selection arrow 3702 with a graphical cursor controlled by a graphical input device such as a "mouse". Clicking on the left side of the arrow 3702 decreases the timebase while clicking on the right side increases the timebase within a range of predefined values. A displayed gain selection bar 3703 allows instantaneous selection of the vertical display gain of the raw input data, using the double arrow. Clicking the upper arrow will increase and clicking the lower arrow will decrease the number of pixels over which each data channel is displayed. Speed and Direction control bar 3704 allows the instantaneous selection of the speed with which the raw input data display is updated on the screen. In the preferred embodiment, the bar 3704 has a symmetrical range of update speeds with zero speed (static display) in the middle. The left half of the bar reflects a range of update speeds ranging from 0 to 64 times real time for backwards scanning through the recorded data, i.e., backward in time. The right half of the bar reflects the same range of update speeds for forward scanning of the recorded data, i.e., forward in time. At any point in time a Marker 3705 is displayed on the bar 3704 to indicate the currently selected display update speed and direction. By means of a cursor 3706, the Marker 3705 can be picked up and "dragged" to a new position to select another update speed and/or direction. The Emulated Paper Speed Indication 3707 reflects the equivalent paper speed based on the selected timebase and a page of standard EEG recording paper that is 30 centimeters wide.

Figure 47:
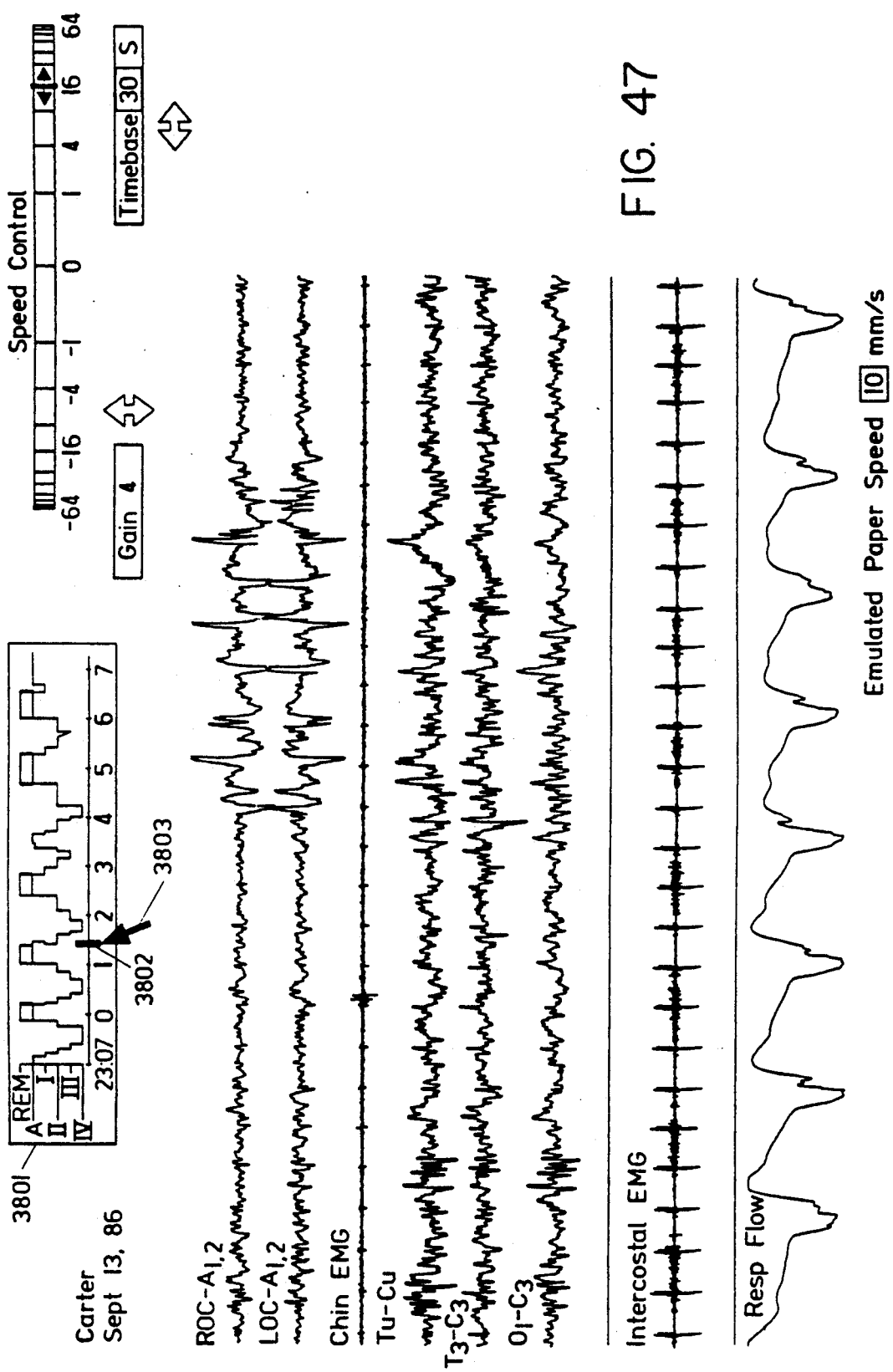
FIG. 47 is a display provided by the analysis system to an operator illustrating one of the possible forms of the Search mode display.

FIG. 47 shows a display screen illustrating one of the possible forms of the displayed data in the Search Mode. The inset labeled 3801 shows the hypnogram that is the result of the sleep analysis and classification of the full recording. The moment in time that corresponds with the currently displayed raw input data in the middle of the screen is indicated with a marker 3802 on the horizontal time axis of the hypnogram. By means of the cursor 3803, the Marker 3802 can be "dragged" to any position on the time axis of the hypnogram. Releasing the cursor will cause the Search function to search for the data in the Raw Data File that corresponds with the newly indicated moment in time and will display those data on the Color Screen.

Figure 48:
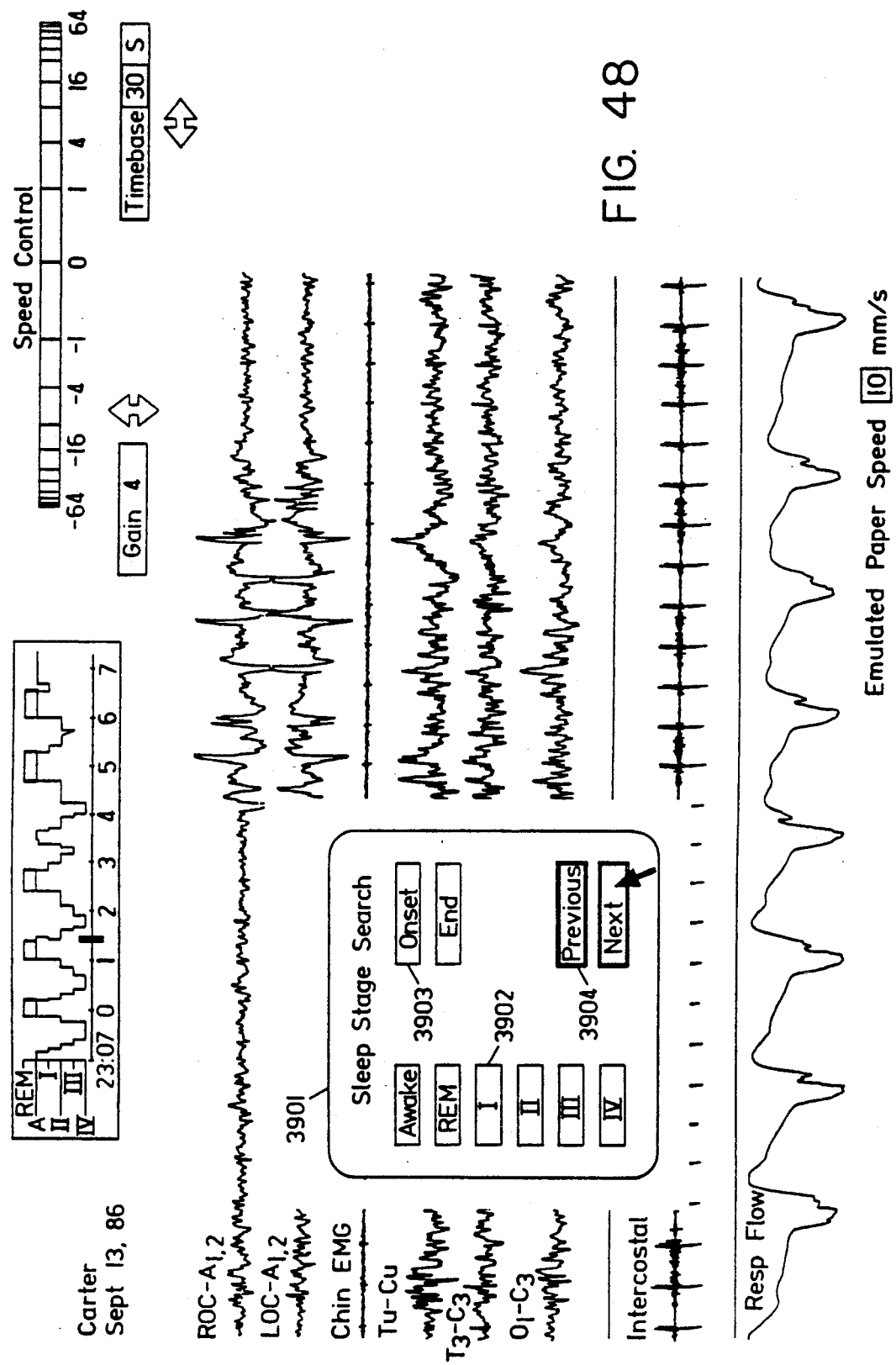
FIG. 48 is a display provided by the analysis system to an operator illustrating another class of Search Mode features, the search for the occurence of a specific event.

FIG. 48 is a display screen which illustrates another function in the Search mode, the search for the occurrence of a specific event. The present invention supports the search for various event types, with this figure illustrating the search for the onset or end of a classified sleep stage. After activating this function via the User Interface, a pop-up window 3901 is created that allows for the selection of the event for which search is to be made. A stack of possible sleep stages 3902 allows for the selection of 1 stage, and in this case as an example REM is selected. The Function Group 3903 allows the specification of search for either the onset or end of the selected sleep stage. Finally, Function Group 3904 allows specification of the search direction with respect to the position of the raw data currently being displayed on the screen. Immediately after a selection is made in the Function Group 3904, the search starts through the Result File for the occurrence of the selected event; if it is found, the corresponding raw data are displayed on the screen. The prefered embodiment of the present invention contains this function plus similar search functions for (1) the occurrence of general transient patterns (e.g., K-complexes) detected in the polysomnographic recording, (2) the occurrence of respiratory events such as apnea, hypopnea, etc., and (3) the occurrence of manually or automatically entered "events" (e.g., CPAP applied).

Figure 49:
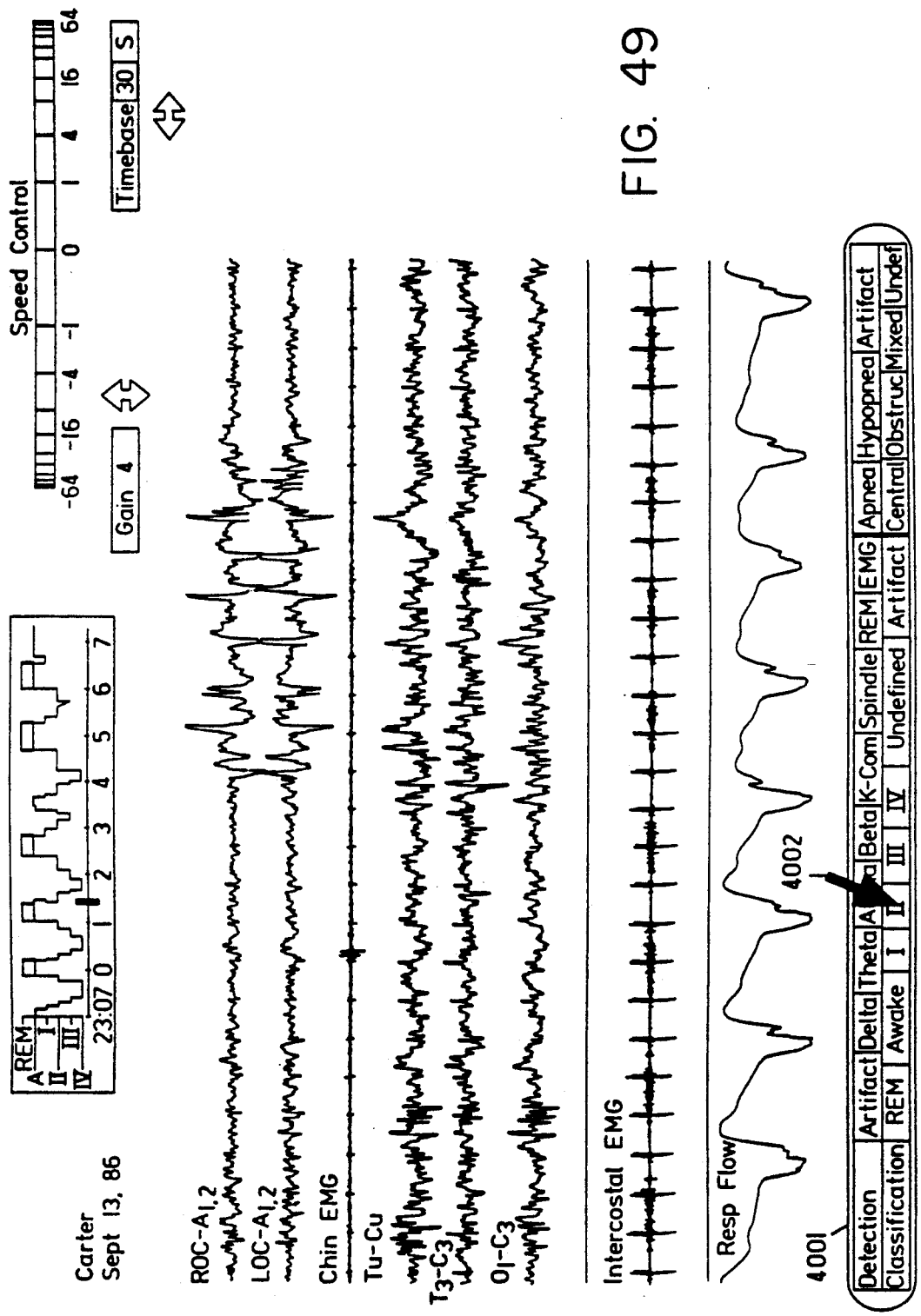
FIG. 49 is a display provided by the analysis system to an operator which illustrates the manual indication of transient patterns and the manual classification of sleep or respiration.

FIG. 49 is a screen display which illustrates the manual indication of transient patterns and the manual classification of sleep or respiration. In the prefered embodiment, a double indication/classification bar 4001 is displayed at the bottom part of the Color Display Screen which is simultaneously displaying raw data. With the manual Indication and Classification function selected, the user can choose to do either detection of patterns of classification of sleep or respiration. FIG. 47 illustrates the manner in which the currently displayed page of raw data can be classified as sleep stage II using cursor 4002 to indicate the appropriate classification. In a similar manner, a possible apnea that could occur on the current page can be indicated and classified as "central", "mixed" or "obstructive". In a similar fashion, the occurrence and extent of the transient patterns can be indicated in either channel of the raw data and can be detected by clicking with the mouse when the cursor is on the appropriate pattern type in the detection bar.

Figure 50:
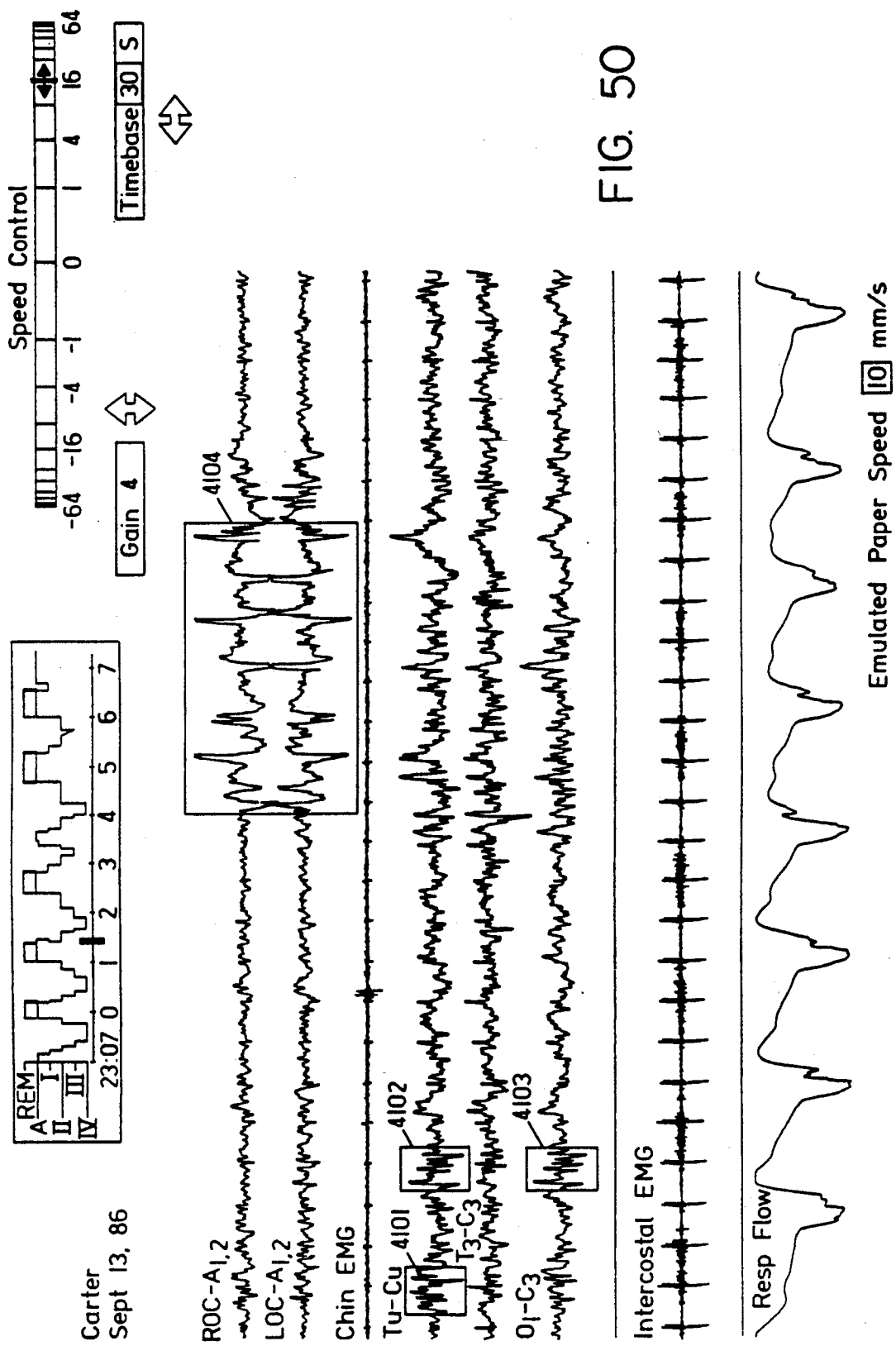
FIG. 50 is a display provided by the analysis system to an operator which illustrates the automated indication of detected patterns.

FIG. 50 is a display screen which illustrates the automated indication of detected patterns. With the Scan option selected, this figure shows the highlighting of the three detected theta-bursts 4101, 4102 and 4103. This indicates that these portions of the raw data passed all criteria for the detection of theta bursts. It also shows a detected pattern 4104 of multiple Rapid Eye Movements. The highlighting is done using the color that is associated with the individual patterns in the synoptical display of the results.

Figure 51:
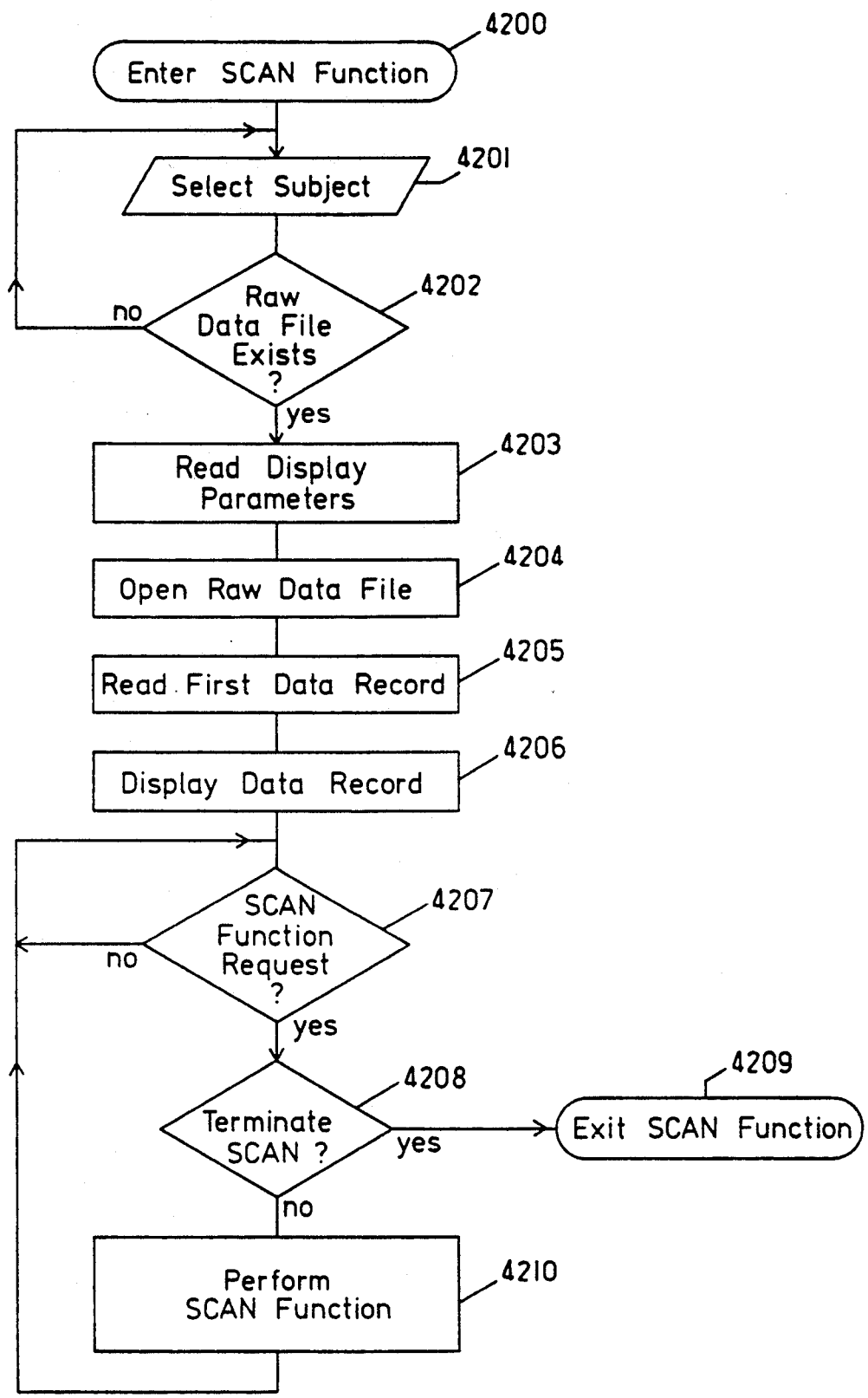
FIG. 51 is a flow diagram showing the program steps carried out by the analysis system during the Scan function.

The flow diagram showing the program steps carried out by the analysis system in the Scan function is shown in FIG. 51. After selection of the Scan function (4200), a particular subject is selected by the operator (4201) and the program determines whether a Raw Data File exists for that subject (4202): if not, the program cycles to select another subject; if so, the Display Parameters (e.g., timebase, display gain, etc.) are read (4203) and a raw data file is opened (4204). The first data record is read (4205) and displayed (4206) and a check is made to see whether the Scan function has been requested by the operator (4207). The flow diagrams of FIGS. 52–55 gives examples of the various scan sub-functions indicated by box 4210. If not, the program cycles waiting for the request; if so, a check is made to determine whether the operator has ordered termination of Scan (4208), in which case the Scan Function is exited (4209). If Scan has not been terminated, the requested scan function is performed (4210) and the program returns to wait to see if another scan function request has been made (4207).

Figure 52:
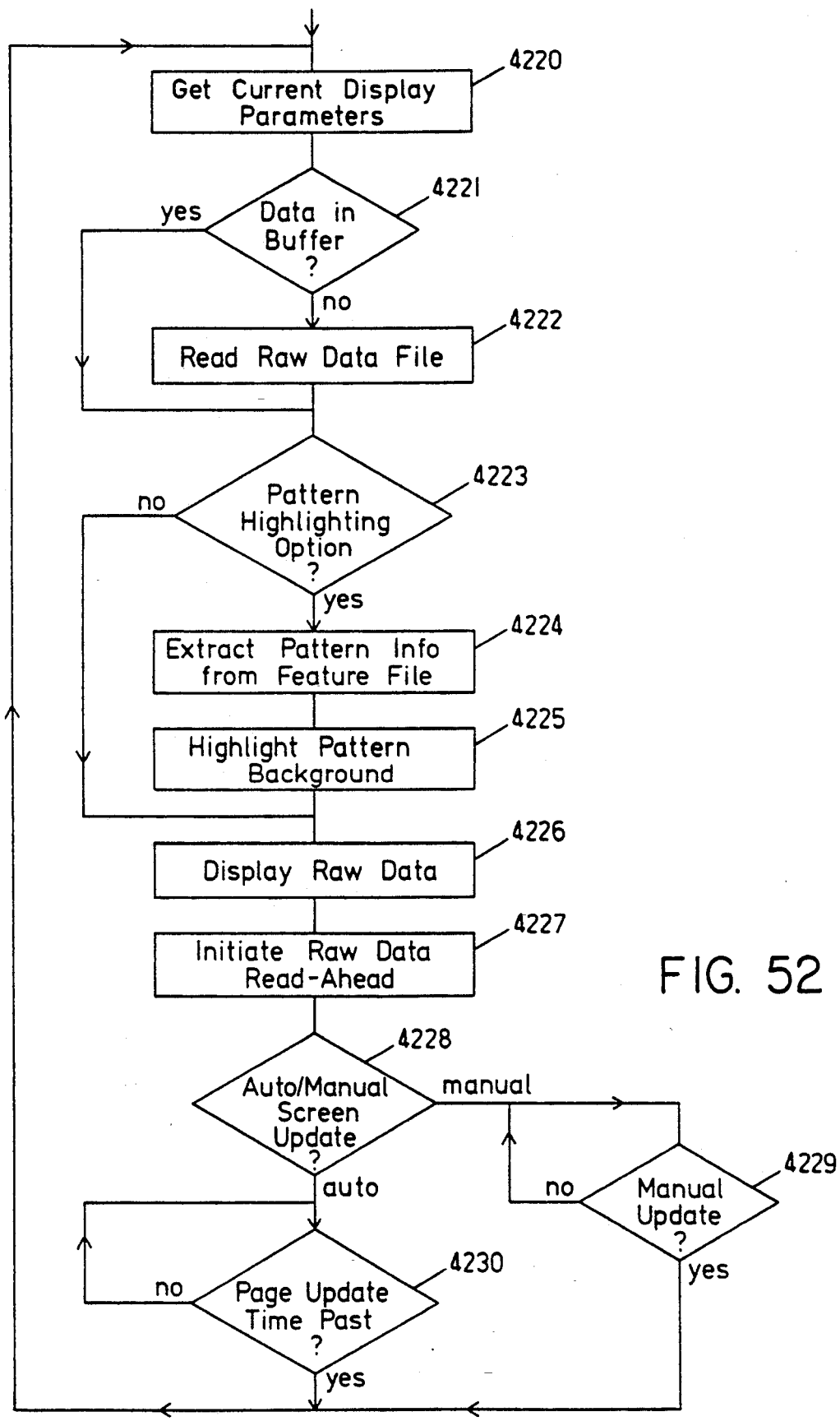
FIG. 52 is a flow diagram showing the program steps carried out by the analysis system during the Page function.

A flow diagram of the program steps in carring out the Page function is shown FIG. 52. Upon entry into the Page function, current display parameters are obtained (4220) and a check is made to see whether data is in the buffer (4221): if not, the Raw Data File is read (4222); if so, the program proceeds. A check is made to see whether the operator has requested the Pattern Highlighting option (4223) and, if so, the pattern information is extracted from the Feature File (4224), and pattern background is highlighted (4225). If the pattern highlighting option is not selected, these last two steps are omitted. The Raw Data is then displayed (4226) and Raw Data read-ahead is initiated (4227) and a check is made to see whether Automatic or Manual screen update has been requested (4228). If manual is requested, a check is made to see whether a Manual Advance was given (4229) and if not, the program waits for this instruction. If given, the program recycles back to obtaining current display parameters (4220) and displays the next page. If the operator has requested automatic screen update, a check is then made to see whether the Page Update interval time has passed (4230) and if not, the program waits until this has occured. If so, the program returns to obtaining current displayed parameters and display the next page of data.

Figure 53:
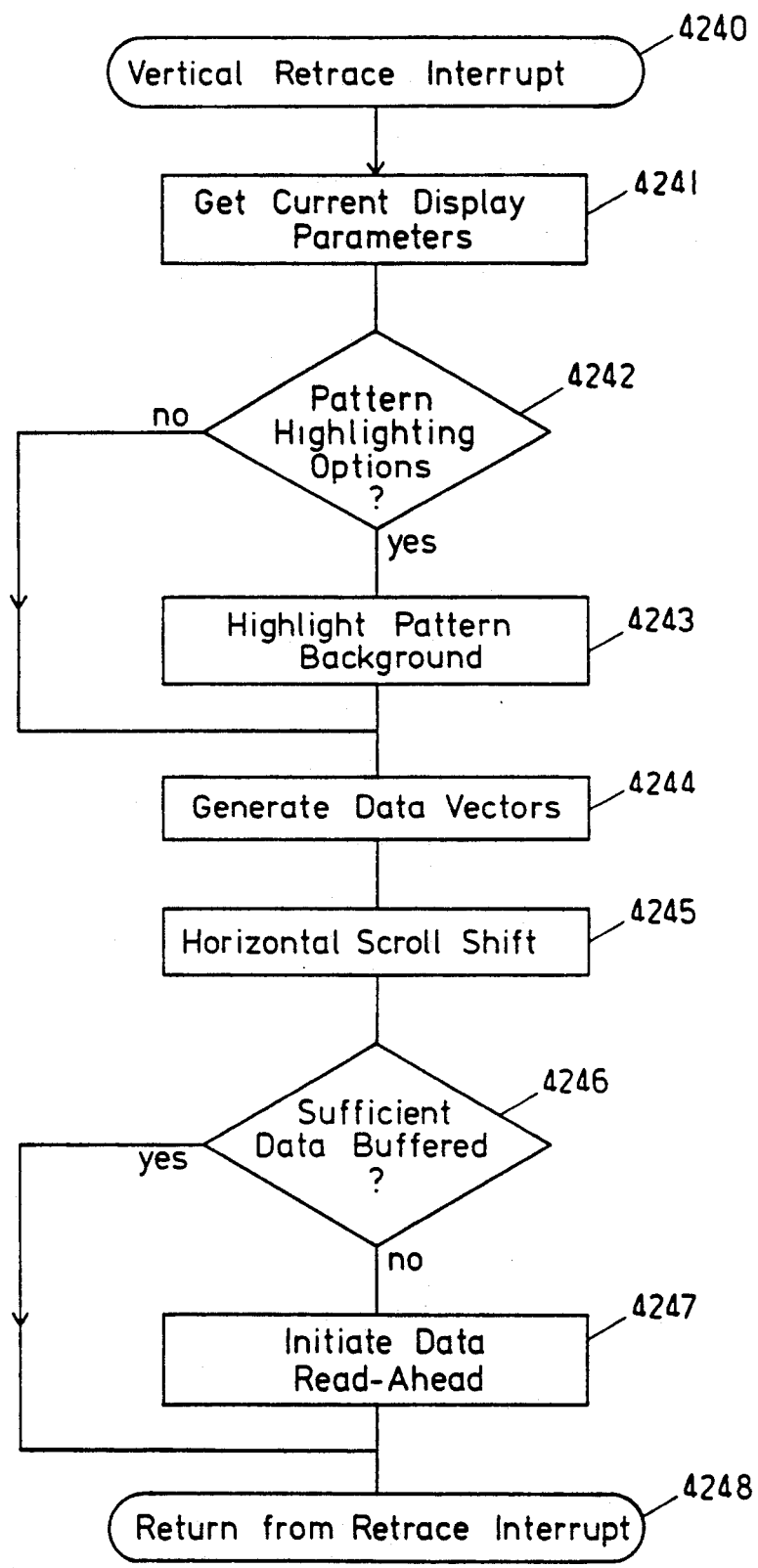
FIG. 53 is a flow diagram showing the program steps carried out by the analysis system during the Scroll function.

The flow diagram for the Scroll function carried out by the program of the analysis system is shown in FIG. 53. The program is entered upon receipt of a Vertical Retrace Interrupt (4240) from the digital processor and begins with obtaining the Current Display Parameters (4241) followed by a check to see whether the Pattern Highlighting Option has been selected (4242): if so, from the highlight information is read from the Feature file and the pattern background is highlighted (4243) and if not, the last steps are skipped. Data Vectors are then generated (4244) for the new data points to be drawn and the horizontal scroll is implemented by all pixels on the screen shifting (4245). The program then checks to determine whether sufficient data has been buffered for the next shift (4246) and if not, data read-ahead is initiated (4247); if so, this last step is omitted.

Upon completion of these actions the program then returns from the retrace interrupt (4248).

Figure 54:
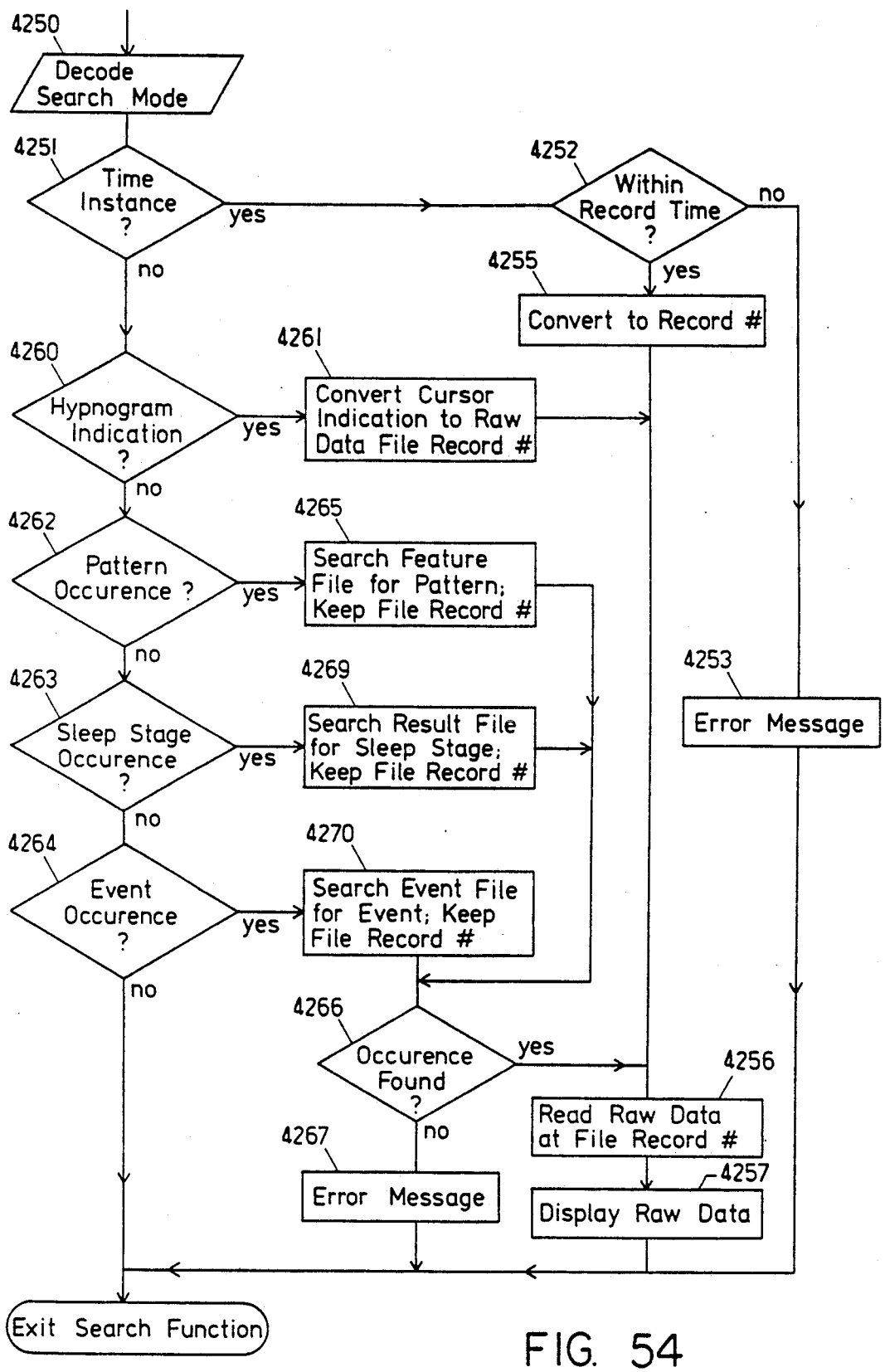
FIG. 54 is a flow diagram showing the program steps carried out by the analysis system during the Search function.
Figure 55:
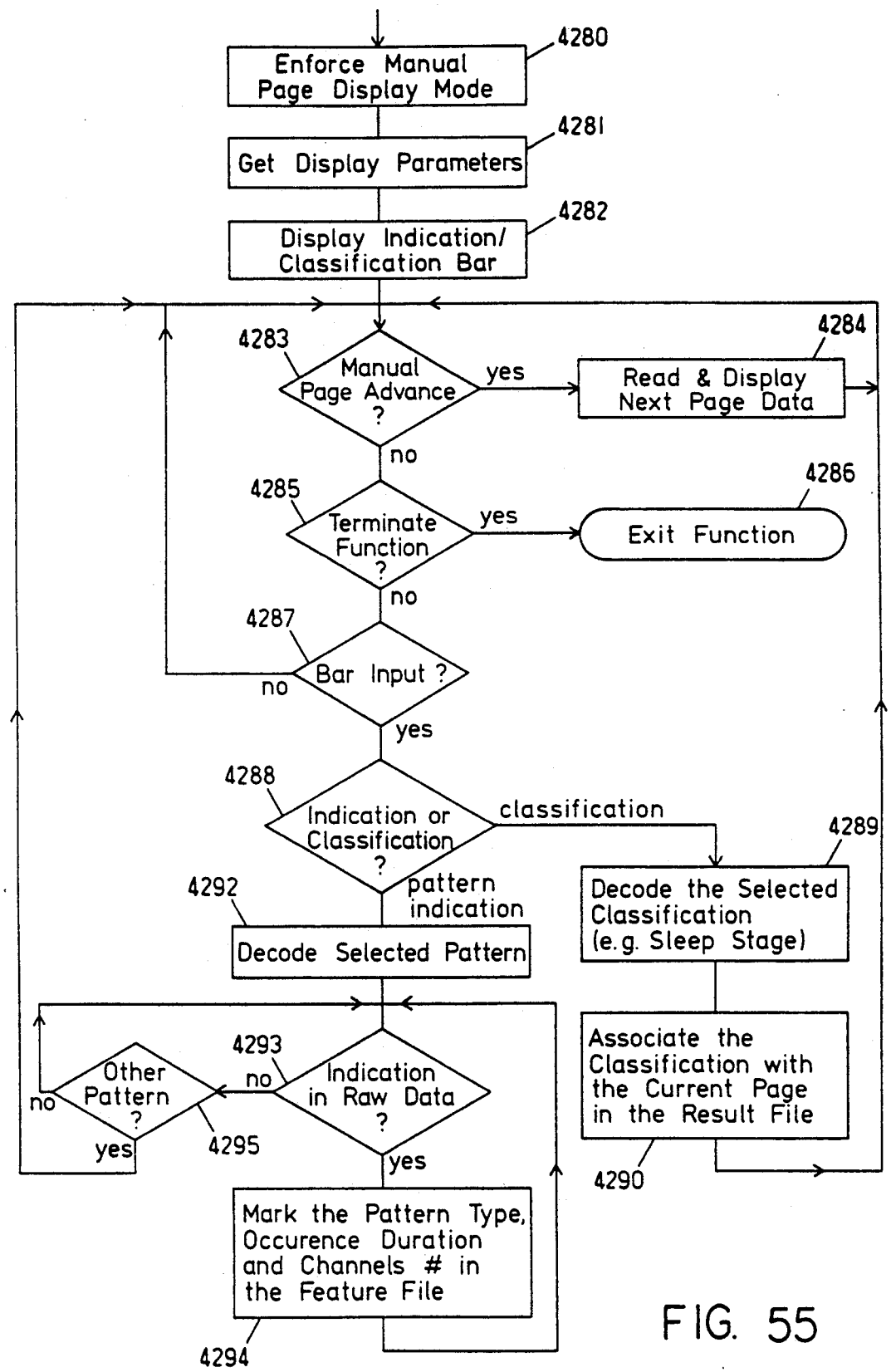
FIG. 55 is a flow diagram showing the program steps carried out by the analysis system during the Indication and Scoring function.

A flow diagram showing the program steps carried out by the analysis system in the Search function is shown in FIG. 54. Upon entry into this function, the program determines the requested Search Mode (4250) it then determines whether a Time Instance search is requested (4251). If so, the specified time is checked to determine whether it is within the Recording Time (4252) and if not, an error message is sent to the operator via the screen (4253) and the program exits from the search function (4254). If the time instance is within the Recording time it is converted to a record number (4255) into the Raw Data file and data record is read (4256) and displayed (4257) and the search function is exited (4254). If no Time Instance is requested at decision point 4251, the program determines whether a Hypnogram Indication has been made (4260) and, if so, the cursor indication is converted to a raw data file record (4261), the raw data file record is read (4256), displayed (4257) and the Search function is exited (4254). If there was no hypnogram indication specified at decision point 4260, the program checks to see if Pattern Occurrence has been designated (4262) and if so, a search is made through the Feature file for the requested pattern (4265) and, if found, the corresponding record number is for the raw data file is kept. The Raw Data at the file record number is read (4256), and displayed (4257), and then the Search function is exited (4254). If there is no Pattern Occurrence requested, the program looks to see if a Sleep Stage occurrence has been indicated (4263) and, if so, the Result file is searched for the sleep stage (4269) and if found, the corresponding record number is kept. If an occurrence is found (4266), the raw data at the file record number is read (4256) and is displayed (4257) before exit. If no occurrence is found, an error message is sent (4267) and the search function is exited. If there is no sleep stage occurrence at requested decision point 4263, the program then checks to see if an Event Occurrence has been designated (4264) and if so, the Event file is searched for the event and, if found, the corresponding record number in the raw data file is kept (4270). The program then checks to see whether an Occurrence has been found (4266) and if so, the raw data at the file record number is read (4256) and the raw data displayed (4257). If there is no occurance, an error message is given to the operator (4267) before exit. Finally, if no event occurrence was requested at decision point 4264 the program proceeds directly to exit.

The flow diagram for the Indication and Scoring function showing the steps carried out by the program of the analysis system is given in FIG. 53. Upon entry into the Indication and Scoring Function, the program selects and enforces the Manual Page Display Mode (4280) and proceeds to get the display parameters (4281) and displays the Indication/Classification bar (4282). A number of possibnle function entries are then checked. A check is made to determine whether a Manual Page Advance was selected (4283) and, if so, the Data for the next page is then read and displayed (4284) and the program cycles back to check for the next function. If a manual page advance is not requested, the program checks next to determine whether the termination of function has been selected (4285) and if so, exits from the function (4286). If termination of the function is not requested, the program checks to determine whether there is input information from the user at the Indication/Classification bar input (4287), and if not, the program returns to continue this checking cycle until a further command is received from the operator. If there is input at the indication/classification bar, the program determines whether the requested command is Indication or Classification (4288), and if classification, decodes the selected classification code (4289) and associates the classification code with the current page in the Result file (4290) and then cycles back for further commands from the operator. If Pattern Indication is selected at 4288, the selected Pattern is decoded (4292) and the program then loops until there is an Indication done on the color screen using rhe "mouse" input device (4293) or another pattern type is selected (4295). If a patter is indicated on the screen, the pattern type, its occurrence, duration and channel numbers are marked in the Feature File (4294) and the program returns to the decision point (4293). If there is no Indication done in the Raw Data on the same screen, but there is some Other Pattern selected by the operator (4295), the program recycles back to check for new function entries.

It is understood that the invention is not confined to the particular embodiments set forth herein but embraces such modified forms thereof as come within the scope of the following claims.

What is claimed is:

1. A system for analyzing physiological signals obtained from physiological sensors n a subject to determine stages of sleep comprising:
   (a) means for receiving time varying physiological signals from the sensors on the subject and for digitizing the signals to provide digital physiological signal data;
   (b) means for storing the digitized physiological signal data in correlation with time and making such data available for later long term retrieval;
   (c) analysis means receiving the digital physiological signal data for initially analyzing the data on a real time basis to detect patterns therein indicating fluctuations in physiological function using criteria, wherein the analysis means analyses the data to determine the physiological function of sleep to produce an analysis result, and wherein the physiological sensor signals include time varying EEG signal data, and wherein the analysis means includes means for separating the time varying EEG signal data into a plurality of signals corresponding to frequency bands generally conforming to the frequencies of standard EEG waveform components, including frequencies for delta waves, theta waves, beta waves and sleepspindles;
   (d) display means including a display screen for displaying to an operator on the display screen the results of the analysis from the analysis means on a real time basis, wherein the display means displays the results of the analysis as a hypnogram of the stages of sleep as a function of time;
   (e) input means receiving commands from the operator for providing new criteria specifications from the operator to the analysis means, wherein the analysis means includes means for reanalyzing the physiological data stored for long term retrieval utilizing the new criteria for determining fluctuations in physiological function, wherein the display means includes means for, during reanalysis, displaying to the operator a matrix of emulated classification rules having characterizing parameters listed on one axis of the matrix and classes on the other axis of the matrix, and for displaying reference levels and rules to the operator in matrix elements for the initial analysis, and wherein the input mans includes means for receiving input from the operator to change the reference level or rules indicated in the elements of the matrix to a level or rule desired by the operator, and the analysis means further includes means for analyzing the data utilizing the new reference levels and rules as modified by the operator to carry out the classification.

2. The system of claim 1 wherein the analysis means includes means for adjusting the frequency bands for each of the five EEG waveform components in center frequency, band width, and upper and lower cut-off frequencies in an adaptive manner to best fit presently incoming EEG signal data.

3. A method of analyzing physiological signals obtained from physiological sensors on a subject, comprising the steps of:
   (a) receiving time varying physiological signals from the sensors on the subject;
   (b) digitizing the physiological signals to provide digital physiological signal data;
   (c) storing the digitized physiological signal data in correlation with time and making such data available for later retrieval;
   (d) analyzing the physiological signal data according to criteria to detect patterns therein indicating fluctuations in physiological function and classifying a selected state of the subject based on the detected patterns to produce a result;
   (e) displaying to an operator on a display screen the results of the analysis including the classification of the state of the subject as a function of time over at least a portion of the time period that the physiological signal data was taken;
   (f) simultaneously with the display of results from (e), displaying the physiological signal data as a function of time over a time base which shows a portion of physiological signal data on the screen at any one time to allow the operator to view the physiological signal data;
   (g) receiving an input signal from the operator at selected positions in time corresponding to the physiological signal data displayed on the screen to indicate a pattern from a possible group of patterns at a point in time and storing such pattern indication with respect to the point in time of the pattern, including the step of accepting commands from the operator by a cursor displayed on the screen which is controlled by a cursor control device operated by the operator to move the cursor to a bar displaying possible patterns and allowing the operator to determine the pattern of the signal data displayed on the screen by placing the cursor over a selected pattern indicator on the screen and indicating the desired pattern at that point using the cursor control device.

4. The method of claim 3 including the steps of establishing new criteria for the detection of patterns based on the patterns indicated by the operator, storing the new criteria, and analyzing physiological signal data utilizing the new pattern criteria to detect patterns therein indicating fluctuations in physiological function.

5. The method of claim 4 wherein the step of analyzing physiological signal data is done on signal data not previously analyzed.

6. The method of claim 3 wherein the steps of (a) through (g) are repeated on subjects in a class, and including the steps of establishing new criteria for the class of subjects for patterns based on the patterns indicated by the operator, storing the new criteria for the class of subjects, and analyzing physiological signal data utilizing the new pattern criteria to detect patterns therein indicating fluctuations in physiological function.

7. A method of analyzing physiological signals obtained from physiological sensors on a subject, comprising the steps of:

(a) receiving the time varying physiological signals from the sensors on the subject;

(b) digitizing the physiological signals to provide digital physiological signal data;

(c) storing the digitized physiological signal data in correlation with time and making such data available for later retrieval;

(d) analyzing the physiological signal data to detect patterns therein indicating fluctuations in physiological function and classifying a selected state of the subject based on the detected pattern and selected classification criteria to produce a result;

(e) displaying to an operator on a display screen the results of the analysis including the classification of the state of the subject as a function of time over at least a portion of the time period that the physiological signal data was taken;

(f) simultaneously with the display from (e), displaying the physiological signal data as a function of time over a time base which shows a portion of the physiological signal data on the screen at any one time to allow the operator to view the physiological signal data; and (g) receiving an input signal from the operator at selected positions in time corresponding to the physiological signal data displayed on the screen to indicate a classification of the state of the subject from a possible group of classifications of states at a point in time and storing such classification of state with respect to the point in time of the classification, including accepting commands from the operator by a cursor displayed on the screen which is controlled by a cursor control device opeated by the operator to move the cursor to a bar displaying possible classifications and allowing the operator to determine the classification of the data displayed on the screen by placing the cursor over a selected classification indicator on the screen and indicating the desired classification at that point using the cursor control device.

8. The method of claim 7 including the steps of establishing new criteria for classification of states based on the classification indicated by the operator, storing the new criteria, and analyzing physiological signal data utilizing the new classification criteria to detect patterns therein indicating fluctuations in physiological function and classifying a selected state of the subject based on the detected patterns and the new classification criteria.

9. The method of claim 8 wherein the step of analyzing physiological signal data is done on signal data not previously analyzed.

10. The method of claim 7 wherein steps (a) through (g) are repeated on subjects in a class, and including the steps of establishing new criteria for classification of states for the class of subjects based on the classifications indicated by the operator, storing the new criteria for the class of subjects, and analyzing physiological signal data utilizing the new classification criteria to detect patterns therein indicating fluctuations in physiological function and classifying a selected state of the subject based on the detected patterns and the new classification criteria for the class.

11. A method of analyzing physiological signals obtained from physiological sensors on a subject, comprising the steps of:

(a) receiving the time varying physiological signals from the sensors on the subject;

(b) digitizing the physiological signals to provide digital physiological signal data;

(c) storing the digitized physiological signal data in correlation with time and making such data available for later retrieval;

(d) analyzing the physiological signal data to detect patterns therein indicating fluctuations in physiological function and classifying a selected state of the subject based on the detected patterns and selected classification criteria to produce a result;

(e) displaying to an operator on a display screen the results of the analysis including the classification of the state of the subject as a function of time over at least a portion of the time period that the physiological signal data was taken;

(f) simultaneously with the display from (e), displaying the physiological signal data as a function of time over a time base which shows a portion of the physiological signal data on the screen at any one time to allow the operator to view the physiological signal data; and (g) receiving an input signal from the operator at selected positions in time corresponding to the physiological signal data displayed on the screen to indicate a reclassification of the state of the subject from a possible group of classifications of states at a point in time and storing such classification of state with respect to the point in time of the classification, wherein when the operator has reclassified a particular section of the physiological signal data, the analysis results displayed on the screen which corresponds to the points in time reclassified by the operator are displayed in a different color from the remaining classification to highlight to the operator the points of the classification which were manually classified by the operator.

* * * * *